(12) United States Patent
Douglas et al.

(10) Patent No.: US 11,950,953 B1
(45) Date of Patent: Apr. 9, 2024

(54) IMAGE PROCESSING VIA A MODIFIED SEGMENTED STRUCTURE

(71) Applicants: Robert Edwin Douglas, Winter Park, FL (US); David Byron Douglas, Winter Park, FL (US)

(72) Inventors: Robert Edwin Douglas, Winter Park, FL (US); David Byron Douglas, Winter Park, FL (US)

( * ) Notice: Subject to any disclaimer, the term of this patent is extended or adjusted under 35 U.S.C. 154(b) by 382 days.

(21) Appl. No.: 17/341,501

(22) Filed: Jun. 8, 2021

Related U.S. Application Data

(63) Continuation-in-part of application No. 16/785,606, filed on Feb. 9, 2020, now Pat. No. 11,058,390, which is a continuation of application No. 16/752,691, filed on Jan. 26, 2020, now Pat. No. 11,051,782, which is a continuation-in-part of application No. 15/904,092, filed on Feb. 23, 2018, now Pat. No. 10,586,400.

(60) Provisional application No. 62/963,069, filed on Jan. 19, 2020, provisional application No. 62/961,689, filed on Jan. 15, 2020.

(51) Int. Cl.
| | |
|---|---|
| *A61B 6/00* | (2006.01) |
| *A61B 6/58* | (2024.01) |
| *G06T 5/00* | (2006.01) |
| *G06T 5/50* | (2006.01) |
| *G06T 7/00* | (2017.01) |
| *G06T 7/11* | (2017.01) |
| *G06T 15/08* | (2011.01) |

(52) U.S. Cl.
CPC ............ *A61B 6/583* (2013.01); *A61B 6/5217* (2013.01); *A61B 6/5258* (2013.01); *G06T 5/001* (2013.01); *G06T 5/50* (2013.01); *G06T 7/0014* (2013.01); *G06T 7/11* (2017.01); *G06T 15/08* (2013.01); *G06T 2207/10116* (2013.01)

(58) Field of Classification Search
None
See application file for complete search history.

(56) References Cited

U.S. PATENT DOCUMENTS

| | | | |
|---|---|---|---|
| 2003/0113003 A1* | 6/2003 | Cline | G06T 7/168 382/128 |
| 2011/0280457 A1* | 11/2011 | Nielsen | G06T 7/0012 382/128 |
| 2018/0317851 A1* | 11/2018 | Jia | A61B 5/0261 |
| 2019/0197682 A1* | 6/2019 | Hazan | G06T 7/155 |
| 2022/0230310 A1* | 7/2022 | Xie | G06V 10/758 |

\* cited by examiner

*Primary Examiner* — James A Thompson

(57) ABSTRACT

A method and apparatus of generating a modified segmented structure is disclosed. This modified segmented structure subtracts pixels or voxels in an inward direction from the segmented structure to create a smaller volume or area than the segmented structure. Analysis of the smaller volume can be useful in generating custom volumes, which can then be processed to improve visualization inside the custom volume.

20 Claims, 45 Drawing Sheets

Table 500

| | A | B | C | D | E | F | G |
|---|---|---|---|---|---|---|---|
| | Raw Data (Hounsfeld Unit) | Multiplier at time point #1 | Displayed Value at time point #1 | Multiplier at time point #2 Applied to Displayed Value #1 | Displayed Value at time point #2 | Multiplier at time point #3 Applied to Displayed Value #2 | Displayed Value at time point #3 |
| 21 | 20 | 1.2 | 24 | 1.2 | 28.8 | 1.2 | 34.56 |
| 22 | 21 | 1.2 | 25.2 | 1.2 | 30.24 | 1.2 | 36.288 |
| 23 | 22 | 1.2 | 26.4 | 1.2 | 31.68 | 1.2 | 38.016 |
| 24 | 23 | 1.2 | 27.6 | 1.2 | 33.12 | 1.2 | 39.744 |
| 25 | 24 | 1.2 | 28.8 | 1.2 | 34.56 | 1.2 | 41.472 |
| 26 | 25 | 1.2 | 30 | 1.2 | 36 | 1.2 | 43.2 |
| 27 | 26 | 1.2 | 31.2 | 1.2 | 37.44 | 1.2 | 44.928 |
| 28 | 27 | 1.5 | 40.5 | 1.5 | 60.75 | 1.5 | 91.125 |
| 29 | 28 | 1.5 | 42 | 1.5 | 63 | 1.5 | 94.5 |
| 30 | 29 | 1.5 | 43.5 | 1.5 | 65.25 | 1.5 | 97.875 |
| 31 | 30 | 1.5 | 45 | 1.5 | 67.5 | 1.5 | 101.25 |
| 32 | 31 | 1.5 | 46.5 | 1.5 | 69.75 | 1.5 | 104.625 |
| 33 | 32 | 1.5 | 48 | 1.5 | 72 | 1.5 | 108 |
| 34 | 33 | 1.5 | 49.5 | 1.5 | 74.25 | 1.5 | 111.375 |
| 35 | 34 | 2 | 68 | 2 | 136 | 2 | 272 |
| 36 | 35 | 2 | 70 | 2 | 140 | 2 | 280 |
| 37 | 36 | 2 | 72 | 2 | 144 | 2 | 288 |
| 38 | 37 | 2 | 74 | 2 | 148 | 2 | 296 |
| 39 | 38 | 2 | 76 | 2 | 152 | 2 | 304 |
| 40 | 39 | 2 | 78 | 2 | 156 | 2 | 312 |
| 41 | 40 | 2 | 80 | 2 | 160 | 2 | 320 |

| Example examination viewed | Optimal settings during 2D slice-by-slice imaging approach |
|---|---|
| Liver on CT | e.g., Liver is shaded in gray shades and with particular bands (e.g., specified range is designed to catch hypervascular tumors, necrotic tumors, etc.) in color with option for voxel manipulation. All other tissues are turned to dark gray shades. |
| Breast on digital breast tomosynthesis | e.g., Breast glandular parenchyma in gray shades with particular bands (e.g., specified range is designed to catch microcalcifications) shown in red and enlarged voxels (option). |

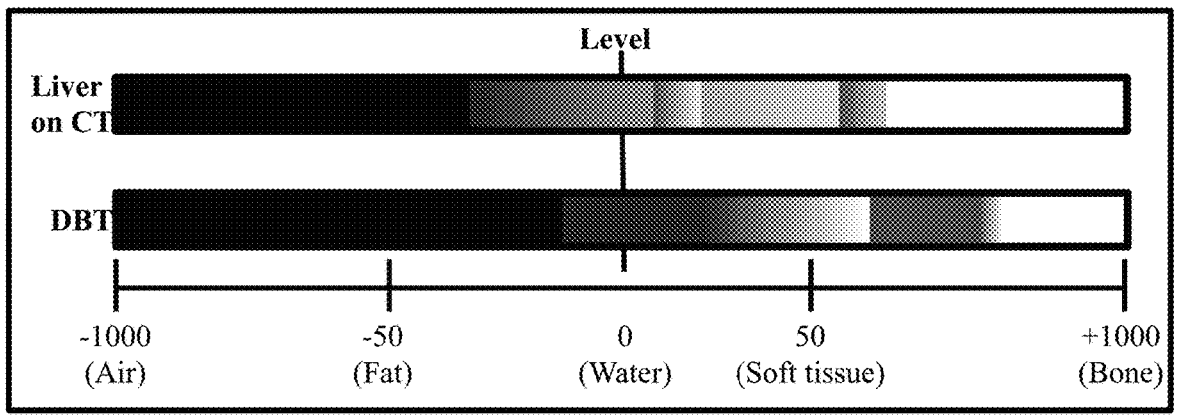

1102

1104

| Example item viewed | Optimal settings during 3D imaging (e.g., using XR headset) |
|---|---|
| Liver | e.g., Bands-wise prioritization of HU ranges is utilized within the liver and displayed in a dynamic fashion to make more subtle (but dangerous lesions) easier to detect. Implement prioritized volume rendering. All other tissues are made more translucent (e.g., sparse sampling) or are filtered. |
| Breast on DBT | e.g., Prioritized volume rendering is performed wherein the breast microcalcifications, which are of a higher priority and be displayed. All other tissues are made more translucent (e.g., sparse sampling) or are filtered. |

Figure 11

Range grouping prior to implementing visual representation adjustment logic
1202

1203　　1204　　1205

Time period #1

Optimized band (HU 50-60): yellow shades

Diminished band (HU 30-50):dark gray shades to black
1206

Time period #2

Optimized band (HU 40-50): light green shades

Diminished band (HU 30-40 & 50-60):dark gray shades to black
1207

Time period #3

Optimized band (HU 30-40): light purple shades

Diminished band (HU 40-60):dark gray shades to black
1208

Illustration of generating multiple simultaneous window/level viewing settings for viewing of 3D datasets

Performing a first windowing and leveling setting
1300

Perform segmentation of organs
1301

Generating a list of data that might be normal vs abnormal.
1302

Applying a first visual representation adjustment logic to standard window/level setting to voxels that are thought to be normal.
1303

Applying second visual representation adjustment logic (false color) that are thought to be abnormal.
1304

Option to apply additional (third or more) visual representation adjustment logic to additional ranges
1305

Figure 13

- The following image is a subvolume of a CT scan of the breast, inside of a volume-subtending 3D cursor.
- The subvolume is comprised of approximately 100 x 100 x 100 or 1 million voxels.

1400

An embodiment of this patent is to be able to improve imaging by making some voxels (e.g., voxels with Hounsfield Unit range 70-75) to have a "special" visibility.

1407

Step #1
- Divide the voxels into ranges.
  - The first range will include all voxels with Hounsfield Units between 70 and 75. Assume that there are 3 voxels in this first band.
  - The second range will include all other voxels in the volume. Assuming the 100 x 100 x 100 matrix, that would equal 999,997 voxels in this second band.

Step #2
- Assign visual representation adjustment logic to the first band of 3 voxels (e.g., color all voxels in this band yellow)

Step #3
- Assign a different visual representation adjustment logic to the second band of 999,997 voxels (e.g., color voxels in this band varying shades of gray based on Hounsfield Units and conventional windowing and leveling settings.

1500

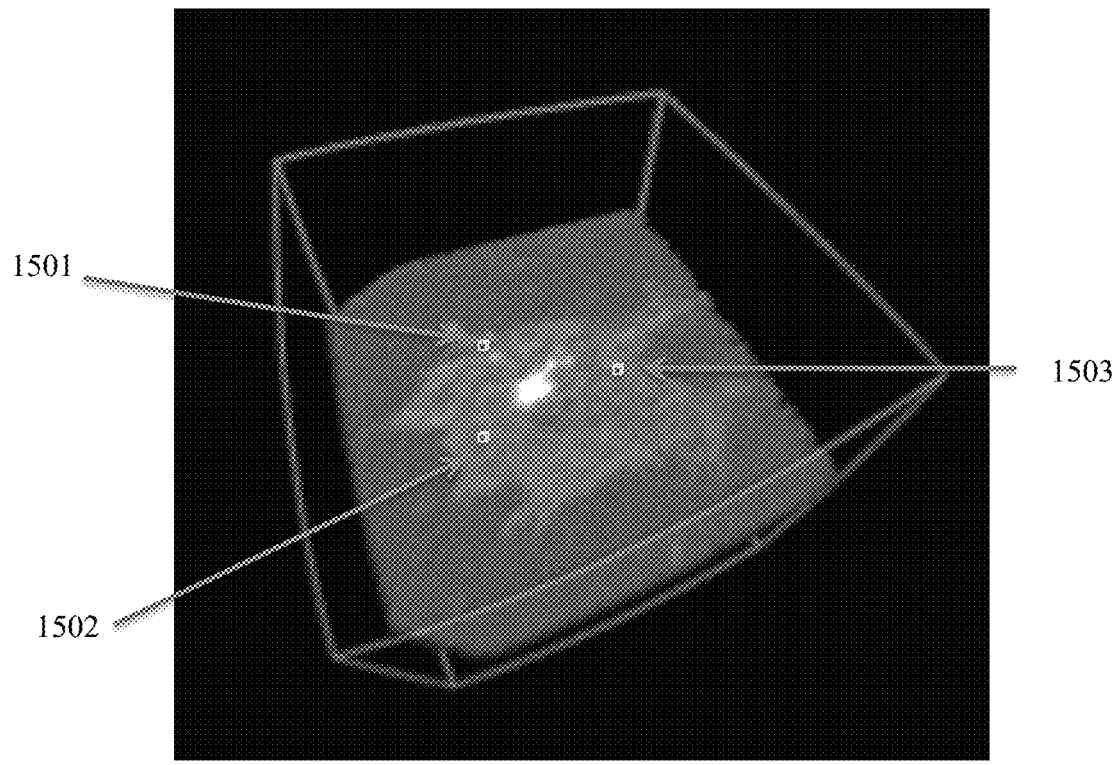

Figure 15

METHOD OF IMPROVING IMAGING QUALITY

Perform imaging examination
1600

Load an original imaging dataset of a patient wherein each pixel or voxel within the imaging dataset has an associated data unit
1601

Perform segmentation of the imaging dataset
1602

Select a first segmented structure for analysis
1603

Perform at least one measurement of the data unit(s) within the first segmented structure
1604

Determine the expected value(s) of the data unit(s) within the first segmented structure
1605

Determine at least one correction factor based on the difference between the at least one measurement(s) of the data unit(s) within the first segmented structure and the expected value(s) of the data unit(s) within the first segmented structure wherein the corrective factor can be applied to a second segmented structure to cause improved image quality
1606

Input the at least one corrective factor to modify the data units of at least one of the group comprising the first segmented structure and the second segmented structure in the original imaging dataset to create a modified imaging dataset wherein the modified imaging dataset has improved image quality
1607

Figure 16

| 50 | 50 | -1000 | -1000 | -1000 |
|----|----|-------|-------|-------|
| 50 | 50 | -1000 | -1000 | -1000 |
| 40 | 40 | -990  | -990  | -990  |
| 50 | 50 | -1000 | -1000 | -1000 |
| 50 | 50 | -1000 | -1000 | -1000 |

| 50 | 50 | -1000 | -1000 | -1000 |
|----|----|-------|-------|-------|
| 50 | 50 | -1000 | -1000 | -1000 |
| 50 | 50 | -1000 | -1000 | -1000 |
| 50 | 50 | -1000 | -1000 | -1000 |
| 50 | 50 | -1000 | -1000 | -1000 |

METHOD OF GENERATING A MODIFIED SEGMENTED STRUCTURE

Loading a three-dimensional imaging dataset
3200

Performing segmentation of a structure within the imaging dataset
3201

Determining the coordinates of a set of voxels that correspond to the outer surface of the segmented structure
3202

Determining at least one layer of voxels external to the outer surface of the segmented structure wherein the one layer of voxels is contiguous with the outer surface of the segmented structure
3203

Adding the at least one layer of voxels external to the outer surface of the segmented structure to generate a modified segmented structure
3204

Figure 32

SUBSTANTIALLY EQUAL LAYER OF VOXELS IS ADDED TO THE OUTER SURFACE OF THE SEGMENTED ANATOMIC STRUCTURE

LAYERS OF VOXELS ARE ADDED IN A NON-UNIFORM MANNER

Voxel could be preferentially added to some portions of the periphery of the segmented anatomic structure based on voxel location relative to the segmented anatomic structure (e.g., superior aspect)
3400

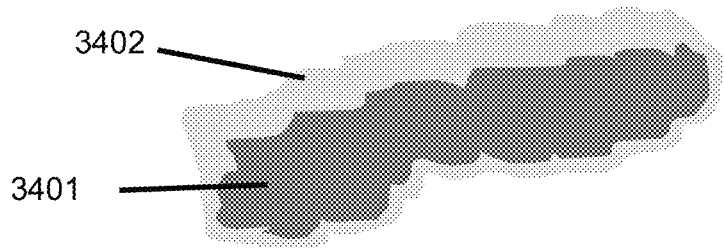

3402

3401

Voxel units could be preferentially added to some portions of the of the periphery of the segmented anatomic structure based on voxel data unit (e.g., up to 4 extra layers of voxels are added if and only if those voxels have Hounsfield Units in the range of 10-20)
3403

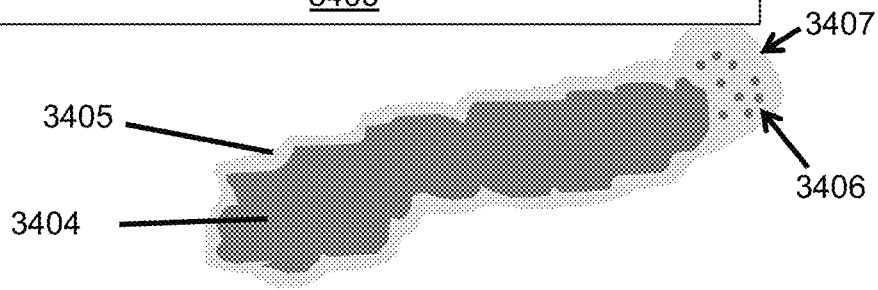

3405

3404

3407

3406

Specific anatomic structure segmented (e.g., add a minimum of 10 voxels for the pancreas, but add a minimum of 20 voxels for the kidney)
3408

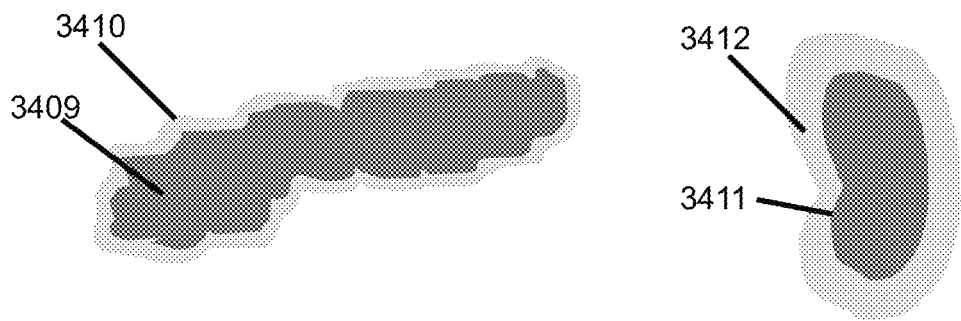

VOXELS EXTERNAL TO THE MODIFIED SEGMENTED ANATOMIC STRUCTURE ARE SUBTRACTED OR MADE TRANSPARENT

LINE IS SHOWN TO DENOTE THE MARGIN OF THE MODIFIED
SEGMENTED ANATOMIC STRUCTURE

VARYING APPEARANCES OF LINES DEMARKING THE OUTER BOUNDARY OF THE SEGMENTED STRUCTURE AND THE MODIFIED SEGMENTED STRUCTURE

LAYERS OF VOXELS ARE ADDED IN A NON-CONTIGUOUS MANNER

VISUAL APPEARANCE OF THE VOXELS IN THE MODIFIED SEGMENTED STRUCTURE ARE MODIFIED INDEPENDENTLY FROM THE VOXELS IN THE SEGMENTED STRUCTURE.

EXAMPLES OF FACTORS WHICH CAN DETERMINE THE NUMBER OF VOXELS INCLUDED IN THE MODIFIED SEGMENTED STRUCTURE

PATIENT DEMOGRAPHICS (e.g., age, gender, etc.)

For example, infants have a smaller number of voxels due to small size.
4000

METADATA (e.g., BMI, labs, etc.)

For example, BMIs >30 can have a larger number of voxels due to large size of retroperitoneal fat.

For example, if the amylase and lipase are elevated, can have a larger number of voxels around the pancreas due to higher suspicion for pancreatitis and would not want to miss a fluid collection.
4001

TYPE OF PATHOLOGY OF CLINICAL CONCERN (e.g., infection, tumor, etc.)

For example, if a stone is identified in the parotid duct, can have a larger number of voxels to improve detection of obstructive parotitis.
4002

THE TYPE OF PATHOLOGY IN THE SEGMENTED STRUCTURE.

For example, if the gallbladder contains gallstones, can have a larger number of voxels to improve detection of cholecystitis.
4003

Figure 40

MODIFIED SEGMENTED STRUCTURE AT A FIRST TIME POINT AND THE MODIFIED SEGMENTED STRUCTURE AT A SECOND TIME POINT ARE ANALYZED TO DETERMINE INTERVAL CHANGE

INPUTTING ANNOTATIONS INTO THE MODIFIED SEGMENTED STRUCTURE

UTILIZING MODIFIED SEGMENTED STRUCTURE USED IN RADIOMICS OR ARTIFICIAL INTELLIGENCE

AN INWARDLY GENERATED MODIFIED SEGMENTED STRUCTURE

# IMAGE PROCESSING VIA A MODIFIED SEGMENTED STRUCTURE

CROSS REFERENCE TO RELATED APPLICATIONS

The present application is a continuation-in-part of U.S. patent application Ser. No. 16/785,606, which is a continuation-in-part of U.S. patent application Ser. No. 15/904,092 filed on Feb. 23, 2018 (and issued as U.S. Pat. No. 10,586,400 on Mar. 10, 2020) and continuation-in-part of U.S. patent application Ser. No. 16/752,691 filed on Jan. 26, 2020, and also claims the benefit of U.S. Provisional 62/961,689 filed on 15 Jan. 2020 and U.S. Provisional 62/963,069 filed on 19 Jan. 2020.

TECHNICAL FIELD

Aspects of the present disclosure are generally related to processing three-dimensional image data, more specifically to improving image quality.

BACKGROUND

Known techniques for 3D viewing of medical images are described in U.S. Pat. No. 9,349,183, Method and Apparatus for Three Dimensional Viewing of Images, issued to Douglas, U.S. Pat. No. 8,384,771, Method and Apparatus for Three Dimensional Viewing of Images, issued to Douglas, Douglas, D. B., Petricoin, E. F., Liotta L., Wilson, E. D3D augmented reality imaging system: proof of concept in mammography. Med Devices (Auckl), 2016; 9:277-83, Douglas, D. B., Boone, J. M., Petricoin, E., Liotta, L., Wilson, E. Augmented Reality Imaging System: 3D Viewing of a Breast Cancer. J Nat Sci. 2016; 2(9), and Douglas, D. B., Wilke, C. A., Gibson, J. D., Boone, J. M., Wintermark, M. Augmented Reality: Advances in Diagnostic Imaging. Multimodal Technologies and Interaction, 2017; 1(4):29.

SUMMARY

All examples, aspects and features mentioned in this document can be combined in any technically possible way.

In accordance with an aspect an apparatus comprises: a controller; and an image processing system that generates a three-dimensional image comprising voxels corresponding to image data of a scanned volume, the image data comprising radiodensity values, the image processing system comprising visual representation adjustment logic that adjusts selected ones of the voxels based on selected ones of the radiodensity values, wherein the visual representation adjustment logic is configured in response to commands provided via the controller. Some implementations further comprise segmentation logic that performs segmentation, wherein the segmentation logic is configured in response to commands provided via the controller. Some implementations further comprise filtering logic that performs filtering, wherein the filtering logic is configured in response to commands provided via the controller. In some implementations the visual representation adjustment logic changes a grayscale value of the selected voxels. In some implementations the visual representation adjustment logic changes a color value of the selected voxels. In some implementations the visual representation adjustment logic increases dynamic range of the selected voxels. In some implementations the visual representation adjustment logic changes size of the selected voxels. In some implementations the visual representation adjustment logic changes shape of the selected voxels. In some implementations the visual representation adjustment logic changes orientation of the selected voxels. In some implementations the visual representation adjustment logic demarks the selected voxels with color. In some implementations the visual representation adjustment logic is temporally adjusted to present versions of an image corresponding to different configuration settings. In some implementations the filtering logic removes some of the selected voxels from the three-dimensional image. In some implementations the filtering logic is temporally adjusted to present versions of an image corresponding to different filter configuration settings. In some implementations the segmentation logic classifies a voxel under consideration based on the tissue type of nearest neighbor voxels in a matrix. In some implementations the segmentation logic fills a gap in a structure. In some implementations the image processing system generates multiple images from the image data using different configuration settings, and combines the multiple images to generate the three-dimensional image as a composite image.

In accordance with an aspect, a method comprises: in an image processing system, generating a three-dimensional image comprising voxels corresponding to image data of a scanned volume, the image data comprising radiodensity values, wherein generating the three-dimensional image comprises: configuring visual representation adjustment logic with configuration settings in response to commands provided via a controller; and adjusting selected ones of the voxels based on selected ones of the radiodensity values in accordance with the configuration settings. Some implementations further comprise configuring segmentation logic in response to commands provided via the controller, and performing segmentation. Some implementations further comprise configuring filtering logic in response to commands provided via the controller, and performing filtering. In some implementations adjusting selected ones of the voxels comprises changing a grayscale value of the selected voxels. In some implementations adjusting selected ones of the voxels comprises changing a color value of the selected voxels. In some implementations adjusting selected ones of the voxels comprises increasing dynamic range of the selected voxels. In some implementations adjusting selected ones of the voxels comprises changing size of the selected voxels. In some implementations adjusting selected ones of the voxels comprises changing shape of the selected voxels. In some implementations adjusting selected ones of the voxels comprises changing orientation of the selected voxels. In some implementations adjusting selected ones of the voxels comprises demarking the selected voxels with color. In some implementations adjusting selected ones of the voxels comprises temporally adjusting configuration values to present versions of an image corresponding to different configuration settings. Some implementations comprise the filtering logic removing some of the selected voxels from the three-dimensional image. Some implementations comprise temporally adjusting the filtering logic to present versions of an image corresponding to different filter configuration settings. Some implementations comprise the segmentation logic classifying a voxel under consideration based on the tissue type of nearest neighbor voxels in a matrix. Some implementations comprise the segmentation logic filling a gap in a structure. Some implementations comprise the image processing system generating multiple images from the image data using different configuration settings, and combining the multiple images to generate the three-dimensional image as a composite image.

The purpose of this continuation-in-part patent is to teach a method to improve image quality. This is useful because improved image quality can yield more accurate diagnosis of disease and lead to better treatment strategies. The methods disclosed include utilization of data unit assurance markers within the field of view of an imaging examination to improve image quality. Examples of data unit assurance markers are discussed throughout this patent, but serve as a trusted landmark of a radiodensity data unit (e.g., Hounsfield Unit in CT, Intensity unit in MRI, etc.). The preferred embodiment of this invention is the incorporation of at least one, but preferably multiple data unit assurance markers into the field of view of an image, such that through processed disclosed below, the data units of voxels or pixels in the data set can be modified. With modifications guided by the data unit assurance markers, the trustworthiness of the data is improved and diagnosis is also improved. The preferred embodiment is to utilize this process in medical imaging; however, this process can be used in any type of image processing techniques, whether it be 2D or 3D datasets.

A method and apparatus is disclosed, which significantly improves image quality. Specifically, the method disclosed utilizes structures within an image with a known or calculated value, such as a phantom or presumed homogeneous structure, such as an air mass outside of the patient. The method then performs segmentation of the imaging dataset and subsequent measurement of the structure with a known value. The difference between the known value and the measured value is used as a correction factor, which is then applied to the remainder of the dataset where values are not known. This can improve image quality by helping to generate extremely similar gray scale maps over multiple examinations and eliminate artifacts.

The preferred embodiment includes multiple steps. The first step is loading an original imaging dataset of a patient wherein each pixel or voxel within the imaging dataset has an associated data unit. Examples of this dataset include, but are not limited to, a chest radiograph comprised of pixels and a head computed tomography (CT) comprised of voxels. Next, is performing segmentation of the imaging dataset. The preferred segmentation strategies is by data unit. Other anatomic atlas based segmentation strategies can also be implemented, such as the Talairach atlas. Note that the preferred embodiment is for all voxels in the dataset to be segmented including voxels outside of the patient's anatomy. Next, select a first segmented structure. For example, the air outside of the patient is selected. Next, perform at least one measurement of the data unit(s) within the first segmented structure. For example, measurements of Hounsfield Units of the air is performed. Next, determine the expected value(s) of the data unit(s) within the first segmented structure. The preferred embodiment is to use look up tables. For example, a look up table shows that air at standard temperature and pressure is −1000 Hounsfield Units (e.g., see https://radiopaedia.org/articles/hounsfield-unit?lang=us). An alterative embodiment is to determine which structures are homogeneous. For example, air outside the patient should be substantially (approximately) homogeneous. Thus, the mean Hounsfield unit can be calculated and this calculated number used instead of the −1000 from the look up table. Next, determine at least one correction factor based on the difference between the at least one measurement(s) of the data unit(s) within the first segmented structure and the expected value(s) of the data unit(s) within the first segmented structure wherein the corrective factor can be applied to a second segmented structure to cause improved image quality.

The variation of the Hounsfield Units in the body can be related to normal tissue planes, not streak artifact. Therefore, it is difficult to perform reliable streak artifact correction by examining the tissues inside of the body alone. Thus, the preferred embodiment for streak artifact correction is to use the air. A map of the air should have homogenous Hounsfield units. If patterns (e.g., linear, triangular or trapezoid shaped) of hyperattenuation or hypoattenuation are present, then characterization of streak artifact is possible. For example, assume there is a linear-type pattern of streak artifact emanating through the brain, skull and scalp and then continuing through the air. The portion of air can be measured and analyzed. For example, the air is assumed to be −990 over a linear group, rather than the −1000. A corrective factor can be established for the air, anatomical structures (e.g., brain, skull, scalp) or combination thereof. Next, input the at least one corrective factor to modify the data units of at least one of the group comprising the first segmented structure and the second segmented structure in the original imaging dataset to create a modified imaging dataset wherein the modified imaging dataset has improved image quality. Modifications to Hounsfield Units in the dataset is performed, such that a new dataset with improved image quality is established.

In some embodiments, the method comprises wherein the selected first segmented structure is located external to the patient. Examples, include, but are not limited to, the following: air; water; and, a phantom containing multiple substances to mimic human body tissues (e.g., fat, blood, organs, bone, etc.), surgical objects, etc.

Some embodiments comprise a variety of techniques for selection of a segmented region for analysis of aberrations (e.g., the streak artifact coursing through the air as described above). The preferred embodiment is analyzing a structure wherein the data value is known, such as a phantom filled with known substances. Alternative embodiments comprise analyzing a structure whose property is known to be homogenous (e.g., air can be assumed to be homogeneous). Another alternative embodiment is analyzing an structure whose material property is known to be inhomogeneous, but predictable. This could be foam padding or fluid-type materials that layer in a predictable fashion.

Some embodiments comprise wherein the selected first segmented structure outside of the patient is at least one of the group comprising air outside of the patient, a phantom outside of the patient, a surgical object whose physical properties and imaging appearances are known and other objects which are commonly present in the scanner whose physical properties can be determined.

Some embodiments comprise wherein the selected first segmented structure is located internal to the patient. Examples include, but are not limited to the following: pacemaker, orthopedic hardware, surgical tubing, internal placement of phantoms, anatomic structures with predictable physical properties (e.g., urine) or other objects inside the patient.

Some embodiments comprise wherein the first segmented structure is one of the group comprising surgical devices, fluid compartments, and anatomic structures that are substantially fixed over time, or change over time in a predictable manner. If a substance changes over time in a predictable fashion, then look up tables may be established. Some embodiments comprise wherein a database of imaging appearance of surgical hardware whose material properties and data value is known is utilized for the corrective factor. Again, a look up table may be established.

Some embodiments comprise wherein the second segmented structure is inside the body. This second segmented structure can include an anatomic feature, such as the brain. Some embodiments comprise wherein the application of the corrective factor corrects for imaging artifacts. For example, a streak artifact causing an artificially low density coursing across a gyri of the brain can be corrected for by adding a certain number of Hounsfield Units back to the affected gyri to restore it to the true level, as if it were never affected by the streak artifact.

Some embodiments comprise wherein an array of corrective factors are determined and applied to a plurality of data units in the imaging dataset. For example, alterations in the air in the front of the head and at the side of the head can be analyzed together to determine the corrective factor that should be implemented.

Some embodiments comprise wherein a user can review the modified imaging dataset for qualitative and quantitative analysis. For example, the user can view the corrected dataset, which is unhindered by the streak artifact. The user can measure a Hounsfield Unit in a CT scan of the adrenal glands and then accurately be able to characterize a lesion. For example, radiomics analysis (e.g., histograms) can be performed on the corrected dataset.

Some embodiments comprise placing a patient in the field of view of a scanning system along with at least one phantom in the field of view of the scanning system. The next step is performing a scan containing both the patient and the at least one phantom in the scanner. This serves to provide reliable landmark(s) present during the examination to use for correction. Some embodiments comprise wherein a single or multiple phantoms are present in each imaging slice. The preferred embodiment is for the use of multiple phantoms to be placed in each imaging slice.

Some embodiments comprise wherein a user can perform windowing and leveling such that a grayscale appearance of a phantom on a first imaging examination substantially matches a grayscale to a phantom on a second imaging examination. Some embodiments comprise wherein a grayscale appearance of a phantom is used to guide the exposure of a radiograph to prevent over-exposure and to prevent under-exposure. The x-ray detector could use the information related to the number of photons that have passed through the phantom and onto the x-ray detector to determine exposure in real time, so as to prevent under-exposure and over-exposure. Additionally, for example, a chest x-ray can be performed in Florida in July 2020 with a x-ray detector and a phantom in the field of view. Then, a chest x-ray can be performed in Georgia in July 2021 with a completely different x-ray detector and phantom in the field of view. The radiologist can then match the gray scale appearance of the phantom(s) on the July 2020 imaging examination with the gray scale appearance of the phantom(s) on the July 2021 imaging examination, such that the gray scale images are substantially similar by windowing and leveling to such that each of the elements in the phantom (e.g., fat, calcium, air, etc.) appear the same brightness level (e.g., in $cd/m^2$) on the July 2020 imaging examination and the July 2021 imaging examination. Additionally, this process can be used in accordance with 62/959,918, Multi-dimensional Imaging Window, such as is described throughout the entire patent, but especially in FIGS. 1-2.

Some embodiments comprise wherein multiple phantoms are placed inside the body. For example, a patient can be instructed to swallow multiple slow dissolving capsules with characteristic radiographic signatures (e.g., water, oil, etc.). These can be used as internal phantoms in conjunction with other processed discussed in this patent.

Some embodiments comprise wherein a grayscale appearance of a phantom is used to determine whether the exposure of a radiograph is adequate. The preferred embodiment to perform this is via photon counting metrics at the site of the phantom.

Some embodiments comprise wherein the at least one phantom is placed inside one of the group of a wrap (e.g., blanket) surrounding the patient, the gurney, a coil, a table, a backboard, or other apparatuses commonly present inside of a scanner.

Some embodiments comprise an apparatus comprising: an x-ray detector; and, a phantom connected to the x-ray detector. This apparatus is useful because it can to enhance the quality of radiographs and to make the dose the lowest possible to achieve diagnostic quality image.

Some embodiments comprise an apparatus comprising: an IO device; and an image processor in communication with the IO device, the image processors comprising a program stored on a computer-readable non-transitory media, the program comprising instructions that perform: a step for loading an original imaging dataset of a patient wherein each pixel or voxel within the imaging dataset has an associated data unit; a step for performing segmentation of the imaging dataset; a step for selecting a first segmented structure for analysis; a step for performing at least one measurement of the data unit(s) within the first segmented structure; a step for determining the expected value(s) of the data unit(s) within the first segmented structure; a step for determining at least one correction factor based on the difference between the at least one measurement(s) of the data unit(s) within the first segmented structure and the expected value(s) of the data unit(s) within the first segmented structure wherein the corrective factor can be applied to a second segmented structure to cause improved image quality; and a step for imputing the at least one corrective factor to modify the data units of at least one of the group comprising the first segmented structure and the second segmented structure in the original imaging dataset to create a modified imaging dataset wherein the modified imaging dataset has improved image quality.

The purpose of this invention is also to improve efficiency and accuracy of understanding images. The preferred embodiment of this invention is to a method that a radiologist can use to improve the ability to compare a first imaging examination with a second imaging examination. For example, it the multi-dimensional imaging window process, as disclosed in U.S. Provisional Patent No. 62/959,918, multi-dimensional imaging window, that the same window and leveling settings on a CT scan can result in slight differences in the appearance of anatomic structures of the gray scale of an image. The method and apparatus disclosed in this patent overcome the problem of variability of data units (e.g., Hounsfield Units) of structures in between examinations (e.g., performed on scanner #1 vs scanner #2).

In some embodiments, consistency can be performed by placing one or more phantoms in the scanner in with the patient. The phantoms could be designed to have a variety of different material properties. For example, the phantoms could be designed with multiple compartments including oil, water, air, calcium, and soft tissue. The preferred embodiment is for the phantoms to be located in the table of the scanners (e.g., CT and MRI). Alternatively, a blanket with hundreds or even thousands of small phantoms can cover the patient during the scanner acquisition. Additionally, the phantoms can be arranged in a variety of arrangements, which include, but are not limited to, the following: a single, non-circumferential arrangement; a single circumferential arrangement; multiple layers of non-circumferential arrangement; multiple circumferential layers of arrangement; and, other arrangement patterns.

In some embodiments, the multi-dimensional imaging window, as disclosed in as disclosed in U.S. Provisional Patent No. 62/959,918, multi-dimensional imaging window can be performed, discussed throughout the whole patent, but especially in FIGS. 1-2. A structure of the same material property that is spans across a first imaging examination and a second imaging examination should have the same data units (e.g., Hounsfield units). In some embodiments, a first image is transformed to look like a second image. Several spots within the imaging dataset can be selected as "consistency" spots, to serve as pseudo-phantoms.

In some embodiments, these techniques can correct for intra-machine differences, such as a change in scanner performance over time. For example, these techniques can correct for intra-machine differences over time. In some embodiments, these techniques can correct for inter-machine differences, such as a GE CT scanner and a Siemens CT scanner.

In some embodiments, these techniques can correct for areas of decreased signal (e.g., related to a coil in an MRI scan).

A scan could be a computed tomography (CT) examination, a magnetic resonance imaging (MRI) examination, a magnetic resonance angiography (MRA) examination, a computed tomography angiography (CTA) examination, etc. or similar type scanning techniques.

A phantom is a device which contains compartments with known material properties, which can be used in conjunction with a scanner.

The purpose of this patent is to teach a method to improve diagnostic radiology, but can be applied to a variety of image processing techniques outside of the field of medicine. This is useful because improved image quality can yield more accurate diagnosis of disease and lead to better treatment strategies.

Some embodiments comprise performing segmentation of an image followed by a double windowing process. The double windowing process is designed so that the item currently being inspected by a radiologist has optimized visual representation adjustment logic (e.g., optimized windowing and leveling) and all other items in the image would not have optimized visual representation adjustment logic. The preferred way of performing non-optimized visual representation adjustment logic is to make the items not of interest darker (e.g., adjust the windowing and leveling). Other ways include blurring (e.g., making out of focus), muting (e.g., fading) and separating (e.g., creating an exploded view, as discussed in U.S. patent application Ser. No. 16/195,251. The purpose of this "double windowing" technique is to help the radiologist actively focus better on certain structures without getting scrambled (e.g., note that there are hundreds of anatomical features spread out over hundreds of slices). Thus, this technique is a method to help combat information overload. Adjust the visual representation of pixels or 3D pixel element type voxels corresponding to an item on a checklist so that the visual appearance of the item on the checklist is optimized. Adjust the visual representation of pixels or 3D pixel element type voxels not corresponding to the item on the checklist so that the all pixels or 3D pixel element type voxels not corresponding to the item on the checklist are not optimized. Display simultaneously the item on the checklist whose visual appearance is optimized and pixels or 3D pixel element type voxels not corresponding to the item on the checklist whose visual appearance is not optimized. This improves diagnostic accuracy and efficiency during an examination.

In some embodiments, a modified segmented structure to create a smooth transition between the item on the checklist which is optimized and the pixels or voxels (3D pixel element type voxels) not corresponding to the item on the checklist are not optimized. In other words, provide a transition between the optimized segmented structure and the remainder of items in the examination, which are not segmented. For example, the suggested terminology for this transition region is called a halo. The halo could have its own independent visual representation adjustment logic (e.g., windowing and leveling). Multiple halos could be used. The thickness of a halo could be as thin as a single layer of pixels or voxels or could be multiple layers thick. A modified segmented structure can be established to generate this transition region. Additional post-processing can be implemented at this site.

Some algorithms are designed to segment an anatomic feature by defining its boundary (e.g., FreeSurfer can segment the brain from the CSF). The goal of these algorithms to precisely define the boundary of the structure of interest. In FreeSurfer, for example, the whole brain volume, the cerebrospinal fluid volume can be determined. In oncology, segmentation can be utilized to analyze the inside of a tumor to perform quantitative analysis (e.g., volume measurements) of the tumor.

The preferred embodiment disclosed incorporates voxels surrounding a segmented structure (e.g., a halo appearance), such that analysis of the voxels outside of a particular structure can be performed. There are some applications wherein this technique can be useful. For example, in pancreatitis, fluid can seep into the adjacent tissues outside of the pancreas. Thus, by creating a halo of voxels and analyzing this for increases in accumulation of fluid would have benefit by improving detection of pancreatitis. The preferred embodiment is to utilize this process in 3D medical imaging, such as CT and MRI examinations; however, this process can be used in any type of image processing techniques, whether it be 2D or 3D datasets. In 2D datasets, the "halo" would be comprised of pixels.

The preferred embodiment is a method comprising multiple steps. First, load an three-dimensional imaging dataset into an image processing suite. Second, perform segmentation of a structure within the imaging dataset. Third, determine the coordinates of a set of voxels that correspond to the outer surface of the segmented structure. Fourth, determine at least one layer of voxels external to the outer surface of the segmented structure wherein the at least one layer of voxels is contiguous with the outer surface of the segmented structure. Fifth, add the at least one layer of voxels external to the outer surface of the segmented structure to generate a modified segmented structure. This modified segmented structure will therefore contain some of the item of interest and some additional voxels. An alternative embodiment is wherein the fourth and fifth steps add a layer of voxels external to the outer surface of some portions of the segmented structure, but not the entirety of the segmented structure. This alternative embodiment can be useful in the event to design a halo, such that it includes fat surrounding some portions of the organ, but does not include a portion of bone that touches another portion of the organ. The halo can be designed to include some structures, but not others. Thus, some embodiments will be symmetrically modified segmented structures and some embodiments will be asymmetrically modified segmented structures. Some embodiments will therefore not modify (e.g., expand a voxel layer or pixel layer beyond the segmented region) for some portions of the segmented structure.

Some methods comprise a substantially equal layer of voxels is added to the outer surface of the segmented structure. For example, consider the kidney, which is surrounded by a large region of retroperitoneal fat. An example would be to generate a 1 cm halo of fat surrounding the kidney to comprise the modified segmented structure. The layer of voxels added would be approximately 1 cm on all sides of the kidney.

Some methods comprise wherein layers of voxels are added in a non-uniform manner wherein the non-uniformity is determined by a inputted factors. For example, the non-uniformity could be determined by voxel data units. A threshold could be established to denote a boundary not to be exceeded. For example, the layers of voxels could be added so long as the voxels are in the Hounsfield Unit range of −100 to +30 (which would represent fat or fluid stranding within the fat), but no additional layers would be added to the modified segmented structure if outside of this range (which would represent tissues other than fat or fluid stranding within the fat). Additionally, voxels could be restricted from being added to the modified segmented structure if they exceed a certain x, y, z value. Additionally, voxels could be restricted being added to the modified segmented structure (e.g., kidney) if the voxels reach or are within a certain distance of another segmented structure (e.g., spleen). Additionally, the amount of modification that is performed could be limited depending on the specific structure that is segmented (e.g., liver has up to 10 voxel layers, spleen up to 8 voxel layers, etc.).

Some embodiments comprising wherein the voxels external to the modified segmented structure are subtracted or made transparent. This can be performed to allow enhanced viewing of the modified segmented structure (e.g., including the kidney and some of the surrounding retroperitoneal fat) in an unobstructed fashion, such as is performed in U.S. Pat. No. 8,384,771, Method and Apparatus for three-dimensional viewing of images.

Some embodiments further comprise wherein a line is shown to denote the margin of the modified segmented structure. For example, a radiologist can easily distinguish the boundary of the kidney, which is approximately 40 Hounsfield Units on a non-contrast CT scan, from the retroperitoneal fat, which is approximately −100 Hounsfield Units on a non-contrast CT scan when viewing on a soft tissue window viewing setting. However, the radiologist would not know the boundary of the modified segmented structure because there would be no clear transition of Hounsfield Units at this site. Thus, there is utility of adding a line demarking the boundary of the modified segmented structure. This line could have a variable appearance and be adjustable per user preference. The preferred embodiment is for this to be performed in an automated fashion; however, an alternative embodiment is for the user could also modify (e.g., through click and drag mouse inputs) the area or volume of the modified segmented structure. Examples of the changes in appearance include, but are not limited to, the following: solid; dotted; dashed; single; double; thin weight; medium weight; thick weight; varying colors; glow patterns; blinking; or other line appearances.

Some embodiments comprise wherein the modified segmented structure is used to designate a volume for which additional image processing is performed. The volume (e.g., a region surrounding the pancreas) would be included into the additional image processing. The image processing that can be performed includes, but is not limited to, the following: visual analysis; radiomics (e.g., computational techniques performed to extract quantitative features from medical images); and, artificial intelligence (e.g., deep learning). For example, this process is further described in PCT/US2019/023968, Radiologist-assisted machine learning with interactive, volume-subtending 3d cursor, see FIGS. 1-20.

Some embodiments further comprising wherein the additional image processing is used to determine a dose of a pharmaceutical. For example, if the patient is diagnosed with pyelonephritis, an antibiotic dose is prescribed. If the modified segmented structure is determined (e.g., through AI-generated diagnosis) to show an imaging finding (e.g., fat stranding in the retroperitoneum), then the dose of the pharmaceutical (e.g., antibiotic) could be altered based upon the imaging finding. This process is further described in U.S. Provisional Patent Application No. 62/957,300, A method and apparatus for using quantitative and qualitative data from medical imaging examinations for precise pharmacologic dosing regimen, see FIGS. 1-18.

Some embodiments comprise wherein the additional image processing is performed on the least one layer of voxels external to the outer surface of the segmented structure wherein the one layer of voxels is contiguous with the outer surface of the segmented structure. Examples include techniques taught in U.S. patent application Ser. No. 15/904,092, Processing 3D medical images to enhance visualization, see FIGS. 1-10. Some embodiments comprise wherein the additional image processing at least one of the group comprising: radiomics; and, artificial intelligence. Some embodiments comprise wherein the additional image processing is used to determine a dose of a pharmaceutical.

Some embodiments comprise wherein additional non-contiguous voxels are added to form a modified segmented structure. This is useful because it is possible that some non-contiguous items could be highly correlated to a segmented structure (e.g., colon thickening representing colon cancer and an adjacent round, enlarged mesenteric lymph node).

Some embodiments comprise wherein the visual appearance of the voxels in the modified segmented structure are modified independently from the voxels in the segmented structure. This technique is further disclosed in U.S. patent application Ser. No. 15/904,092, Processing 3D medical images to enhance visualization, see FIGS. 1-10.

Some embodiments comprise wherein the number of voxels included in the modified segmented structure is dependent on additional factors. For example, first consider patient demographics. For example, infants have a smaller number of voxels due to small size. Next, consider metadata (e.g., labs, BMI, etc.). For example, BMIs>30 can have a larger number of voxels due to large size of retroperitoneal fat. For example, if the amylase and lipase are elevated, can have a larger number of voxels around the pancreas due to higher suspicion for pancreatitis and would not want to miss a fluid collection. Next, consider the type of pathology of clinical concern (e.g., tumor, infection, etc.). For example, if a stone is identified in the parotid duct, can have a larger number of voxels to improve detection of obstructive parotitis. Next, consider the type of pathology in the segmented structure. For example, if the gallbladder contains gallstones, can have a larger number of voxels to improve detection of cholecystitis. Additionally, the size of the pathology in the segmented structure can also be factored in. For example, if the patient has a 2 mm renal stone, then the modified segmented structure can be 5 pixels or 3D pixel type voxels layers thick. If the patient has a 10 mm renal stone, then the modified segmented structure can be 30 layers thick.

Some embodiments comprise wherein the modified segmented structure at a first time point and the modified segmented structure at a second time point are analyzed to determine interval change. Some embodiments comprise wherein voxel manipulation is perform to achieve precise registration of soft tissues, which can deform, rotate and translate. This is further taught in U.S. patent application Ser. No. 16/195,251, Interactive voxel manipulation in volumetric medical imaging for virtual motion, deformable tissue, and virtual radiological dissection, see FIGS. 1-23. Additionally, techniques which teach which voxel on a first examination corresponds to which voxel on a second examination are also useful in determining interval change, which is further taught in U.S. Provisional Application 62/939,685, Method and apparatus for development of an organ-specific coordinate system, see FIGS. 1-7.

Some embodiments comprises wherein the number of voxels included in the modified segmented structure can be varied. The preferred embodiment is for this to be performed in an automated fashion (e.g., through AI); however, an alternative embodiment is for the user could also modify (e.g., through click and drag mouse inputs) the area or volume of the modified segmented structure.

Some embodiments comprise wherein annotations are inputted into the modified segmented structure. This could be used to facilitate discussion between physicians.

Some embodiments comprise wherein the visual appearance of the voxels in the modified segmented anatomic structure are modified independently from the voxels in the segmented structure.

Some embodiments comprise wherein a first modified segmented structure affects the size, shape or configuration of a second modified segmented structure. For example, a large modified segmented structure including retrperitoneal fat of the pancreas causes the modified segmented structure of the kidneys to be commensurately smaller.

Some embodiments comprise loading an imaging dataset, performing segmentation of a structure within the imaging dataset, determining an outer surface of the structure, determining at least one layer of pixels or voxels internal to the outer surface of the structure wherein the at least one layer of pixels or voxels is conformal with the outer surface of the structure and subtracting the at least one layer of pixels or voxels internal to the outer surface of the structure to generate a modified segmented structure.

Some embodiments comprise loading an imaging dataset, segmenting of a structure within the imaging dataset to define a first boundary wherein the first boundary marks an outer surface of the structure, determining at least one layer of pixels or voxels internal to the first boundary wherein the one layer of pixels or voxels is conformal with the first boundary, and generating a second boundary wherein the second boundary is generated by moving inward the at least one layer of pixels or voxels from the first boundary.

Some embodiments comprise performing segmentation of a structure within the imaging dataset, determining an outer surface of the structure, determining at least one layer of pixels or voxels internal to the outer surface of the structure wherein the at least one layer of pixels or voxels is conformal with the outer surface of the structure, and subtracting the at least one layer of pixels or voxels external to the outer surface of the structure to generate a modified segmented structure.

BRIEF DESCRIPTION OF THE FIGURES

The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables, are not shown. It will be appreciated by those of ordinary skill in the art that the particular sequence of steps described is illustrative only and can be varied without departing from the spirit of the invention. Thus, when possible, the steps can be performed in any convenient or desirable order.

FIG. 5 illustrates mathematical adjustments of voxels to enhance discrimination between voxels based on grayscale values.

FIG. 11 illustrates optimal viewing settings for 2D imaging and for 3D imaging.

FIG. 13 illustrates generating multiple simultaneous window/level settings for viewing of 3D datasets.

FIG. 15 illustrates with overcoming challenges in visualizing certain ranges when using viewing multiple windowing.

FIG. 16 illustrates a method of improving image quality.

FIG. 32 illustrates a method of generating a modified segmented structure.

FIG. 34 illustrates layers of voxels added in a non-uniform manner.

FIG. 40 illustrates examples of factors which can determine the number of voxels included in the modified segmented structure.

DETAILED DESCRIPTION

Figure 1:
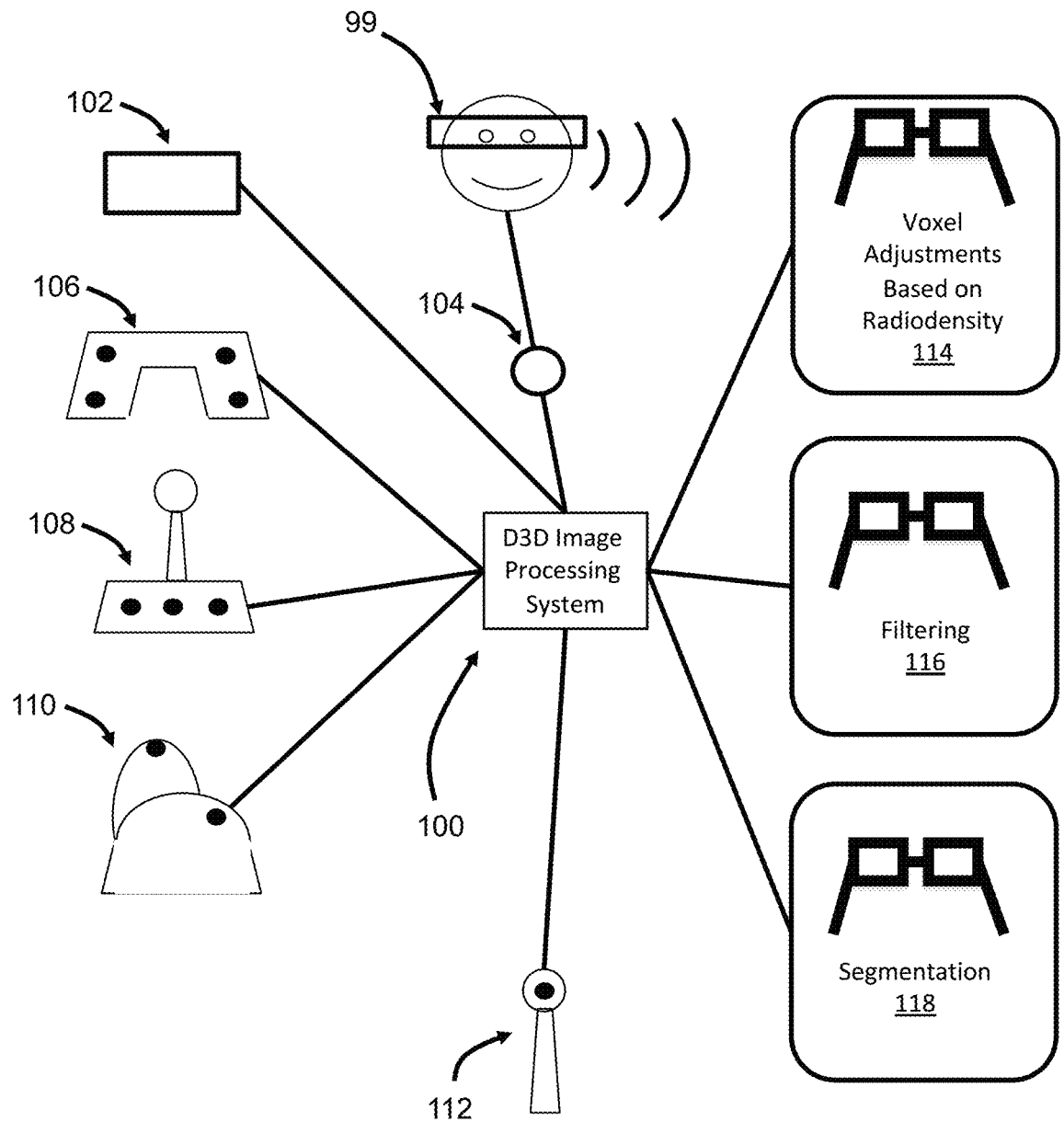
FIG. 1 illustrates a D3D image processing system.

Some aspects, features, and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

In a D3D imaging system, a radiologist uses a controller to manipulate 3D (three-dimensional) images that may be viewed via special glasses or a VR (virtual reality) headset. The 3D images may be generated from radiological scan data, for example and without limitation from X-ray radiography, CT (computed tomography), PET (positron emission tomography), or MRI (magnetic resonance imaging). There will normally be a linear relationship between density or radiodensity values from the scan data and the grayscale values assigned to corresponding voxels of the 3D images. Advantages of existing examples may include improved depth perception and an improved human machine interface. Still, there are several challenges faced with this approach. First, an area of interest (e.g. tumor) may be in close proximity to structures that are similar in composition/density. Isolating the area of interest for better examination may be difficult. Second, many soft tissues in the body are mobile and deformable, so it can be difficult to achieve the best orientation to properly compare the tumor at multiple time points. Efficiently aligning the orientation to do so may be difficult. Third, certain portions of a tumor can respond to treatment and decrease in size while other portions of a tumor demonstrate increases in size. The pattern of tumor shrinkage has important prognostic implications. Furthermore, composition and complex morphologic features including speculations (spikes extending from the surface), irregular margins and enhancement also have important implications. Consequently, there is a need for a system that facilitates recognition of the subtle, yet important changes in size, shape and margins. Fourth, a patient with metastatic cancer has several areas of interest in different areas of the body. It is difficult and time consuming to find each of the areas of interest at every time point to determine interval change. Consequently, there is a need for a system that enables the observer to do this efficiently.

FIG. 1 illustrates an improved D3D image processing system 100 and various types of controllers and a VR headset 99 that interface with the D3D image processing system. A wide variety of controllers may be utilized, possibly including but not limited to one or more of a keyboard 102, microphone 104 (for voice control), hand held game-type controller 106, joy stick 108, high-end mouse 110, and wand 112. The controllers are used to enter commands that control an application that processes 3D image data and displays that 3D image data. As will be explained in greater detail below, the controllers are used to select, configure and implement image processing techniques including: voxel adjustments based on radiodensity 114; filtering 116; and segmentation 118.

Figure 2:
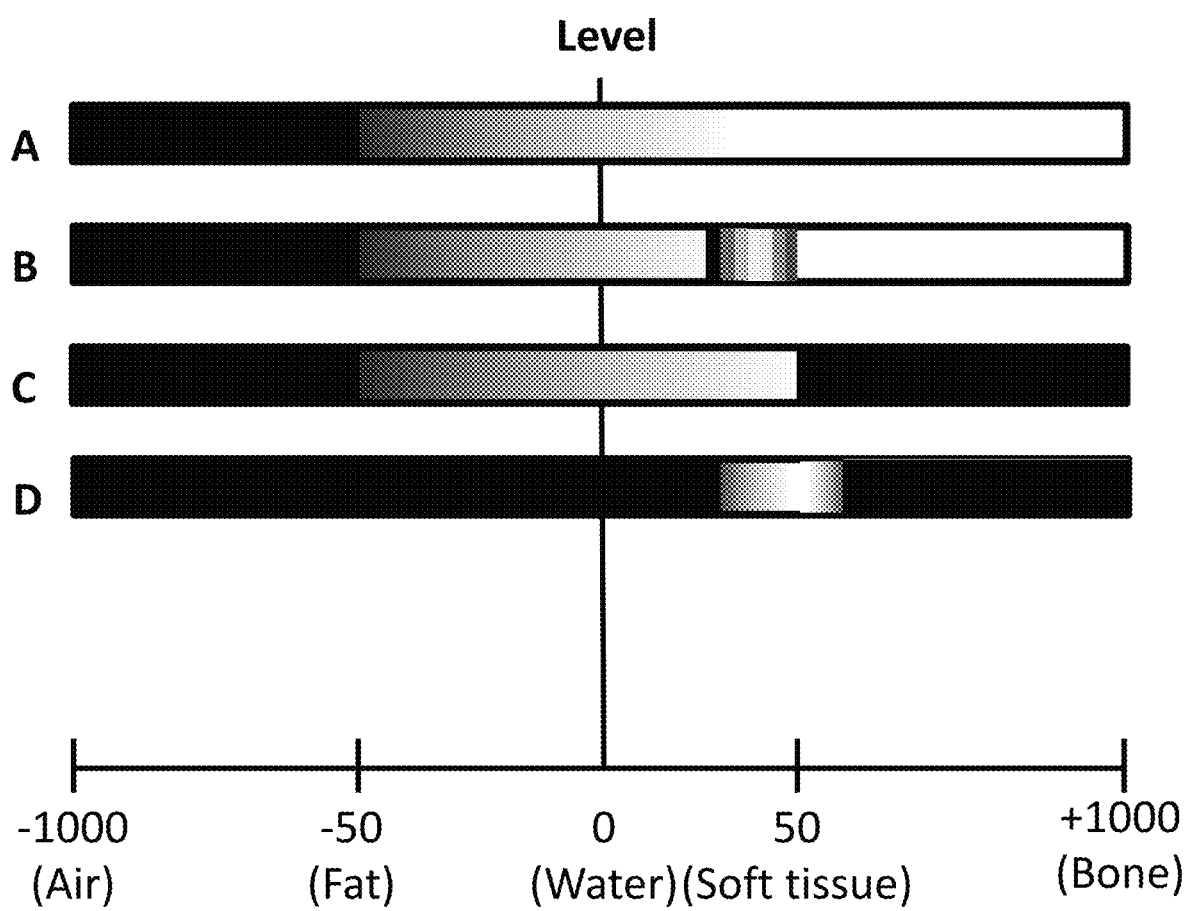
FIG. 2 illustrates aspects of voxel adjustments based on radiodensity in greater detail.

Referring to FIG. 2, an aspect of voxel adjustments based on radiodensity is grayscale and color adjustments. Raw 3D image data may include radiodensity values for locations in a scanned volume. Initially, grayscale and/or color values that are linearly related to radiodensity values may be assigned to voxels of an image corresponding to the 3D image data. Grayscale and/or color values corresponding to selected radiodensity values may then be adjusted for image enhancement. In the illustrated example, relative radiodensity values are used, namely HU (Houndsfeld Units). Initially assigned grayscale values may be linearly related to the HU values. Controller-entered commands enable the radiologist to independently adjust the relationship between HU values and grayscale and/or color values, e.g. from linear to non-linear. This may advantageously enhance presentation of tissue types of interest. In figure line A of the illustrated example, air within the body is initially shown in grayscale as black, whereas bone is shown as white. In line B, false color has been added to a region corresponding to an HU range that represents soft tissue. Selection, configuration, and application occur in response to controller-entered commands. In line C, grayscale values corresponding to HU values above a specified level have been changed to black (or not included in the voxel set displayed). In line D, grayscales values both above and below an HU range have been changed to black (or not included in the voxel set displayed). Tissues and other features may be distinguished based on radiodensity. Consequently, features and tissues may be selected, enhanced, and excluded based on radiodensity.

Although radiodensity is described herein as a basis for selection, it should be understood that a variety of related values, analogs, or proxies could be used instead of, or to represent, radiodensity. For example, and without limitation, tissue density could be used for selection. Further, a grayscale value, or range of values, could be directly selected and adjusted. The term radiodensity as used herein is intended to encompass all related values, analogs, and proxies.

Another aspect of voxel adjustments based on radiodensity is increasing the dynamic range of the displayed voxels. A process to achieve this may involve the following steps: selecting a volume of interest; removing all external tissue; setting a lower bound level of interest and a top bound; removing all tissue external to these bounds; extending the bounds by a factor of a selected factor (e.g., 2 or 10); and interpolating voxel grayscale values between the two bounds. This will have the effect of increasing dynamic range. Humans can only distinguish 7-8 bits of grayscale. This expansion of the upper/lower bounds would distinguish 10 bits or more, thus enabling the possibility of earlier and/or improved detection rate of tumors.

Figure 3A:
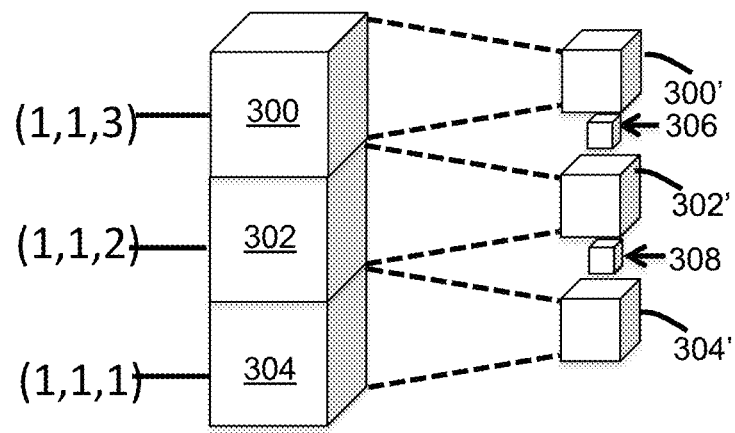
FIGS. 3A, 3B, and 3C illustrate adjustment of voxel size, shape, and orientation, respectively.

As shown in FIG. 3A, another aspect of voxel adjustments based on radiodensity is changing voxel size via controller-entered commands. For example, voxels having a selected radiodensity, or within a selected range, are adjusted in size by a selected magnitude. This technique may be used to cause a corresponding tissue type to be presented as semi-transparent. In the illustrated example, voxels 300, 302, 304 are reduced in size, yielding corresponding voxels 300', 302', 304', thereby permitting visualization of voxels 306, 308 that are more distant from the viewing point, i.e. deeper in the volume. Consequently, features can be seen that would otherwise have been occluded by the size-adjusted voxels in the near field of view.

Figure 3B:
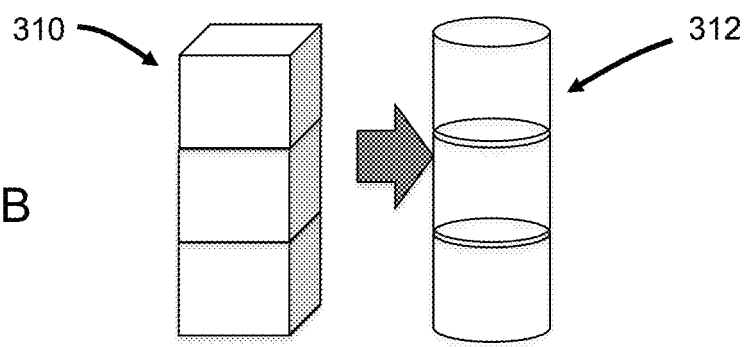

Referring to FIG. 3B, another aspect of voxel adjustments based on radiodensity is changing the shape of voxels via controller-entered commands based on radiodensity or some other basis. In the illustrated example, standard cubic voxels 310 having a selected radiodensity, or within a selected range, are adjusted to generate corresponding cylindrical voxels 312. Voxel shape may be selected to allow a smoother presentation of a feature being observed. For example, blood vessels could be better represented by cylindrical voxels as opposed to a column of cubes.

Figure 3C:
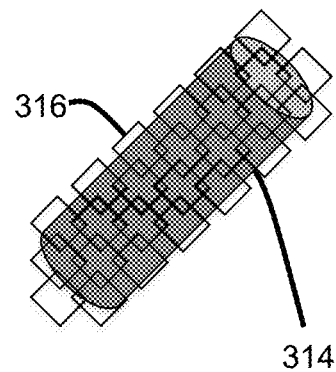

Referring to FIG. 3C, another aspect of voxel adjustments based on radiodensity is changing voxel orientation via controller-entered commands. In the illustrated example voxel orientation is changed from alignment with standard X, Y, Z axes as shown in FIG. 3A, to a slanted coordinate system that more closely aligns with the with the patient's anatomy. For example, voxel orientation may be changed to more closely represent the curvature of body contents to include tissues or surgical devices. In the illustrated example the voxel orientation is adjusted relative to a blood vessel 314 by adjusting axes of the sides or edges 316 of the voxels. Voxels associated with the blood vessel or other tissue types may be selected based on radiodensity or some other basis.

Figure 4A:
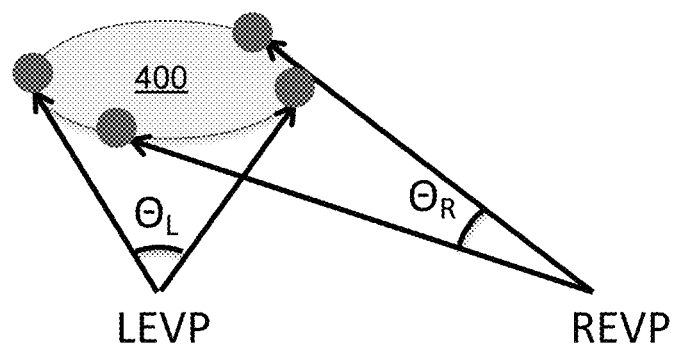
FIGS. 4A and 4B illustrate feature demarcation.
Figure 4B:
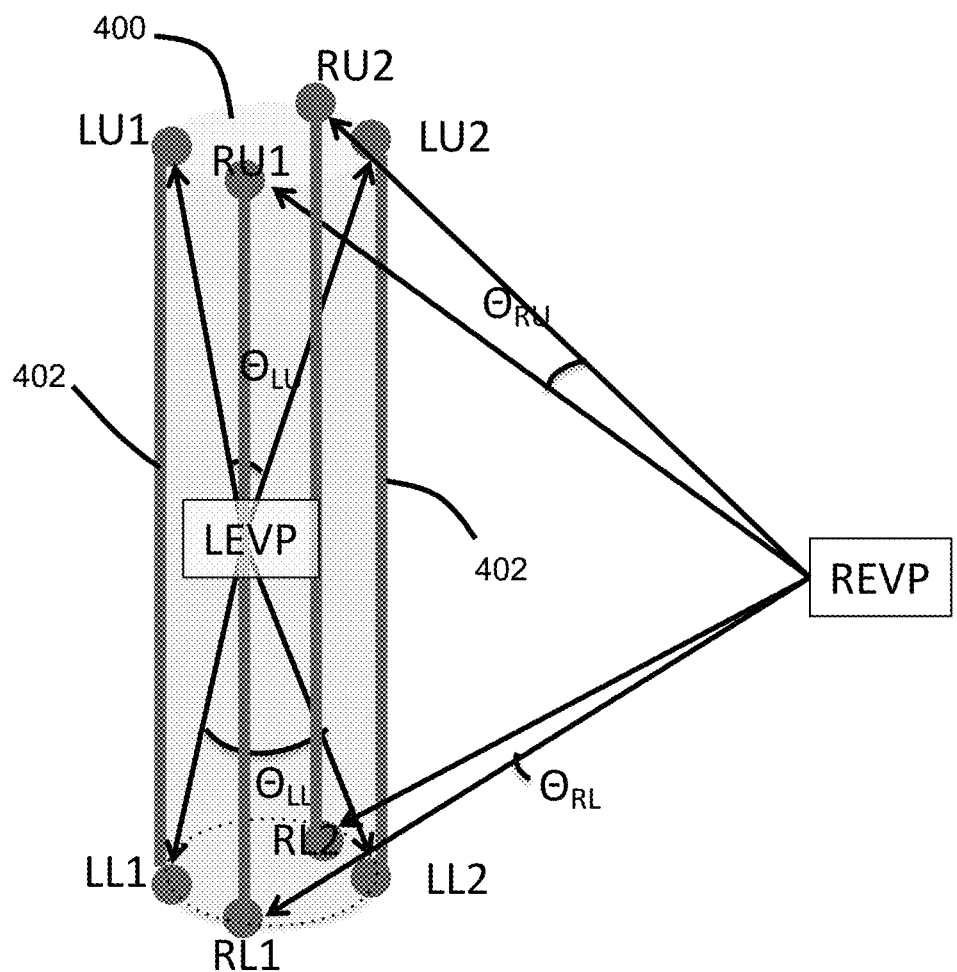

Referring to FIGS. 4A and 4B, another aspect of voxel adjustments based on radiodensity is feature demarcation. In the illustrated example, voxels associated with a vein 400 are demarked with blue lines 402 to enhance visualization. Although a vein is shown as an example, a wide variety of features and tissues may be demarked. Further, a wide variety of colors could be used, for example and without limitation, red lines could be generated to demark arteries. This is one of several potential uses of false color to facilitate medical personnel understanding of complex anatomy. Selection of whether to apply false color and to which types of tissue would be via a controller at the discretion of the medical personnel viewing the images. Voxels associated with the vein may be selected based on radiodensity or some other basis.

Some implementations may include showing the volume subtended by a cursor during review. This would permit, for example, an opportunity for the radiologist to ensure a thorough examination had been conducted and see if any regions had been missed. In some implementations, the techniques could include designating a volume of interest designated by a colored cursor for subsequent review. For medical images captured over time following an injection of any contrast material, color may be used to indicate presence and flow of the contrast material over time. Options include: combining the traces from the multiple images to show the blood vessel structure through which the contrast material moved; providing, at direction of the radiologist, time tags at point(s) of furthest movement of contrast material along each of the blood vessel's paths at each time interval; highlighting by color any connected blood vessels wherein no contrast has flowed as a potential indicator of blockage; and calculating, at direction of the radiologist, the volume of blood by time period for designated blood vessel(s) and display. In some implementations, the techniques could include for cases wherein there have been multiple sets of medical images taken over different time periods and for which a 3D volume of a tissue mass of interest has been recorded, providing the following: registration of the two (or more) volumes using the same metric system; superimposing the volumes and highlight by color (or other means such as flashing) the volumetric differences; and providing a histogram of volume of tissue of interest to quantify changes in size of the different tissue(s) within the cursor at the different times of imaging.

Referring to FIG. 5, another aspect of voxel adjustments based on radiodensity is enhanced voxel discrimination. The illustrated table 500 includes multipliers that enhance discrimination between voxels having near, but different, radiodensity and grayscale values. Voxels with Hounsfeld units of measure 25 (and associated grayscale) are multiplied by 1.2; voxels with Houndsfeld units of 30 (and associated grayscale) are multiplied by 1.5; voxels with Houndsfeld units of 35 (and associated grayscale) are multiplied by 2.0. Any of a wide variety of mathematical adjustments could be used, e.g. the table could be additive instead of multiplicative. Variations may include application of linear or non-linear functions. For example, the linear function (mX+b) could have the variable 'm' (i.e., slope) adjusted from a low slope to a higher slope. The non-linear function could be parabolic ($aX^2+bX+c$) (or other) where X would be the original grayscale. For other implementations, there could be a step increase. This is one of several ways to increase the ability to visually perceive small differences in radiodensity by adjusting the corresponding grayscale values, thereby improving visualization of the anatomy.

The mathematical adjustments may be temporally adjusted in response to controller-entered commands. The illustrated example includes three temporal multiplier adjustments that are iterated. In some implementations, if filtering results in display of a fraction/percent of the voxels, then the display could alternate display of voxels not currently to be displayed at selected time intervals. In some implementations, color could be added, such as rainbow, to particular ranges to enhance visibility.

Figure 6:
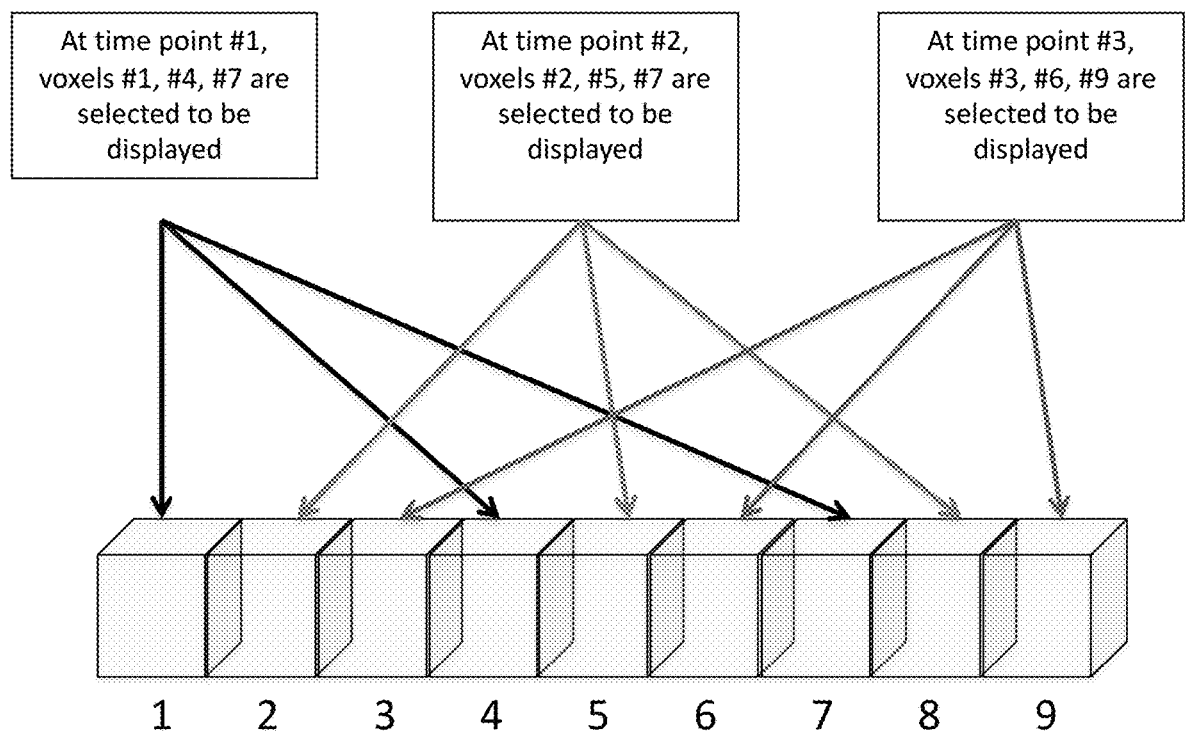
FIG. 6 illustrates aspects of filtering in greater detail.

FIG. 6 illustrates aspects of filtering in greater detail. In the illustrated example the filter is configured to select ⅓rd of the voxels for display at a given time. Specifically, every third voxel in a row of nine voxels numbered 1 through 9 is selected. Further, the filter temporally adjusts which ⅓rd of the voxels is selected for display at time points #1, #2, and #3 such that different sets of voxels are selected for display at different points in time. It may be advantageous to display only a portion of the voxels that represent a particular feature or tissue, e.g., air or fat. In the illustrated example only ⅓rd of the voxels of a certain radiodensity, and thus grayscale value, are shown at any one time. This option could also alternate which ⅓rd would be displayed over time. Note that the ⅓rd would not be a fixed fraction but one that was selectable.

Figure 7:
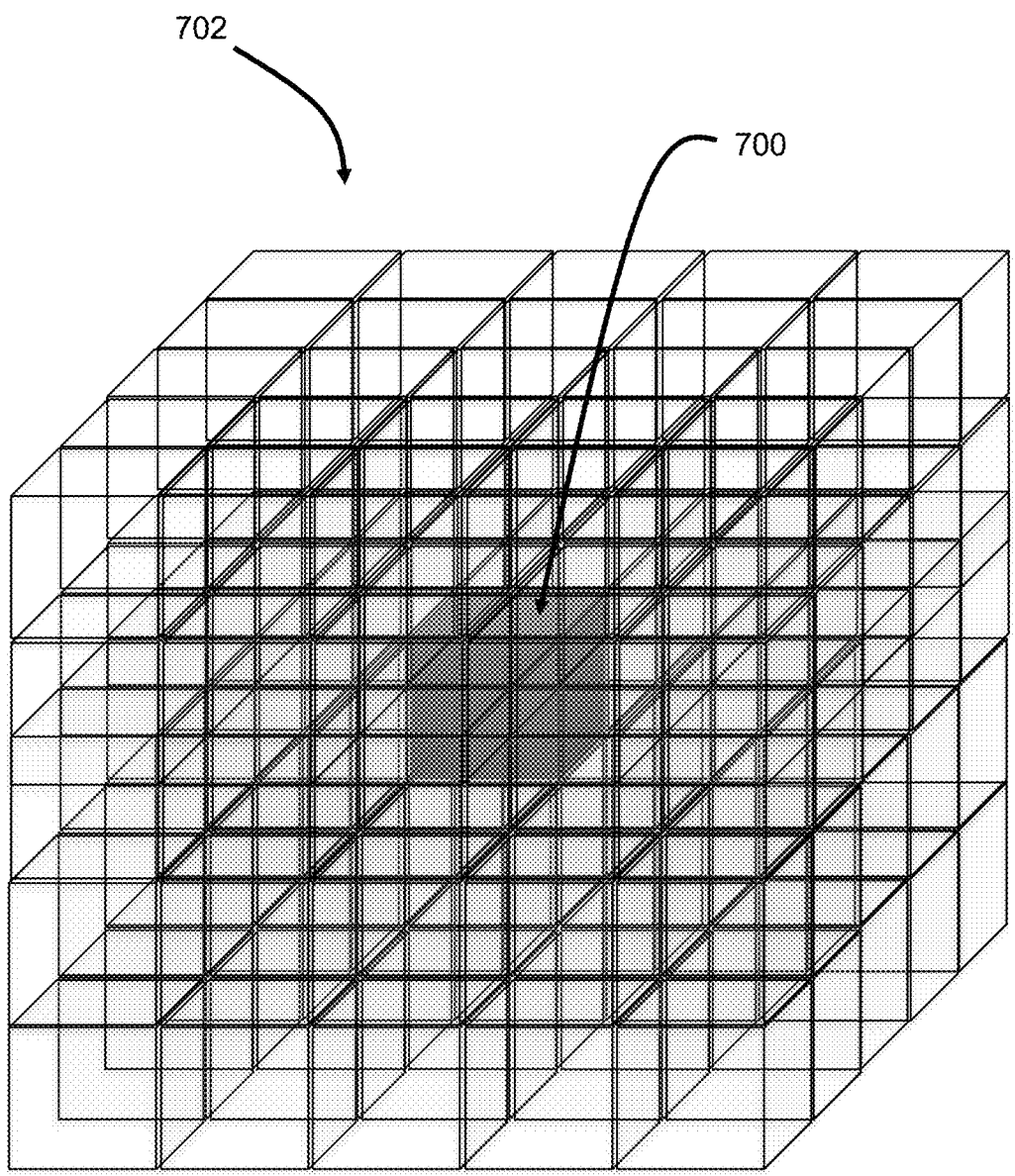
FIG. 7 illustrates an aspect of segmentation in which a voxel is classified based on the type of tissue of its nearest neighbor voxels.

FIG. 7 illustrates an aspect of segmentation in greater detail. In the illustrated example the tissue type of a voxel 700 under consideration is classified based on the tissue type of nearest neighbor voxels in a matrix. Although a 5×5×5 matrix 702 is shown, matrices of other sizes may be used, or adjacent voxels may be considered as nearest neighbors. Moreover, the set or matrix of voxels is not necessarily arranged in a cube. The 124 nearest neighbor voxels in the 5×5×5 matrix 702 are already classified with the same tissue type, so voxel 700 is likewise classified. Selection and configuration of segmentation algorithms would be via a controller at the discretion of the medical personnel viewing the images.

Figure 8A:
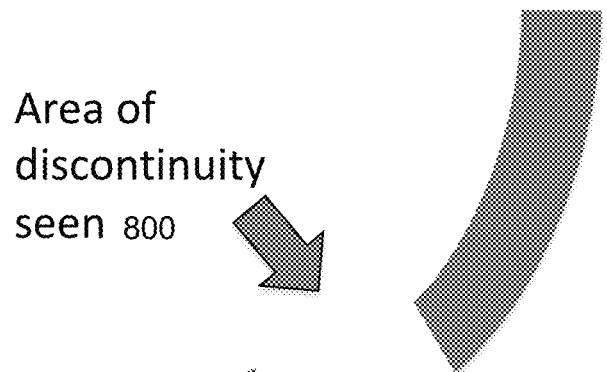
FIGS. 8A and 8B illustrate aspects of advanced segmentation wherein gaps in a vascular structure are filled.
Figure 8B:
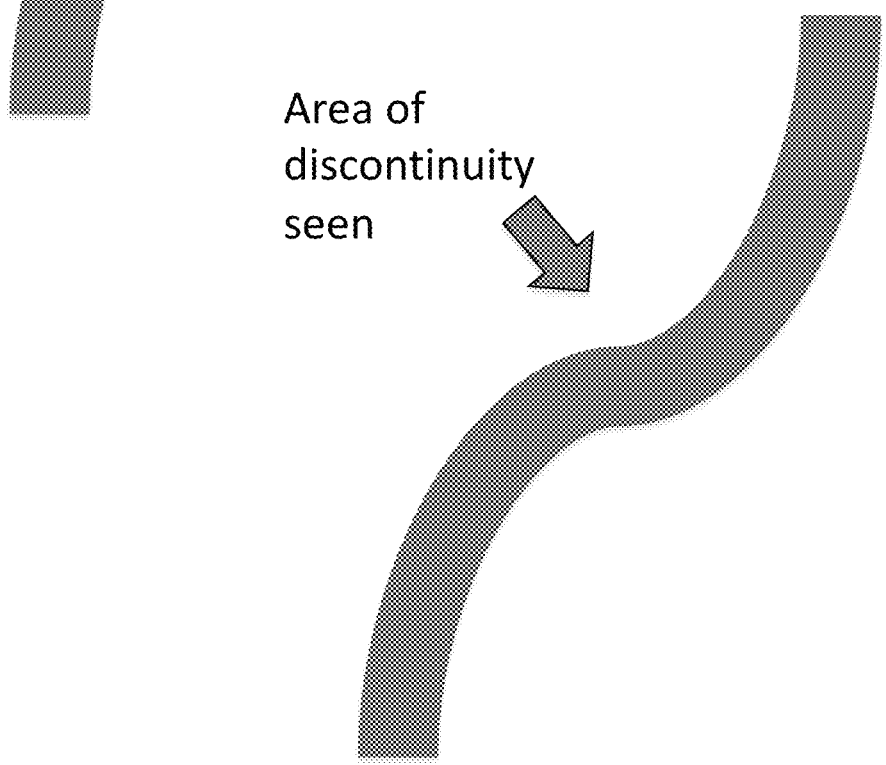

FIGS. 8A and 8B illustrate another aspect of segmentation. In the illustrated example, a gap 800 in a vascular structure is filled. There can be instances where a portion of certain connected tissue is not properly segmented when 2D algorithms are applied to 3D medical images. Vascular structure presents key challenges due to its curved nature within the body; it does not necessarily conform with a 3D grid structure. Advanced segmentation algorithms can be applied to grow the vascular structure from what is shown in FIG. 8A to what is shown in FIG. 8B. Selection of whether to apply advanced segmentation algorithms would be via a controller at the discretion of the medical personnel viewing the images.

Figure 9:
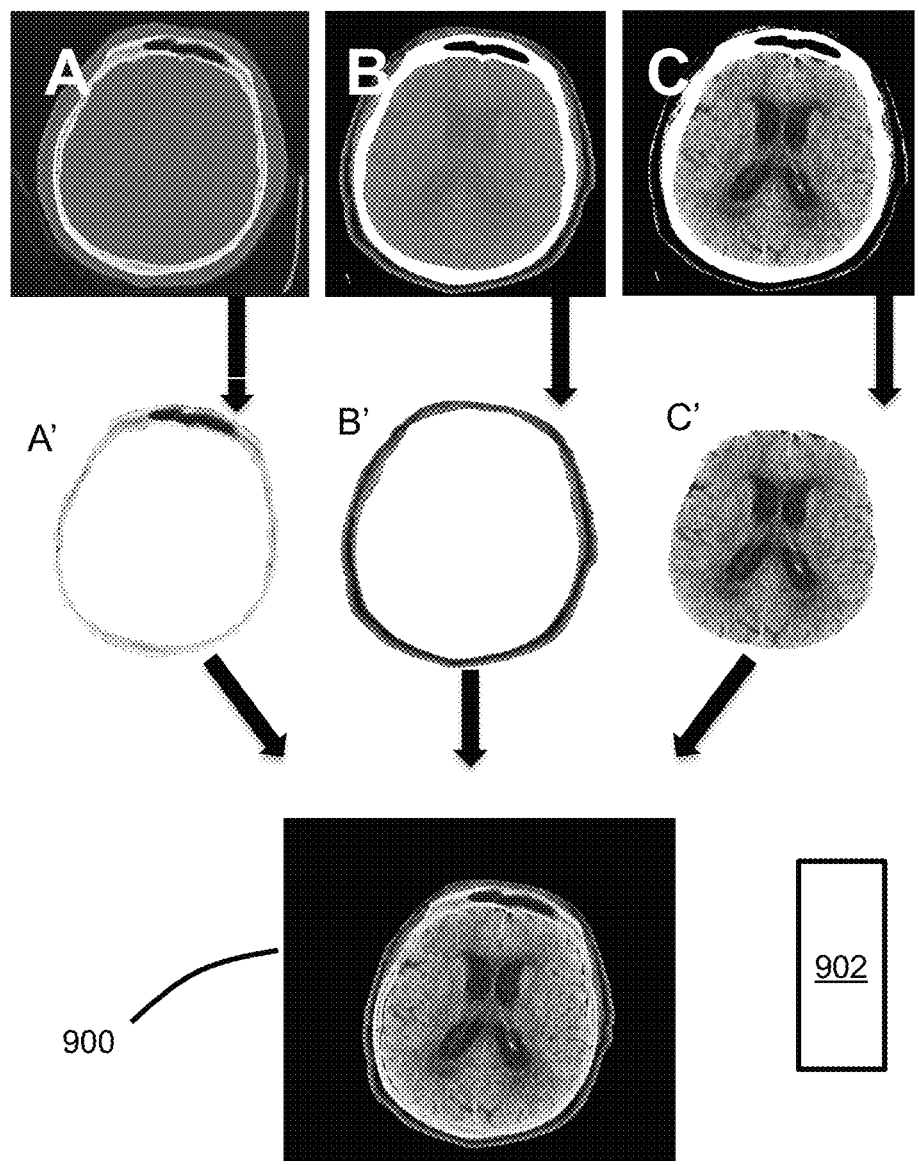
FIG. 9 illustrates use of controller-entered commands to process and combine three axial CT images of the head using the described image processing techniques.

FIG. 9 illustrates use of controller-entered commands and image processing logic to generate three axial CT images of the head and combine features extracted therefrom to generate a composite image. Images A, B, and C are generated with any combination of the image processing techniques described above. Bone algorithm image A demonstrates optimal visualization of the calvarium. Grayscale level adjustments based on radiodensity have been configured to optimize visualization of the cancellous bone within the calvarium (window level of 360 and window width of 3400). A side-effect is poor visualization of the scalp and almost no detail of the brain. The brain tissue cannot even be distinguished from the cerebrospinal fluid (CSF). Soft tissue algorithm image B is generated from the same raw image data by grayscale level adjustments based on radiodensity to optimize visualization of the scalp (window level of 40 and window width of 350). Soft tissue algorithm image C is generated from the same raw image data by grayscale level adjustments based on radiodensity to optimize visualization of the brain (window level of 30 and window width of 100).

The features of interest that have been visually optimized in images A, B, and C may be selected and extracted to generate a corresponding set of extracted feature images A', B', and C'. The extracted feature images may then be combined to generate a composite image 900. In the illustrated example, each extracted feature image includes unique tissue or tissues within the set of extracted feature images so there is no overlap when the three extracted feature images are combined to generate the composite image that represents all tissues. However, overlapping voxels having different values could be resolved algorithmically. Advantageously, the image processing steps are efficiently implemented in response to controller-entered commands based on a visual/graphical interface, e.g. via the VR headset.

Another aspect of visualization is the capability to combine findings with structured reporting. In some implementations, this could include displaying a list 902 of items which could be digitally marked by the radiologist using the 3D controller. The list of items could be unique to each item on the radiologist review checklist. In some implementations, the list presented on the 3D head display unit or the 2D display. Items which had been digitally marked would be automatically included in the report. In some implementations, a list of frequently used phrases for each item on the radiologist review checklist could be displayed at the direction of the radiologist who could then digitally mark any of the relevant phrases. Phrases which had been digitally marked would be automatically included in the report.

Another aspect of visualization is changing viewing perspective. In some implementations, a selected image, volume, feature, tissue, voxel set, or voxel is automatically re-centered or re-located to enhance radiologist orientation of location within the volume being examined. Examples of auto re-location include, but are not limited to, the following: the viewing perspective could be re-located to an initial viewing point of an image set; and the viewing perspective could be re-located to additional point(s) designated by the radiologist during the course of the examination. In some implementations, the cursor color or shape could correspond to pre-selected conditions, for example, but not limited to: review checklist items; types of tissue of concern; and regions for collaboration between medical personnel.

Another aspect of visualization is the capability to switch between various dimensional views (i.e., change back and forth between viewing 3D volume and 2D slices). In some implementations, selection of the 2D slice could be based on, but not limited to: the center point of the 3D cursor; a point within the 3D volume designated by the radiologist. In some implementations, the 3D controller to scroll through the slices.

Figure 10:
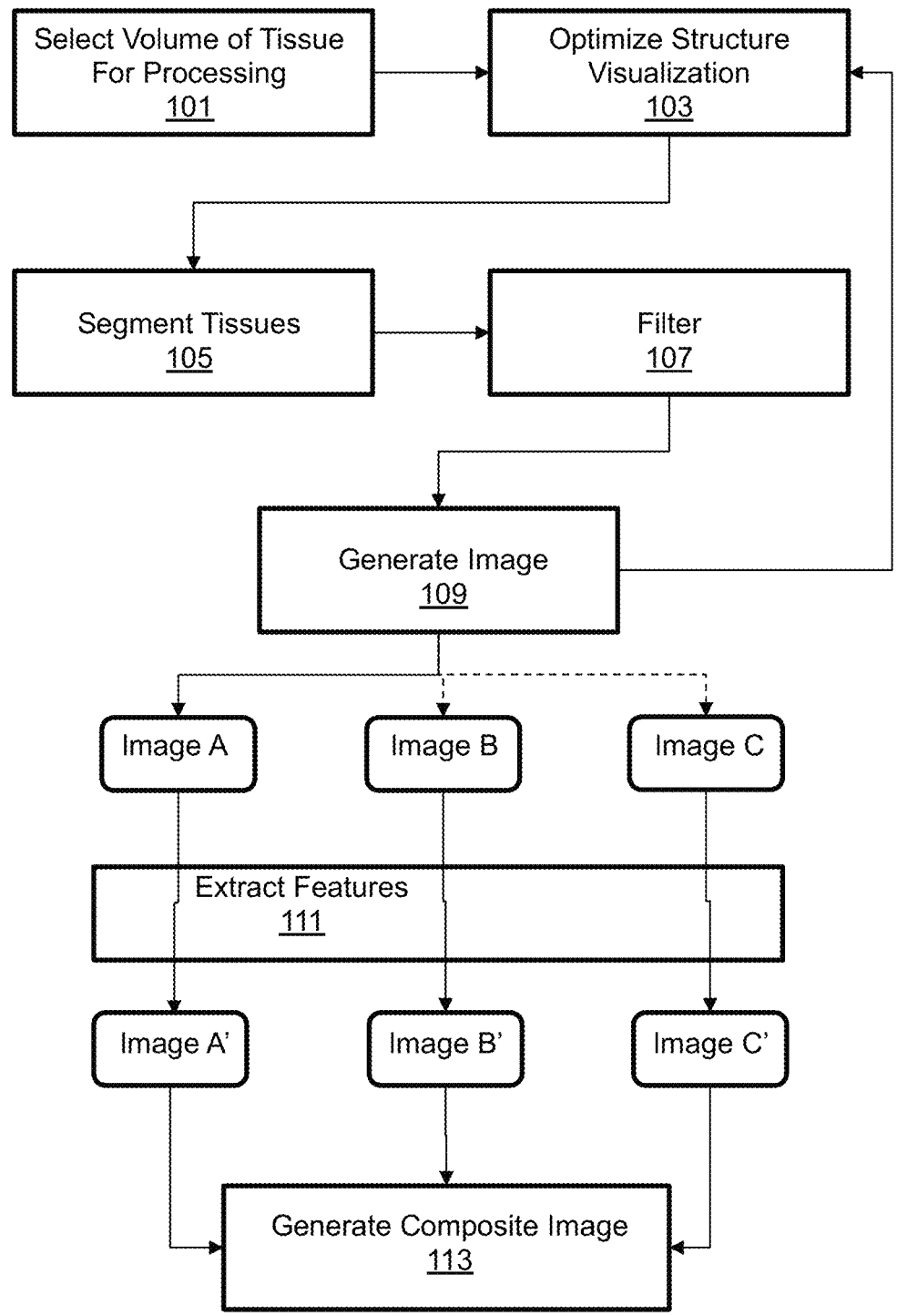
FIG. 10 is a flow diagram of procedural steps in accordance with aspects of the invention.

FIG. 10 illustrates a method in accordance with aspects of the invention. Procedurally, a volume of tissue within the body may initially be selected for processing in step 101. Raw scan data is retrieved for the selected volume, and one or more processing algorithms may be selected, configured, and applied. For example, one or more voxels adjustments based on radiodensity may be implemented to enhance one or more features of interest and optimize structure visualization as shown in step 103. Further, one or more segmentation algorithms may be selected, configured, and applied to segment tissues as shown in step 105. Further, filters may be selected, configured, and applied as shown in step 107. An image A is then generated based on the processing algorithms as shown in step 109. Steps 103, 105, 107, and 109 may be iterated for the selected volume any number of times to generate more images, e.g. images that enhance different tissues or features within the selected volume. In the illustrated example image B and image C are generated with different processing algorithms and/or configuration settings. The enhanced tissues or features from the images A, B, C are then extracted as shown in step 111, resulting in extracted feature images A', B', and C'. The extracted feature images are then combined to generate a composite image as shown in step 113.

FIG. 11 illustrates optimal viewing settings for 2D imaging and for 3D imaging. A list of the optimal viewing settings is generated for each item in an image. In 1100, two examples are provided within an image are shown along with the optimal viewing settings during 2D slice-by-slice viewing per user preference. In the first example, the liver is viewed on a CT scan with conventional settings. The liver is shaded in gray shades and with particular group (e.g., specified range is designed to catch hypervascular tumors, necrotic tumors, etc.) in color with option for voxel manipulation. All other tissues are turned to dark gray shades. In the second example, the breast is viewed during a digital breast tomosynthesis examination. Breast glandular parenchyma in gray shades with particular s (e.g., specified range) designed to catch microcalcifications) shown in red. Additionally, as discussed elsewhere in this disclosure and in U.S. patent application Ser. No. 16/195,251, INTERACTIVE VOXEL MANIPULATION STRATEGIES IN VOLUMETRIC MEDICAL IMAGING ENABLES VIRTUAL MOTION, DEFORMABLE TISSUE, AND VIRTUAL RADIOLOGICAL DISSECTION, the voxels are can be manipulated. This can be utilized to improve visualization. In 1102, a first visual representation adjustment logic is applied to the entire image, such as performing a liver window wherein voxels whose Hounsfield units are less than −45 are black, voxels whose Hounsfield units are more than +105 are white and voxels whose Hounsfield units are shades of gray. Additionally, this embodiment also enables a second visual representation adjustment logic to be applied to voxels whose range is in between +80 to +105. This "group" helps the user pick out hypervascular liver metastases whose density is typically in the range of +80 to +105, as shown in red. The preferred embodiment is for the technique to be performed in conjunction with segmentation (e.g., segment the organ and then apply the described visual representation adjustment logic); however, this would not necessarily be required. Additionally, this embodiment also enables a third (or more) visual representation adjustment logic to be applied, such as coloring a group of voxels in the range of +20 to +30 would be in the range of necrotic liver tumors the color green. In 1104, two items within an image are shown along with the optimal viewing settings during 3D extended reality volume-by-volume viewing per user preference. For example, prioritized volume rendering of HU ranges is utilized within the liver and displayed in a dynamic fashion to make more subtle (but dangerous lesions) easier to detect. This is described in more detail in U.S. Provisional Patent Application No. 62/846,770, A method of prioritized volume rendering to improve visualization of prioritized items within a 3D volume. Additionally, the voxels that subtend the liver are divided into groups based on their property (e.g., Hounsfield Unit). For example, assume that voxels that subtend the liver have Hounsfield of 30-60. These can be divided into 3 groups (e.g., upper range of 50-60 HU, a middle range of 40-50 HU, and a lower range of 30-40 HU) wherein at three different time points one of the groups has enhanced visualization (e.g., color schemes) and the other two groups have diminished visualization (e.g., dark gray scale). This process wherein voxels are divided into groups and then visualization enhanced or diminished improves detection of subtle lesions. For example, the liver parenchyma should appear homogeneous on each of the 3 phases. Peering into the liver at each phase can help a certain masses that tend to fall in a band stand out from the rest of the liver parenchyma. All other tissues are made more translucent (e.g., sparse sampling) or are filtered. For example, for prioritized volume rendering is performed wherein voxels with higher priority and be displayed. All other tissues are made more translucent (e.g., via sparse sampling) or are filtered. This processed may be performed in accordance with a checklist.

Figure 12:
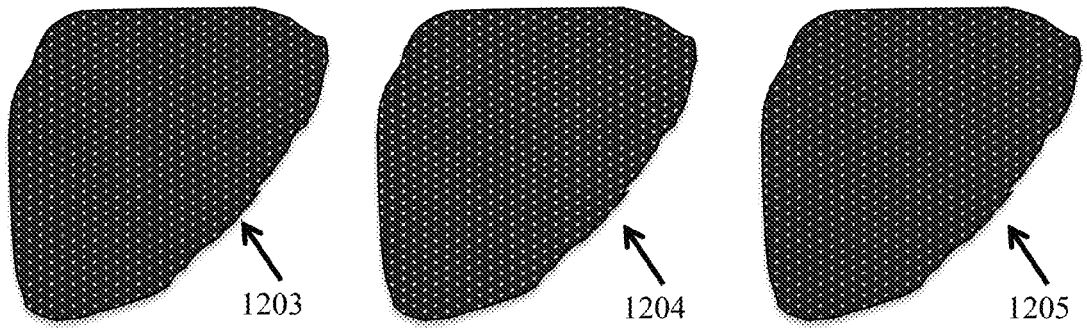
FIG. 12 illustrates utilization of range-based grouping as a display settings.

FIG. 12 illustrates utilization of range-based grouping as a display settings. Certain voxels within the liver having improved visualization through group-wise visual representation adjustment logic. In this embodiment, voxels are first divided into groups and then visual representation adjustment logic is applied wherein at least one group of voxels has a different visual representation adjustment logic as compared to at least one other group of voxels. For example, consider the liver. Assume that the liver is segmented and inside the segmented liver are voxels with Hounsfield Units ranging between 30-60. This embodiment improves visualization and inspection of liver (HU of 30-60) by dividing the voxels into groups (e.g., upper range of 50-60 HU, a middle range of 40-50 HU, and a lower range of 30-40 HU). Then, at three different time points one of the groups has enhanced visualization (e.g., rainbow color, midgray to white shades only, etc.) and the other two groups have diminished visualization (e.g., dark grayscale). Through user inputs, the first group (e.g., upper group with range of 50-60 HU) would be optimally displayed during the first time period and the middle and lower groups would have diminished visualization. In this illustration, the optimized group during the first time period has HU of 50-60 and is assigned yellow shades and the remainder of the groups (HU 30-50) have diminished visualization and are assigned dark gray to black shades. Then, through user inputs (or via automated process) the second group (e.g., middle group with range of 40-50 HU) would be optimally displayed during the second time period and the highest group (e.g., HU 50-60) and lowest group (e.g., HU 30-40) would have diminished visualization. In this illustration, the optimized group during the second time period has HU of 40-50 and is assigned light green shades and the remainder of the groups (HU 30-40 and HU 50-60) have diminished visualization and are assigned dark gray to black shades. Finally, through user inputs (or via an automated process) the third group (e.g., lower group with range of 30-40 HU) would have optimized visualization and the upper (e.g., HU 50-60) and middle groups (e.g., HU 40-50) would have diminished visualization. In this illustration, the optimized group during the third time period has HU of 30-40 and is assigned light purple shades and the remainder of the groups (HU 40-60) have diminished visualization and are assigned dark gray to black shades. This process of changing the appearance could be performed on 2D slices on a radiology monitor. Alternatively, it could be performed on 3D volumes using augmented reality, mixed reality or virtual reality displays and groups selected for diminished visualization would be preferentially filtered. Given that the groups that are filtered change over time (e.g., per user preference), then this filtering would be dynamic. This process wherein voxels are divided into groups and then visualization enhanced or diminished improves detection of subtle lesions. 1202 illustrates a text box, which states range grouping prior to implementing visual representation adjustment logic. 1203 is the liver at a first time point. 1204 is the liver at a second time point. 1205 is the liver at a third time point. The text box 1206 illustrates at time point 1 that the optimized band has Hounsfield Units of 50-60 and is shown in yellow shades and the diminished band has Hounsfield Units of 30-50 and is shown in dark gray to black shades. The text box 1207 illustrates at time point 2 that the optimized band has Hounsfield Units of 40-50 and is shown in light green shades and the diminished band has Hounsfield Units of 30-40 and 50-60 and is shown in dark gray to black shades. The text box 1208 illustrates at time point 3 that the optimized band has Hounsfield Units of 30-40 and is shown in light purple shades and the diminished band has Hounsfield Units of 40-60 and is shown in dark gray to black shades.

FIG. 13 illustrates generating multiple simultaneous window/level settings for viewing of 3D datasets. Step 1300 illustrates performing a first windowing and leveling setting. Step 1301 illustrates performing segmentation of organs. 1302 illustrates generating a list of data that might be normal vs. abnormal. 1303 illustrates applying a first visual representation adjustment logic to standard window/level setting to voxels that are thought to be normal. 1304 illustrates applying second visual representation adjustment logic (false color) that are thought to be abnormal. 1305 illustrates an option to apply additional (third or more) visual representation adjustment logic to additional ranges.

Figure 14:
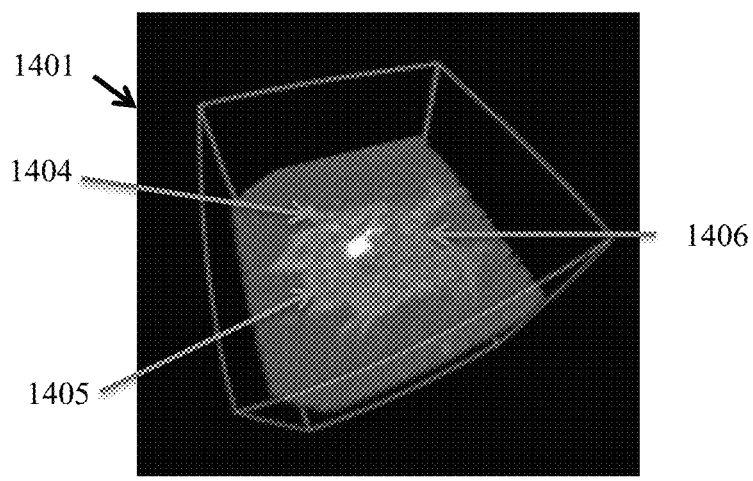
FIG. 14 illustrates challenges faced of visualizing certain ranges without multiple windowing.

FIG. 14 illustrates challenges faced of visualizing certain ranges without multiple windowing. 1400 is a text box which provides description of the dataset. The following image is a sub-volume of a CT scan of the breast, inside of a volume-subtending 3D cursor. The sub-volume is comprised of approximately 100×100×100 or 1 million voxels. 1401 illustrates an image of the sub-volume. 1404 illustrates a first voxel that blends in with the rest of the gray shades. 1405 illustrates a second voxel that blends in with the rest of the gray shades. 1406 illustrates a third voxel that blends in with the rest of the gray shades. 1407 illustrates a text box, which states an embodiment of this patent is to be able to improve imaging by making some voxels (e.g., voxels with Hounsfield Unit range 70-75) to have a "special" visibility.

FIG. 15 illustrates with overcoming challenges in visualizing certain ranges when using viewing multiple windowing. 1500 is a text box. Step #1 is to divide the voxels into ranges. The first range will include all voxels with Hounsfield Units between 70 and 75. Assume that there are 3 voxels in this first band. The second range will include all other voxels in the volume. Assuming the 100×100×100 matrix, that would equal 999,997 voxels in this second band. Step #2 is to assign visual representation adjustment logic to the first band of 3 voxels (e.g., color all voxels in this band yellow). Step #3 is to assign a different visual representation adjustment logic to the second band of 999,997 voxels (e.g., color voxels in this band varying shades of gray based on Hounsfield Units and conventional windowing and leveling settings. 1501 shows that the first voxel has been re-assigned a yellow color, from its previous gray-scale appearance. 1502 shows that the second voxel has been re-assigned a yellow color, from its previous gray-scale appearance. 1503 shows that the third voxel has been re-assigned a yellow color, from its previous gray-scale appearance.

FIG. 16 illustrates a method of improving image quality. Step 1600 is to perform imaging examination. Step 1601 is to load an original imaging dataset of a patient wherein each pixel or voxel within the imaging dataset has an associated data unit. Step 1602 is to perform segmentation of the imaging dataset (e.g., segment a phantom, segment the anatomy, segment structures outside of the patient, etc.).

Step 1603 is to select a first segmented structure for analysis. Step 1604 is to perform at least one measurement of the data unit(s) within the first segmented structure. Step 1605 is to determine the expected value(s) of the data unit(s) within the first segmented structure. Step 1606 is to determine at least one correction factor based on the difference between the at least one measurement(s) of the data unit(s) within the first segmented structure and the expected value(s) of the data unit(s) within the first segmented structure wherein the corrective factor can be applied to a second segmented structure to cause improved image quality. Step 1607 is to input the at least one corrective factor to modify the data units of at least one of the group comprising the first segmented structure and the second segmented structure in the original imaging dataset to create a modified imaging dataset wherein the modified imaging dataset has improved image quality.

Figure 17:
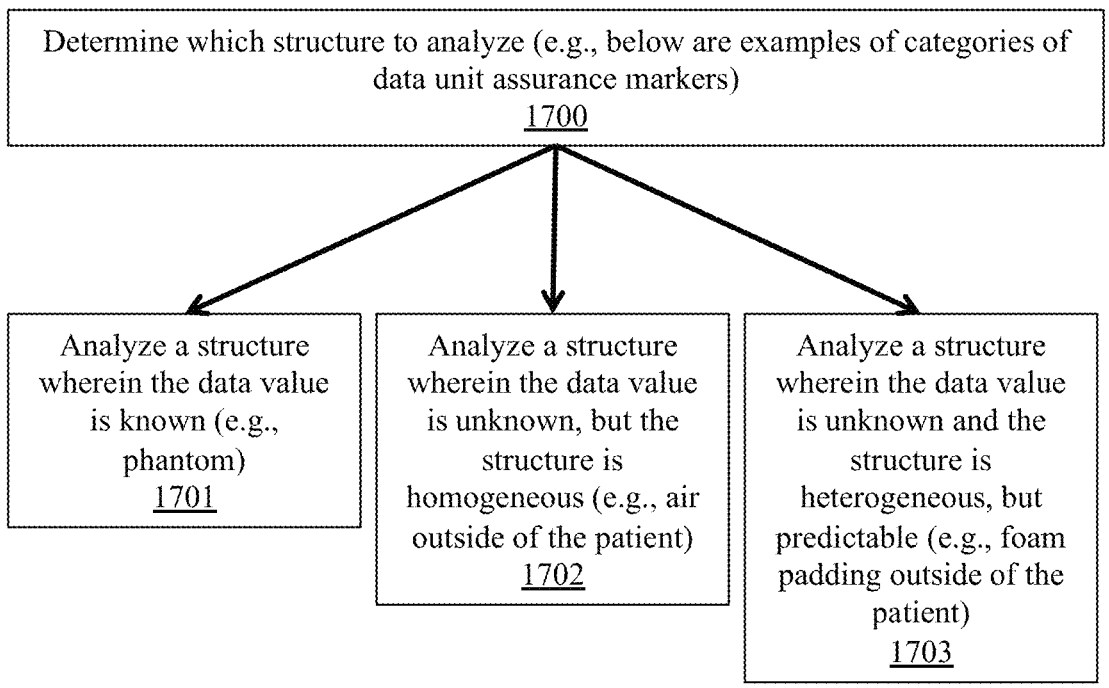
FIG. 17 illustrates a method of identifying data unit assurance markers.

FIG. 17 illustrates a method of identifying data unit assurance markers. This also provides identifying which structure can be analyzed. Step 1700 is to determine which structure to analyze (e.g., below are examples of categories of data unit assurance markers). A first suggested option 1701 is to analyze a structure wherein the data value is known (e.g., phantom). A second suggested option 1702 is to analyze a structure wherein the data value is unknown, but the structure is homogeneous (e.g., air outside of the patient). A third suggested option 1703 is to analyze a structure wherein the data value is unknown and the structure is heterogeneous, but predictable (e.g., foam padding outside of the patient).

Figure 18:
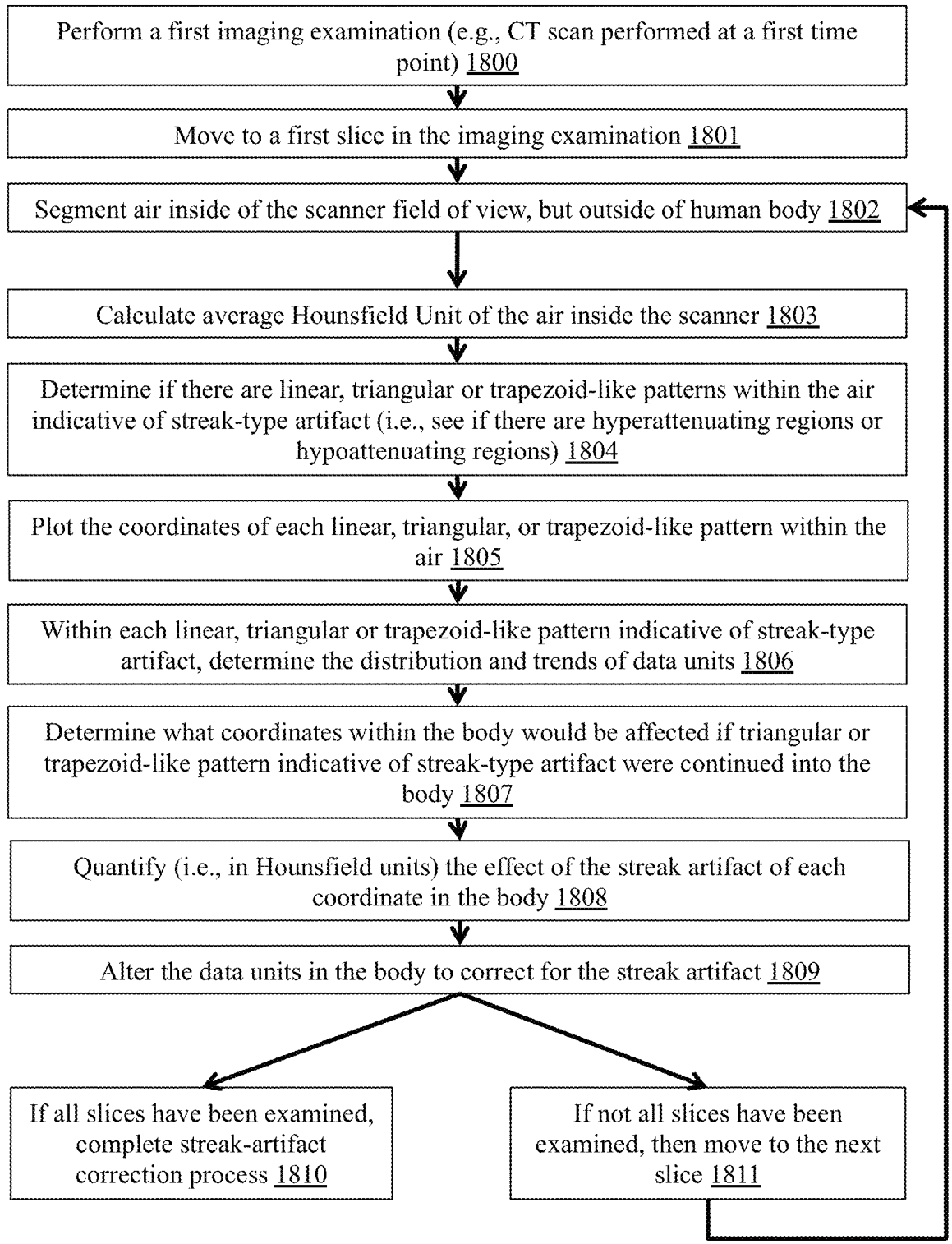
FIG. 18 illustrates an example of analyzing density of air outside of the patient's body to correct for artifacts within the patient's body.

FIG. 18 illustrates an example of analyzing density of air outside of the patient's body to correct for artifacts within the patient's body. Step 1800 is to perform a first imaging examination (e.g., CT scan performed at a first time point). Step 1801 is to move to a first slice in the imaging examination. Step 1802 is to segment air inside of the scanner field of view, but outside of human body. Step 1803 is to calculate average Hounsfield Unit of the air inside the scanner. Step 1804 is to determine if there are linear, triangular or trapezoid-like patterns within the air indicative of streak-type artifact (i.e., see if there are hyperattenuating regions or hypoattenuating regions). Step 1805 is to plot the coordinates of each linear, triangular, or trapezoid-like pattern within the air. Step 1806 is to within each linear, triangular or trapezoid-like pattern indicative of streak-type artifact, determine the distribution and trends of data units. Step 1807 is to determine what coordinates within the body would be affected if triangular or trapezoid-like pattern indicative of streak-type artifact were continued into the body. Step 1808 is to quantify (i.e., in Hounsfield units) the effect of the streak artifact of each coordinate in the body. Step 1809 is to alter the data units in the body to correct for the streak artifact. Note that this could be done for many different types of artifact in both CT and MRI. Step 1810 is if all slices have been examined, complete streak-artifact correction process. Step 1811 is if not all slices have been examined, then move to the next slice and return to step 1802. Nested do loops and other types of software strategies can be performed to accomplish these type steps.

Figure 19A:
FIG. 19A illustrates a CT image of the head with window and level settings optimized for visualization of air.

FIG. 19A illustrates a CT image of the head with window and level settings optimized for visualization of air. Note that there are groups of high density and low density inside of the segmented air. These correspond to areas of streak artifact.

Figure 19B:
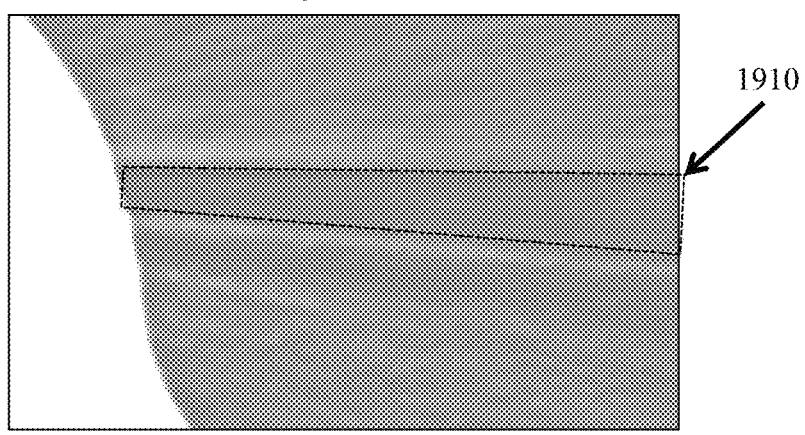
FIG. 19B illustrates a zoomed in CT image of the head with window and level settings optimized for visualization of air.

FIG. 19B illustrates a zoomed in CT image of the head with window and level settings optimized for visualization of air. Note that a trapezoid 1910 is shown in the image to denote the dark group.

Figure 19C:
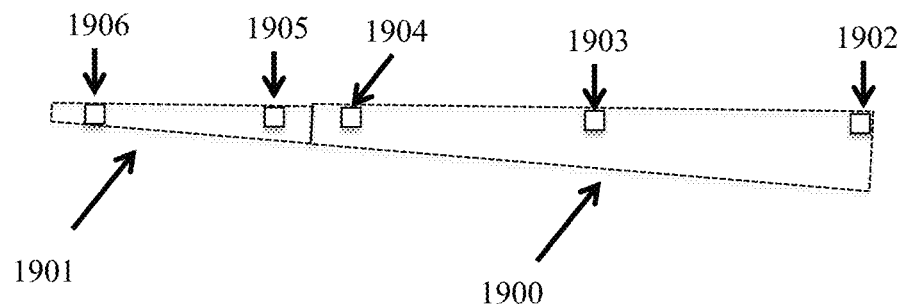
FIG. 19C illustrates a plot of voxels within the region of air, which can be used to determine the correction factor applied to voxels within the head.

FIG. 19C illustrates a plot of voxels within the region of air, which can be used to determine the correction factor applied to voxels within the head. 1901 illustrates a trapezoid containing voxels inside of the head. 1900 illustrates a trapezoid containing voxels in the air outside of the head. Voxel 1902 is shown farthest away from the scalp and has a Hounsfield Unit of −987. Voxel 1903 is mid-way from the scalp and has a Hounsfield Unit of −976. Voxel 1904 is closest to the scalp and has a Hounsfield Unit of −951. Voxel 1905 is in the superficial scalp and has a Hounsfield Unit of −103. Voxel 1906 is in the brain and has a Hounsfield Unit of 24. A correction factor is applied. Voxel 1902 is corrected to −1000. Voxel 1903 is corrected to −1000. Voxel 1904 is corrected to −1000. Voxel 1905 is corrected to −90. Voxel 1906 is corrected to 30.

Figure 20:
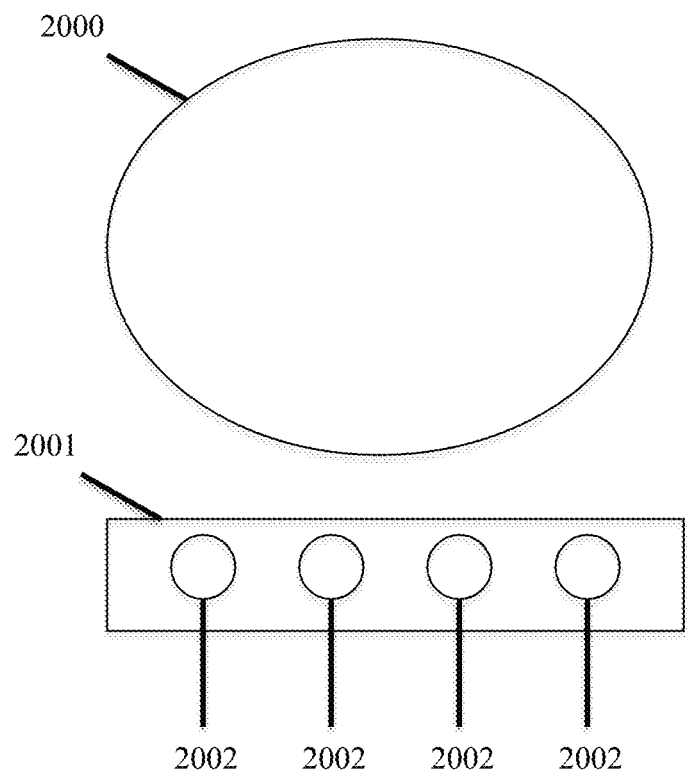
FIG. 20 illustrates an example of placing phantoms inside of a table associated with a scanner.

FIG. 20 illustrates an example of placing phantoms inside of a table associated with a scanner. The patient 2000 is shown. The table 2001 is shown. Multiple phantoms 2002 are shown. The type of phantoms used can vary greatly (e.g., designed with varying size, materials, and locations). The design may also vary based on the type of examination and the indication of the examination.

Figure 21:
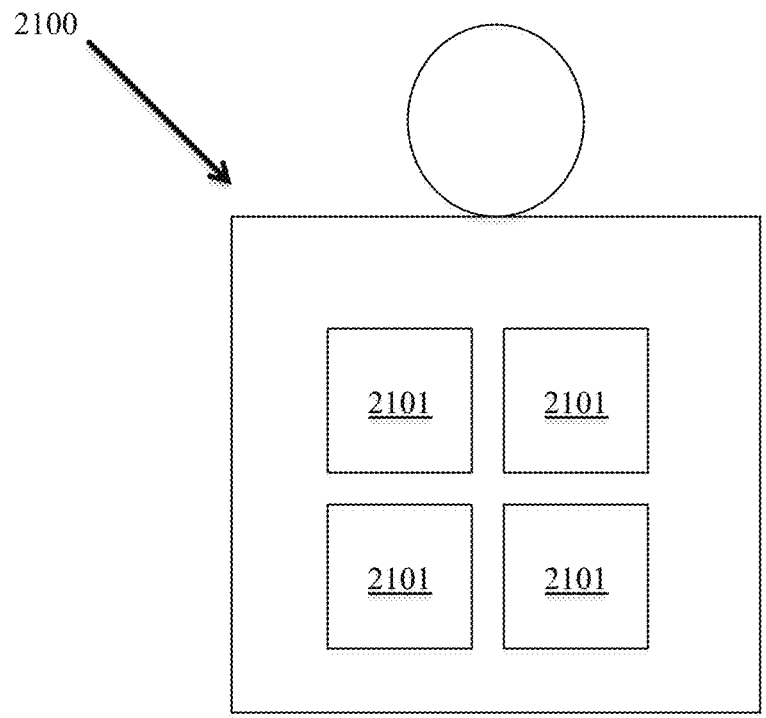
FIG. 21 illustrates an example of placing phantoms onto the patient.

FIG. 21 illustrates an example of placing phantoms onto the patient. The patient 2100 is shown. Multiple phantoms 2101 are shown on the patient. Note that the phantoms could also be inside of the patient, preferably in the form of ingested capsules wherein each capsule contains at least one substance (e.g., water, oils, etc.). This would serve as internal landmarks. Other implantable phantoms (e.g., via surgery or needle placement) could be performed for certain conditions that require precision monitoring (e.g., brain tumor signal). The implantable phantoms may also be placed onto or within a variety of surgical devices (e.g., pacemaker, port-a-cath, etc.).

Figure 22:
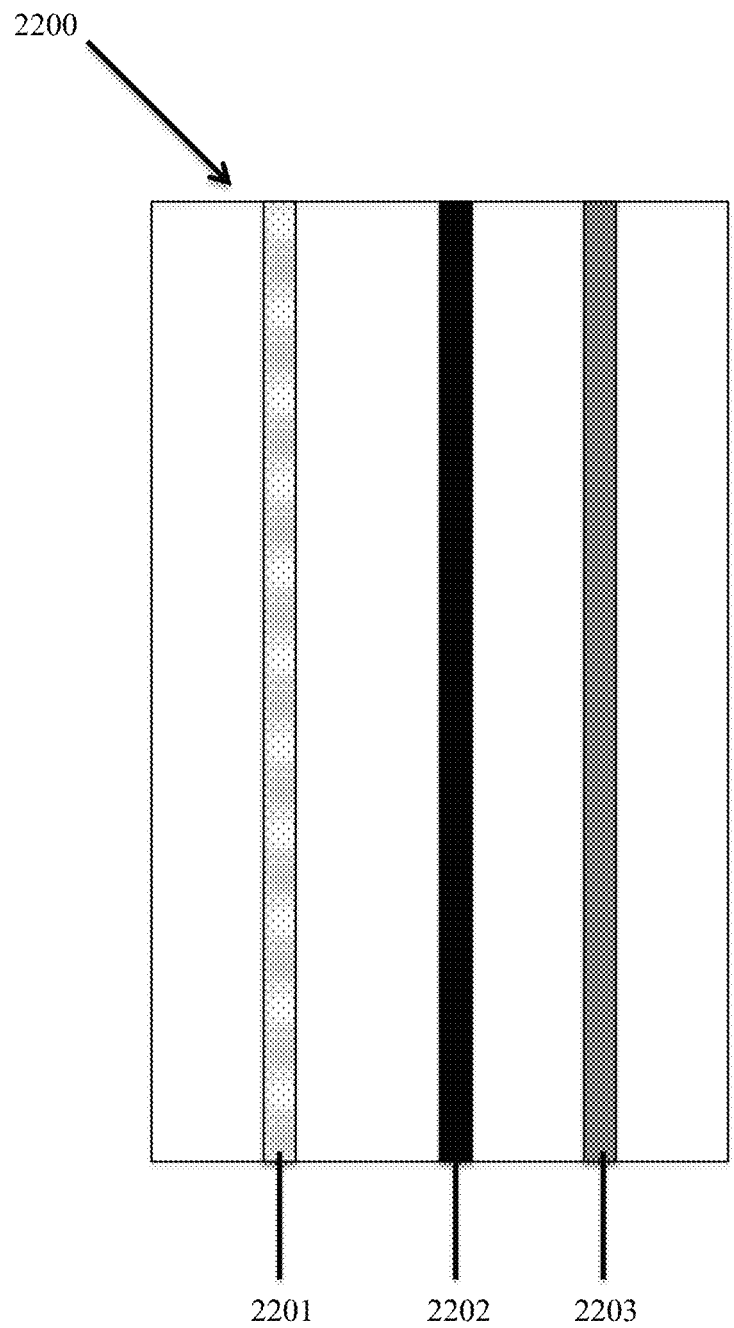
FIG. 22 illustrates an example of placing phantoms onto a blanket.

FIG. 22 illustrates an example of placing phantoms onto a blanket. The blanket 2200 is shown. A first material 2201 is shown in the blanket. A second material 2202 is shown in the blanket. A third material 2203 is shown in the blanket. This could be used to wrap the patient and improve reliability of the data units of a particular examination.

Figure 23A:
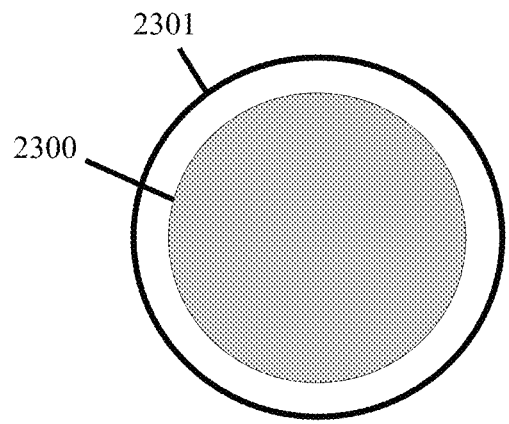
FIG. 23A illustrates a phantoms surrounding a patient in a single, circumferential layer.

FIG. 23A illustrates a phantoms surrounding a patient in a single, circumferential layer. 2300 is the patient. 2301 is the single, circumferential layer of phantoms. Based on the measured signal in the phantom, corrections to the dataset can be made.

Figure 23B:
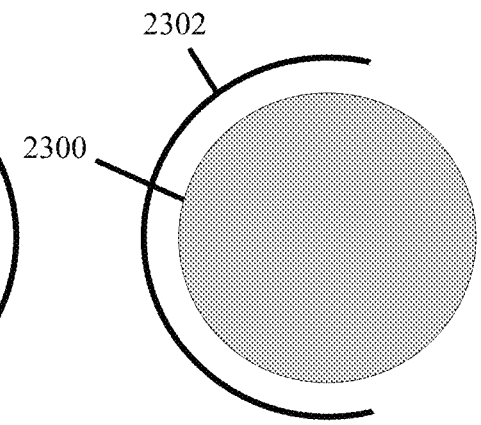
FIG. 23B illustrates a phantoms surrounding a patient in a single layer, which is not circumferential.

FIG. 23B illustrates a phantoms surrounding a patient in a single layer, which is not circumferential. 2300 is the patient. 2302 is the single, non-circumferential layer of phantoms. Based on the measured signal in the phantom, corrections to the dataset can be made.

Figure 23C:
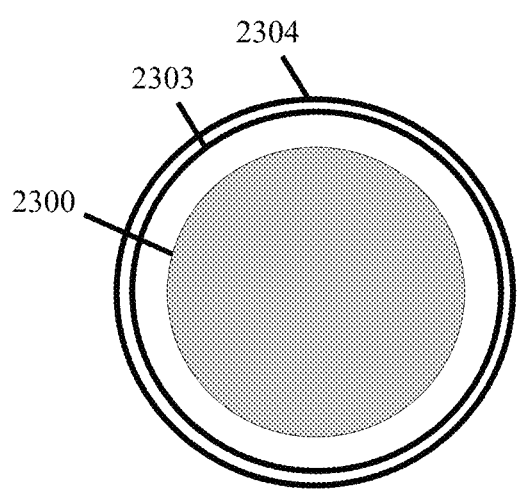
FIG. 23C illustrates a phantoms surrounding a patient multiple, circumferential layers.

FIG. 23C illustrates a phantoms surrounding a patient multiple, circumferential layers. 2300 is the patient. 2303 is the first layer of a circumferential layer of phantoms. 2304 is the second layer of a circumferential layer of phantoms. Based on the measured signal in the phantom, corrections to the dataset can be made.

Figure 23D:
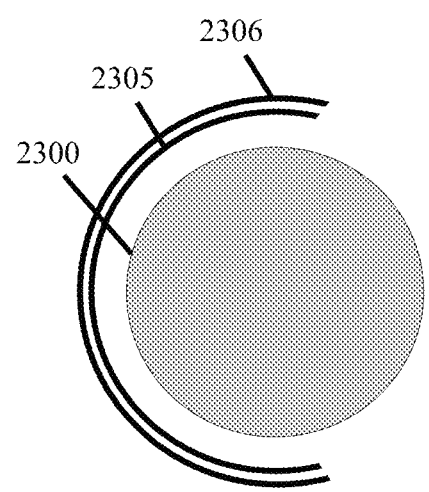
FIG. 23D illustrates a phantoms surrounding a patient in a multiple, non-circumferential layers.

FIG. 23D illustrates a phantoms surrounding a patient in a multiple, non-circumferential layers. 2303 is the first layer of a circumferential layer of phantoms. 2305 is the first layer of a non-circumferential layer of phantoms. 2306 is the second layer of a non-circumferential layer of phantoms. Based on the measured signal in the phantom, corrections to the dataset can be made. These examples are illustrative only. A wide variety of placement of phantoms could be performed in a scanner for data unit assurance purposes as described in this patent.

Figure 24:
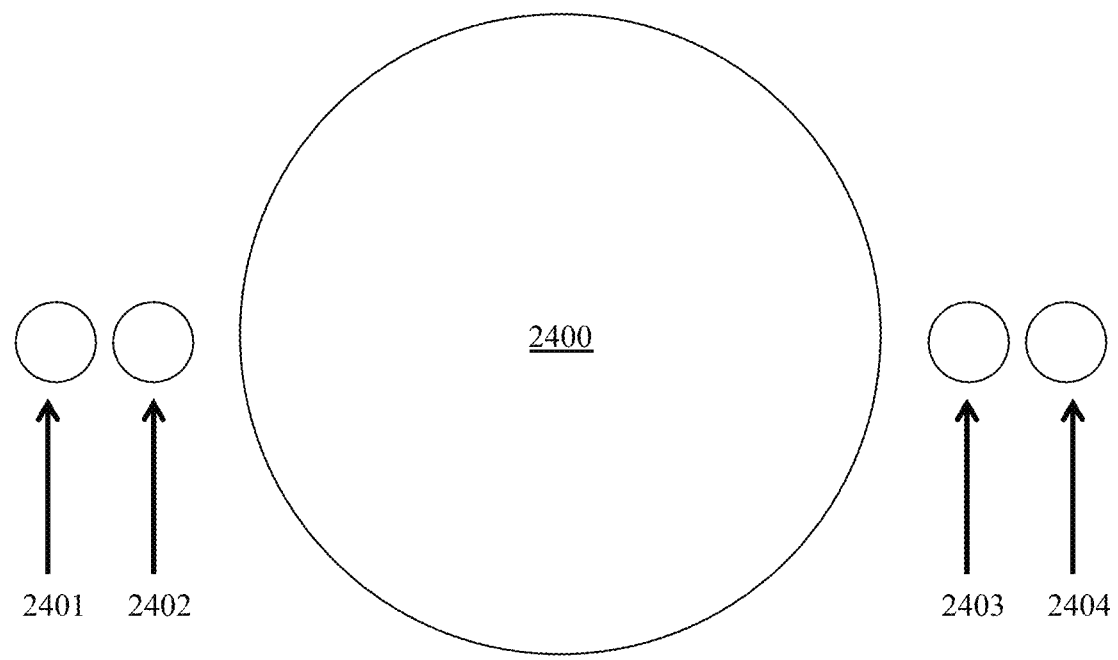
FIG. 24 illustrates multiple measurements in a radial fashion outward from the patient.

FIG. 24 illustrates multiple measurements in a radial fashion outward from the patient. This is an example of the phantom-based data unit correction. 2400 illustrates a cross-section of the patient. 2401 illustrates a first phantom, which contains only water. 2402 illustrates a second phantom, which contains only water. 2403 illustrates a third phantom, which contains only water. 2404 illustrates a fourth phantom, which contains only water. The preferred embodiment is multiple layers in the wrapping material, which allows factoring in differences in the data units over radial distance away from the patient. This provides increased accuracy.

Figure 25A:
FIG. 25A illustrates a region of streak artifact going from scalp soft tissue into the air.

FIG. 25A illustrates a region of streak artifact going from scalp soft tissue into the air. Note that the third row 2500 contains voxels measuring 40, 40, −990, −990, and −990. This third row 2500 illustrates streak artifact.

Figure 25B:
FIG. 25B illustrates the modified dataset wherein the streak artifact is corrected.

FIG. 25B illustrates the modified dataset wherein the streak artifact is corrected. Note that the third row 2501 contains voxels measuring 50, 50, −1000, −1000, and −1000. This third row 2500 illustrates correction of the streak artifact.

Figure 26:
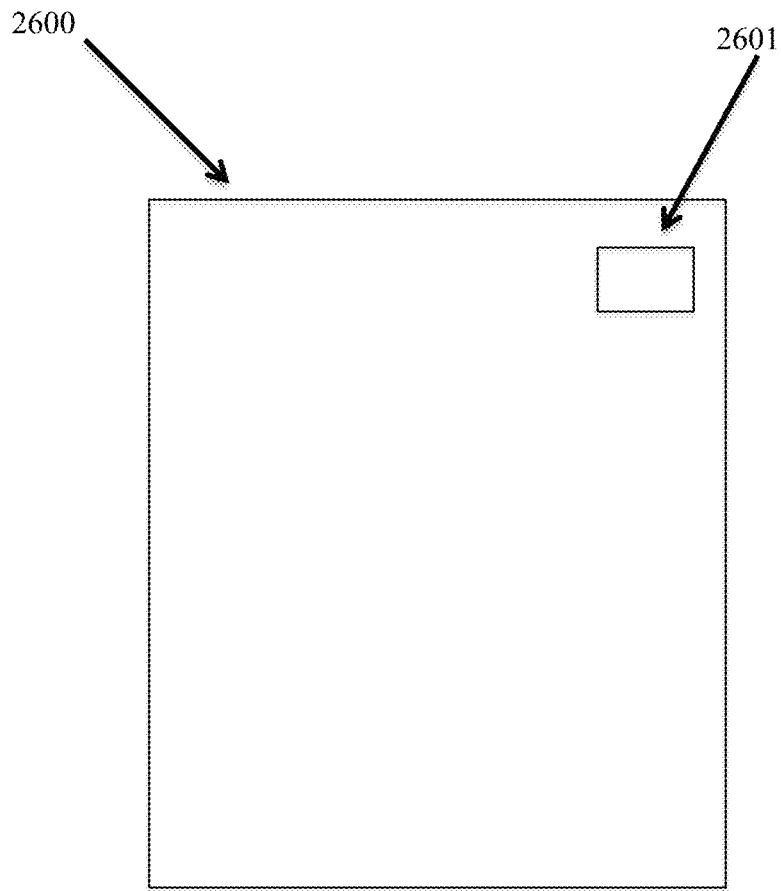
FIG. 26 illustrates an x-ray detector attached to a phantom.

FIG. 26 illustrates an x-ray detector attached to a phantom. 2600 is the x-ray detector. 2601 is the phantom. Please note that the number of phantoms, type(s) of phantoms and positions of phantoms can vary greatly.

Figure 27:
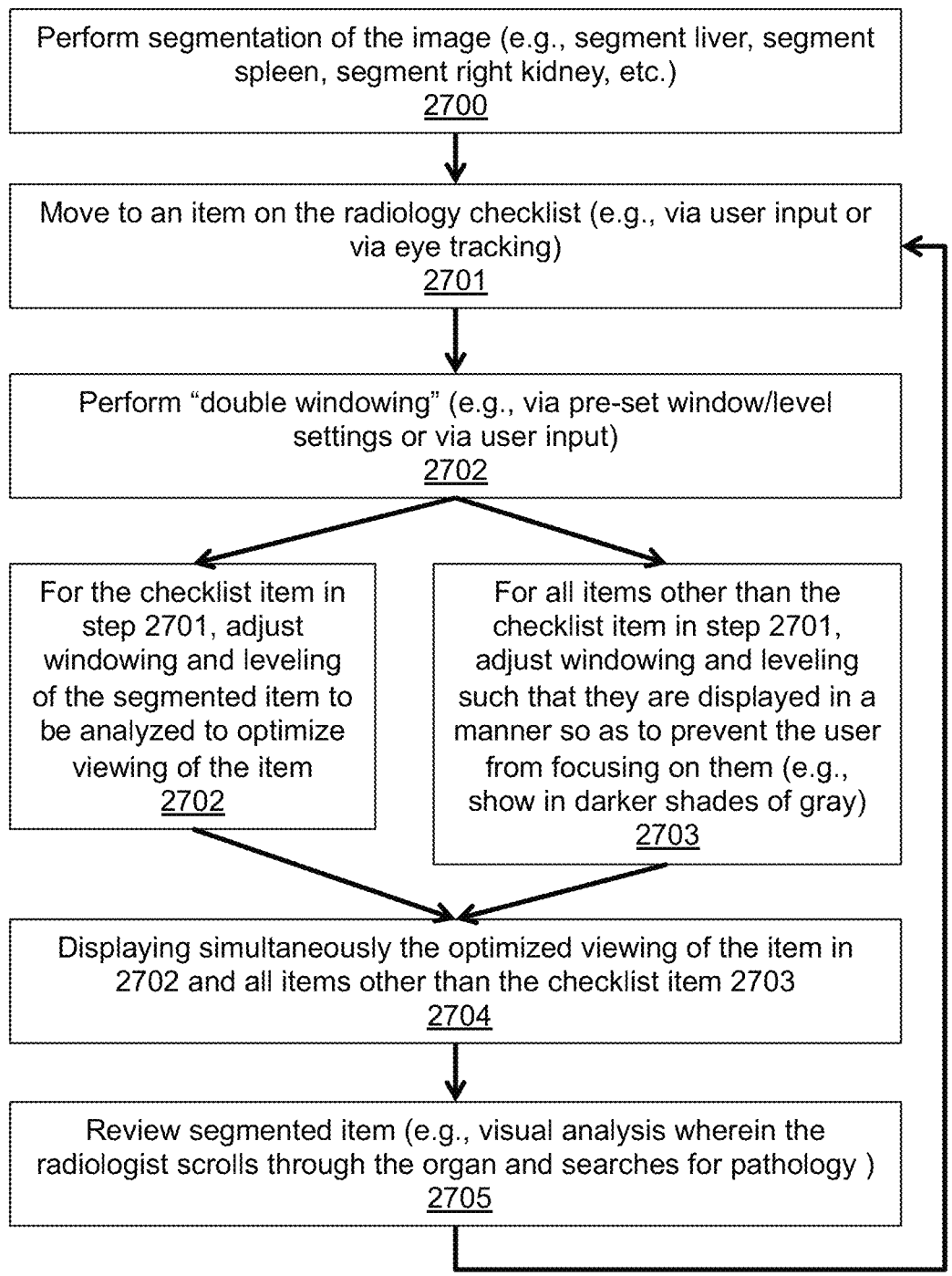
FIG. 27 illustrates a flow diagram describing an embodiment of this patent.

FIG. 27 illustrates a flow diagram describing an embodiment of this patent. Step 2700 is to perform segmentation of the image (e.g., segment liver, segment spleen, segment right kidney, etc.). Step 2701 is to move to an item on the radiology checklist (e.g., via user input or via eye tracking). Example checklists for radiology examinations can be obtained from the American College of Radiology website. For example, a CT scan of the abdomen includes the liver, spleen, gallbladder, pancreas, adrenal glands, kidneys, and so on. Step 2702 is to perform "double windowing" (e.g., via pre-set window/level settings or via user input). Step 2702 is to adjust windowing and leveling of the segmented checklist item in step 2701 to be analyzed to optimize viewing of the item. Step 2703 is to adjust windowing and leveling such that they are displayed in a manner so as to prevent the user from focusing on them (e.g., show in darker shades of gray) for all items other than the checklist item in step 2701. Step 2704 is to display simultaneously the optimized viewing of the item in 2702 and all items other than the checklist item 2703. Step 2705 is to review segmented item (e.g., visual analysis wherein the radiologist scrolls through the organ and searches for pathology).

Figure 28A:
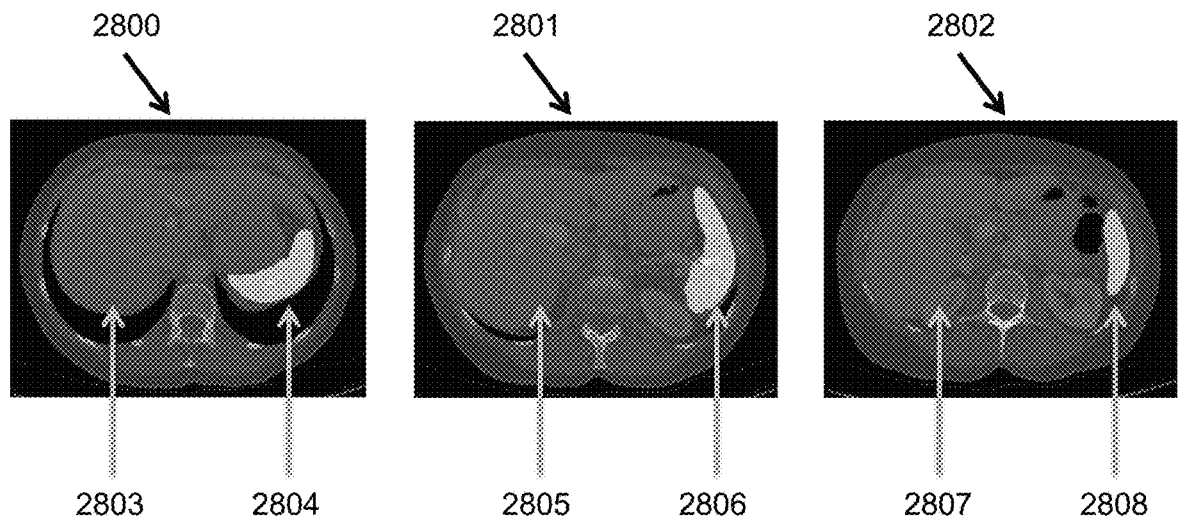
FIG. 28A illustrates three representative slices of the spleen with "double windowing".

FIG. 28A illustrates three representative slices of the spleen with "double windowing". The dataset is a CT scan of the chest with IV contrast and contained 181 slices. Slice 2800 is at position 115 of 181. Slice 2801 is at position 125 of 181. Slice 2802 is at position 133 of 181. In this embodiment, each of the organs on the radiologist's checklist have been segmented. In this example, the spleen is shown with "double windowing". During viewing of the spleen, a grayscale setting for the spleen is set with a window level of 76 and window width of 419. This was windowed by a user to determine the best possible settings for visualization of the spleen. A grayscale setting for the remainder of the structures in the CT chest dataset is set with a window level of 533 and window width of 2285. On slice 2800, the spleen 2804 is optimized with its window and level setting. The remaining structures 2803 are displayed in a window and level setting, which has been designed to be darkened. In slice 2801, the spleen 2806 is optimized with its window and level setting. The remainder of the structures 2805 are displayed in a window and level setting, which has been designed to be darkened, settings described above. In slice 2802, the spleen 2808 is optimized with its window and level setting. The remainder of the structures 2807 are displayed in a window and level setting, which has been designed to be darkened, settings described above. This is an improvement for the radiologist because it helps the radiologist focus on the spleen more during the time at which the spleen is being examined. This also prevents the radiologist from getting distracted from other bright pixels within the dataset that are not related to the spleen.

Figure 28B:
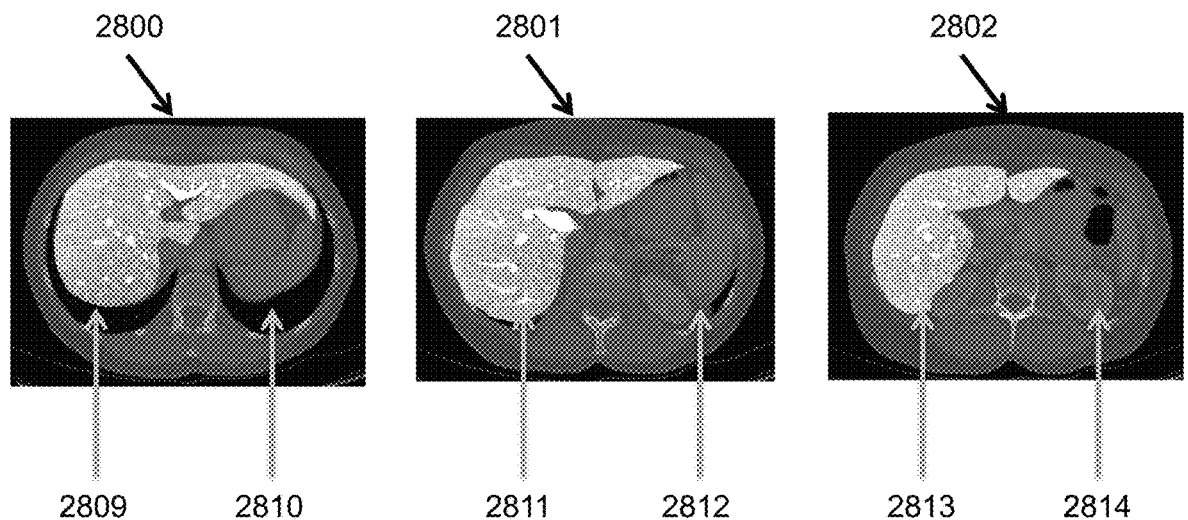
FIG. 28B illustrates three representative slices of the liver with "double windowing".

FIG. 28B illustrates three representative slices of the liver with "double windowing". This is the same CT scan of the chest with IV contrast containing 181 slices as shown in FIG. 28A. Slice 2800 is at position 115 of 181. Slice 2801 is at position 125 of 181. Slice 2802 is at position 133 of 181. In this embodiment, each of the organs on the radiologist's checklist have been segmented. In this example, the liver is shown with "double windowing". A grayscale setting for the liver is set with a window level of 117 and a window width of 166. This was windowed by a user to determine the best possible settings for visualization of the liver. During viewing of the liver, a grayscale setting for the remainder of the structures in the CT abdomen/pelvis dataset is set with a window level of 475 and window width of 2618. In slice 2800, the liver 2809 is optimized with its window and level setting. The remainder of the structures 2810 are displayed in a window and level setting, which has been designed to be darkened, settings described above. In slice 2801, the liver 2811 is optimized with its window and level setting. The remainder of the structures 2812 are displayed in a window and level setting, which has been designed to be darkened, settings described above. In slice 2802, the liver 2813 is optimized with its window and level setting. The remainder of the structures 2814 are displayed in a window and level setting, which has been designed to be darkened, settings described above. In some embodiments, more than one organ can be shown in optimal configurations and all other pixels/voxels assigned a window/level setting designed to be darkened. For example, the adrenal glands may both be shown in optimal window/leveling at the same time. A suggested terminology for this would be "triple" windowing or "higher level" windowing and leveling.

Figure 29:
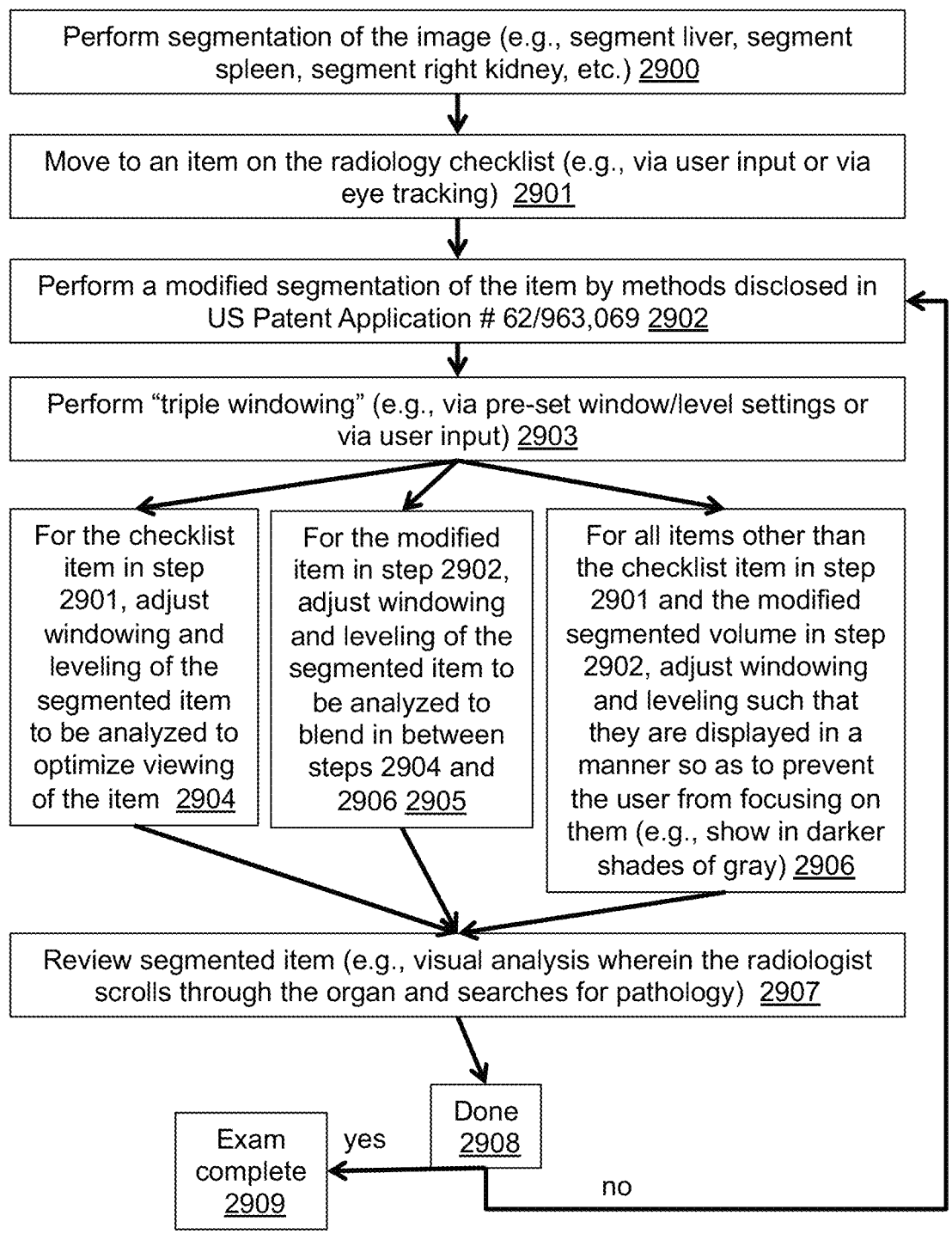
FIG. 29 illustrates a flow diagram describing an embodiment of this patent.

FIG. 29 illustrates a flow diagram describing an embodiment of this patent. Step 2900 is to perform segmentation of the image (e.g., segment liver, segment spleen, segment right kidney, etc.). Step 2901 is to move to an item on the radiology checklist (e.g., via user input or via eye tracking). Step 2902 is to perform a modified segmentation of the item by methods disclosed in U.S. Patent Application No. 62/963,069. Step 2903 is to perform "triple windowing" (e.g., via pre-set window/level settings or via user input). In step 2904, for the checklist item in step 2901, adjust windowing and leveling of the segmented item to be analyzed to optimize viewing of the item. In Step 2905, for the modified item in step 2902, adjust windowing and leveling of the segmented item to be analyzed to blend in between steps 2904 and 2906. In Step 2906, for all items other than the checklist item in step 2901 and the modified segmented volume in step 2902, adjust windowing and leveling such that they are displayed in a manner so as to prevent the user from focusing on them (e.g., show in darker shades of gray). Step 2907 is to review segmented item (e.g., visual analysis wherein the radiologist scrolls through the organ and searches for pathology). Step 2908 is to assess whether all of the structures in the examination have been analyzed. If not, the next step is to proceed to step 2902. If yes, then the review is complete 2909. A suggested terminology for this process is called "halo windowing and leveling".

Figure 30A:
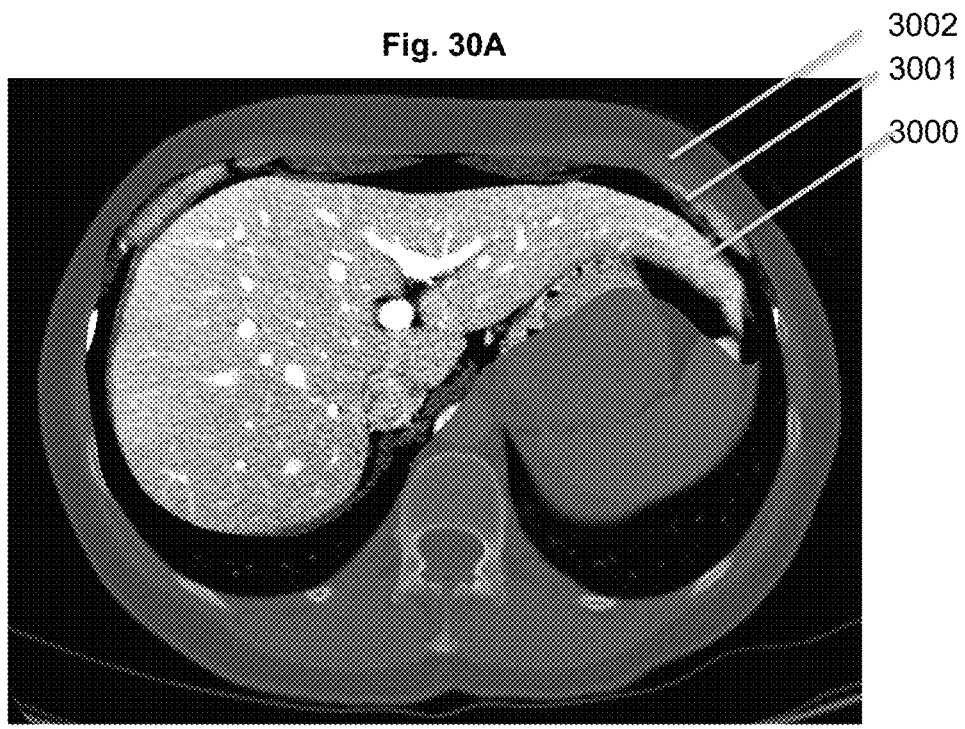
FIG. 30A illustrates a first example of "halo windowing".

FIG. 30A illustrates a first example of "halo windowing". 3000 illustrates the liver with a window level grayscale setting for the liver is set with a window level of 117 and a window width of 166. This was windowed by a user to determine the best possible settings for visualization of the liver. 3001 illustrates a modified segmented region with a "halo" appearance with a window level grayscale setting for the liver halo set with a window level of 33 and a window width of 427. This was windowed by a user to determine the best possible settings for visualization of the tissues immediately adjacent to the liver, which could have relevance to interpretation of the liver. 3002 illustrates all remaining tissues, which have a window level grayscale setting for the remainder of the structures in the CT chest dataset is set with a window level of 475 and window width of 2618. This overall process improves upon the existing art by modifying the images so that the user (e.g., radiologist) focuses on the liver during the liver portion of the examination and is not distracted by other bright voxels.

Figure 30B:
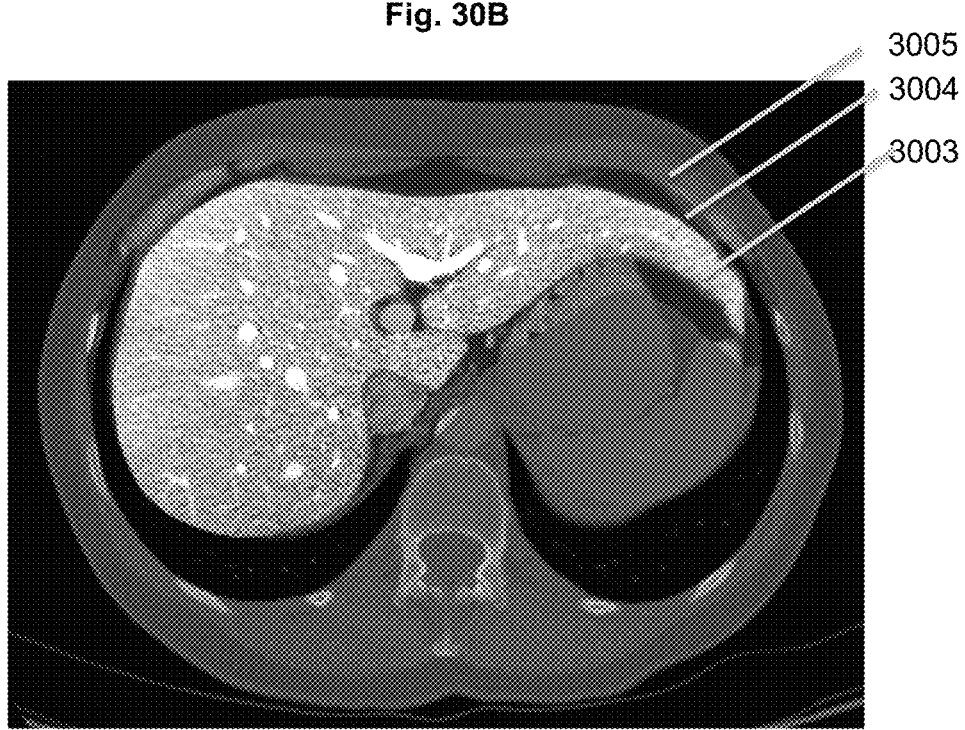
FIG. 30B illustrates a second example of "halo windowing".

FIG. 30B illustrates a second example of "halo windowing". 3003 illustrates the liver with a window level grayscale setting for the liver is set with a window level of 117 and a window width of 166. This was windowed by a user to determine the best possible settings for visualization of the liver. 3001 illustrates a modified segmented region with a "halo" appearance with a window level grayscale setting for the liver halo set with a window level of 71 and window width of 357. Note that in FIG. 30A that the window level was 33 and a window width of 427 for the halo. This embodiment shows that the halo can be independently adjusted in its appearance as compared to the organ of interest and the remaining structures in the abdomen. This was windowed by a user to determine the best possible settings for visualization of the tissues immediately adjacent to the liver, which could have relevance to interpretation of the liver. 3005 illustrates all remaining tissues, which have a window level grayscale setting for the remainder of the structures in the CT chest dataset is set with a window level of 475 and window width of 2618. This overall process improves upon the existing art by modifying the images so that the user (e.g., radiologist) focuses on the liver during the liver portion of the examination and is not distracted by other bright voxels. In some embodiments, multiple halos with each halo having a unique window level setting can be performed so as to slowly alter the window level settings in a radial fashion outward from the organ.

Figure 31:
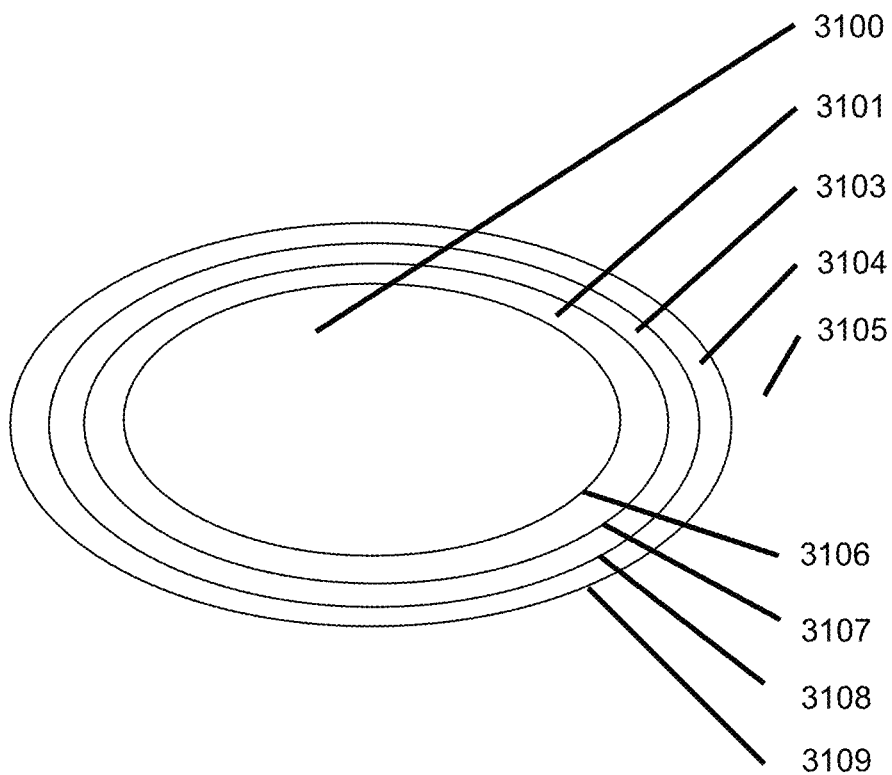
FIG. 31 illustrates multiple halos.

FIG. 31 illustrates multiple halos. Each layer of voxels outward would have a slightly more dim appearance. The organ of interest 3100 is given a first window level setting. A first halo 3101 immediately abutting the organ of interest 3000 is illustrated between the first line 3106 and the second line 3107 as a second window level setting. A second halo 3103 immediately abutting the first halo 3101 is illustrated between the second line 3107 and the third line 3108 as a third window level setting. A third halo 3104 immediately abutting the second halo 3103 is illustrated between the third line 3108 and the fourth line 3109 as a fourth window level setting. Finally, a four region of interest abutting the third halo 4310 is illustrated and has a fifth window level setting. Note that any of these regions can can be changed in thickness. For example, a halo could be one voxel thick, two voxels thick, three voxels thick, and so on. It is also important to note that the window level settings inside each individual halo can be adjusted independently from one another.

FIG. 32 illustrates a method of generating a modified segmented structure. Step 100 is loading a three-dimensional imaging dataset. Step 3201 is performing segmentation of a structure within the imaging dataset. Step 3202 is determining the coordinates of a set of voxels that correspond to the outer surface of the segmented structure. Step 3203 is determining at least one layer of voxels external to the outer surface of the segmented structure wherein the one layer of voxels is contiguous with the outer surface of the segmented structure. Step 3204 is adding the at least one layer of voxels external to the outer surface of the segmented structure to generate a modified segmented structure. For example, the surface layer of voxels can be identified. The surface layer of voxels can be identified by going from either the center voxel of the organ in the outward direction and analyzing voxel properties to determine to voxel at the surface. Next, sequentially adds voxels from the outer shell of the structure in a step-wise fashion for a variable number of steps. During each step, additional voxels surrounding the segmented structure tissue would be added.

Figure 33A:
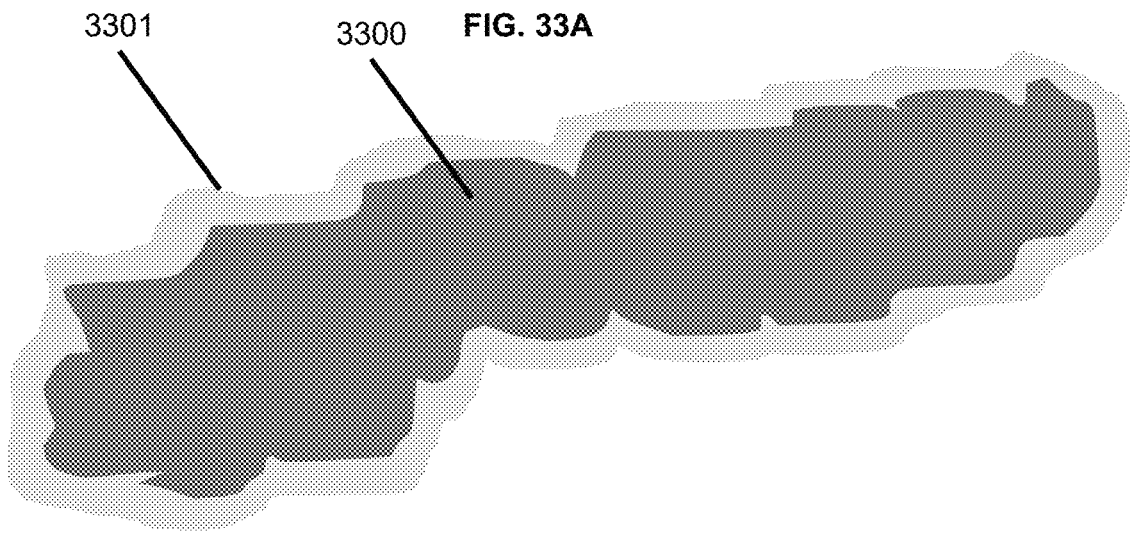
FIG. 33A illustrates a substantially equal layer of voxels added to the outer surface of the segmented anatomic structure.

FIG. 33A illustrates a substantially equal layer of voxels added to the outer surface of the segmented anatomic structure. 3300 illustrates the segmented anatomic structure, which in this case is the pancreas. 3301 illustrates the added layer of voxels to the outer surface of the segmented anatomic structure, which in this case is the fat in the retroperitoneum that surrounds the pancreas. Note that in this example, approximately the same amount of voxels is added on all sides of the segmented structure.

Figure 33B:
FIG. 33B illustrates a CT scan showing a substantially equal layer of voxels added to the outer surface of the segmented anatomic structure.

FIG. 33B illustrates a CT scan showing a substantially equal layer of voxels added to the outer surface of the segmented anatomic structure to create a modified segmented anatomic structure. 3302 illustrates a line showing the outer boundary of the modified segmented structure. Note that some of the colon, spleen, vascular structure, retroperitoneal fat, and left adrenal gland are included in the modified segmented anatomic structure.

FIG. 34 illustrates layers of voxels added in a non-uniform manner. 3400 illustrates a descriptive text box for a first example of non-uniform adding of layers. Voxel could be preferentially added to some portions of the periphery of the segmented anatomic structure based on voxel location relative to the segmented anatomic structure (e.g., superior aspect). 3401 illustrates the segmented anatomic structure (e.g., pancreas). 3402 illustrates the layer of voxels added to generate the modified segmented structure. Note that the layer of voxels added is thicker at the top of the segmented anatomic structure than at the bottom of the segmented anatomic structure; therefore, the amount of voxels added to the segmented anatomic structure is non-uniform. 3403 illustrates a descriptive text box for a second example of non-uniform adding of layers. Voxel units could be preferentially added to some portions of the of the periphery of the segmented anatomic structure based on voxel data unit (e.g., up to 4 extra layers of voxels are added if and only if those voxels have Hounsfield Units in the range of 10-20). 3404 illustrates the segmented anatomic structure, which in this case is the pancreas. 3405 illustrates the layer of voxels added to generate the modified segmented structure. 3406 illustrates some additional findings (e.g., fat stranding near the tail of the pancreas). 3407 illustrates an asymmetrically increased amount of voxels added in the region of the additional findings 3406. 3408 illustrates a descriptive text box for a third example of non-uniform adding of layers.

Specific anatomic structure segmented (e.g., add a minimum of 10 voxels for the pancreas, but add a minimum of 20 voxels for the kidney). 3409 illustrates a first segmented anatomic structure, which in this case is the pancreas. 3410 illustrates the layer of voxels added to generate the modified segmented structure of the pancreas. 3411 illustrates a first segmented anatomic structure, which in this case is the kidney. 3412 illustrates the layer of voxels added to generate the modified segmented structure of the kidney.

Figure 35A:
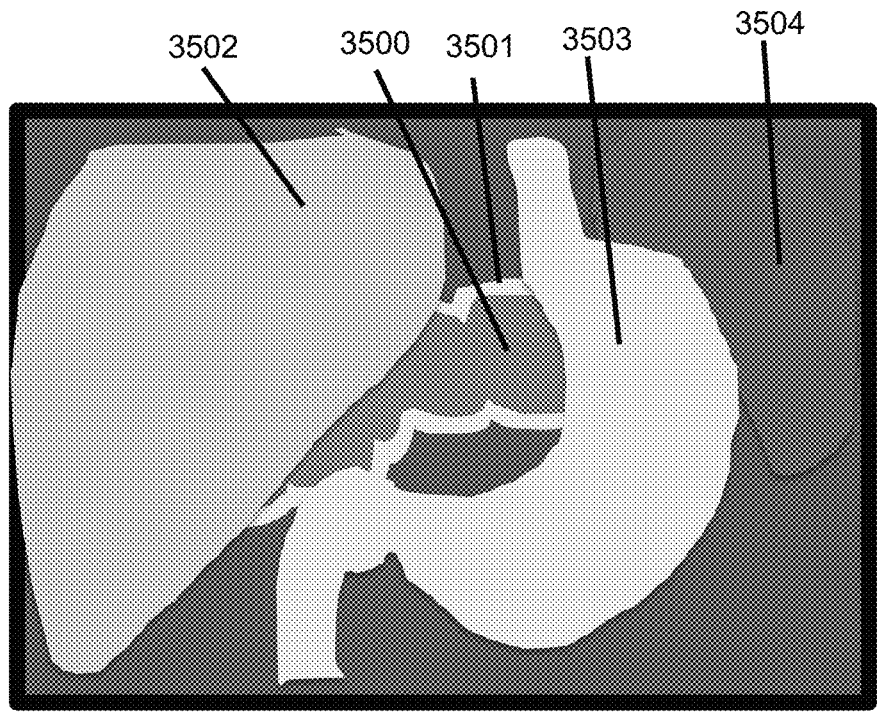
FIG. 35A illustrates an image of the abdomen.

FIG. 35A illustrates an image of the abdomen. 3500 illustrates the segmented structure, which in this case is the pancreas. 3501 voxels added to generate the modified segmented structure. Note that the voxels are shown in light gray for illustrative purposes. 3502 illustrates the liver. 3503 illustrates the stomach. 3504 illustrates the spleen.

Figure 35B:
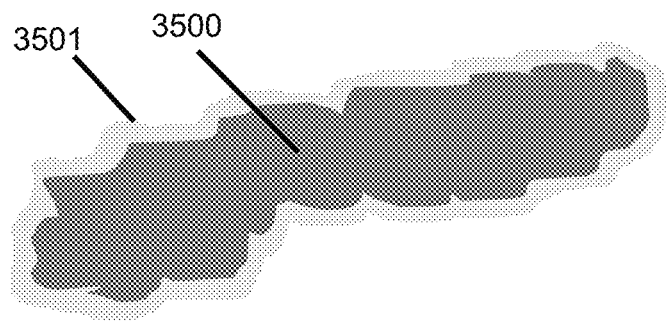
FIG. 35B illustrates subtracting the all tissues except the modified segmented volume of the pancreas.

FIG. 35B illustrates subtracting the all tissues except the modified segmented volume of the pancreas. 3500 illustrates the segmented structure, which in this case is the pancreas. 3501 voxels added to generate the modified segmented structure.

Figure 35C:
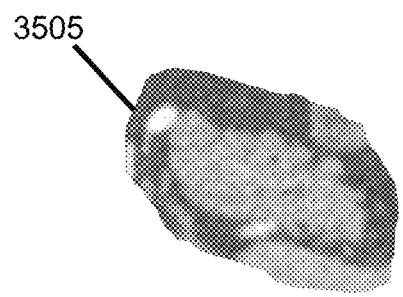
FIG. 35C illustrates a CT scan showing subtraction of all tissues except the modified segmented volume of the pancreas.

FIG. 35C illustrates a CT scan showing subtraction of all tissues except the modified segmented volume of the pancreas. 3505 illustrates a line showing the outer boundary of the modified segmented structure. Note that some of the colon, spleen, vascular structure, retroperitoneal fat, and left adrenal gland are included in the modified segmented anatomic structure.

Figure 36A:
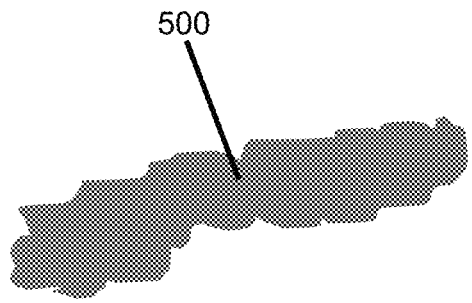
FIG. 36A illustrates the segmented structure.

FIG. 36A illustrates the segmented structure. 3600 illustrates the pancreas.

Figure 36B:
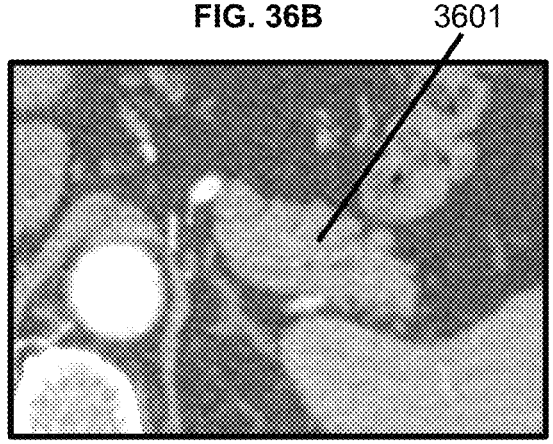
FIG. 36B illustrates a CT scan showing the pancreas.

FIG. 36B illustrates a CT scan showing the pancreas. 3601 shows the pancreas.

Figure 36C:
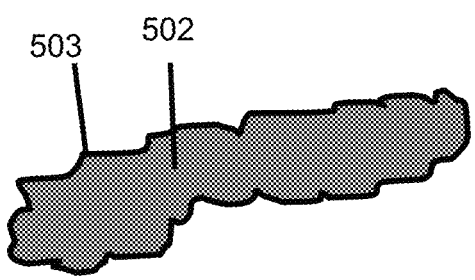
FIG. 36C illustrates the segmented structure with a line denoting the outer boundary of the segmented structure.

FIG. 36C illustrates the segmented structure with a line denoting the outer boundary of the segmented structure. 3602 illustrates the pancreas. 3603 illustrates a line denoting the boundary of the pancreas.

Figure 36D:
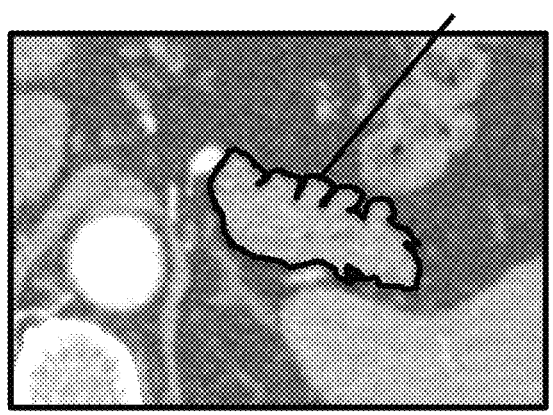
FIG. 36D illustrates a CT scan showing the pancreas with a line denoting the outer boundary of the segmented structure.

FIG. 36D illustrates a CT scan showing the pancreas with a line denoting the outer boundary of the segmented structure. 3604 illustrates a line denoting the outer boundary of the pancreas.

Figure 36E:
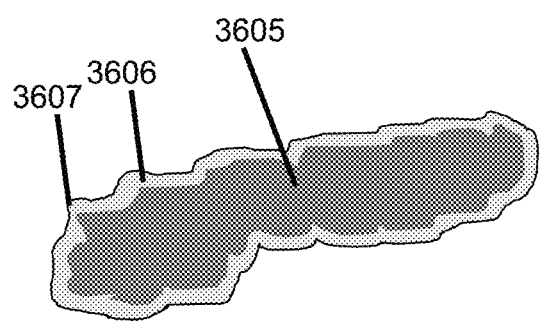
FIG. 36E illustrates the segmented structure and the modified segmented structure with a line denoting the outer boundary of the segmented structure.

FIG. 36E illustrates the segmented structure and the modified segmented structure with a line denoting the outer boundary of the segmented structure. 3605 illustrates the pancreas. 3606 illustrates the modified segmented structure wherein voxels are added. 3607 illustrates a line denoting the outer boundary of the modified segmented structure.

Figure 36F:
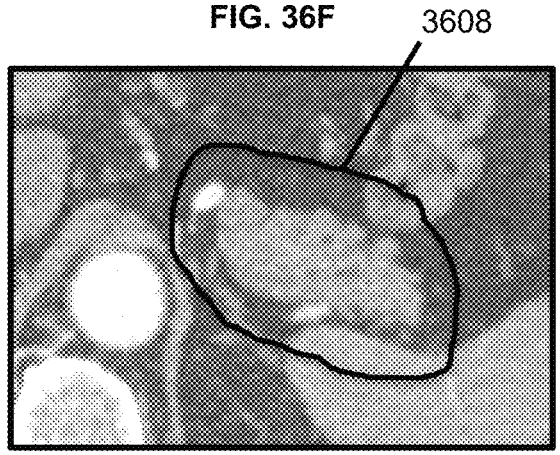
FIG. 36F illustrates a CT scan showing the pancreas with a line denoting the outer boundary of the modified segmented structure.

FIG. 36F illustrates a CT scan showing the pancreas with a line denoting the outer boundary of the modified segmented structure. 3608 illustrates a line denoting the outer boundary of the modified segmented structure.

Figure 37A:
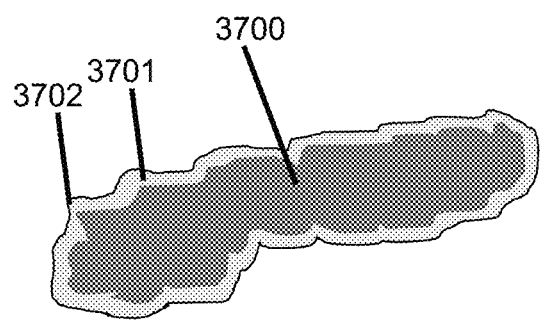
FIG. 37A illustrates a first appearance of the line demarking the outer boundary of the modified segmented structure.

FIG. 37A illustrates a first appearance of the line demarking the outer boundary of the modified segmented structure. 3700 illustrates the pancreas. 3701 illustrates the layers of voxels added surrounding the pancreas to generate the modified segmented volume. 3702 illustrates a solid black line demarking the outer layer of voxels in the modified segmented volume.

Figure 37B:
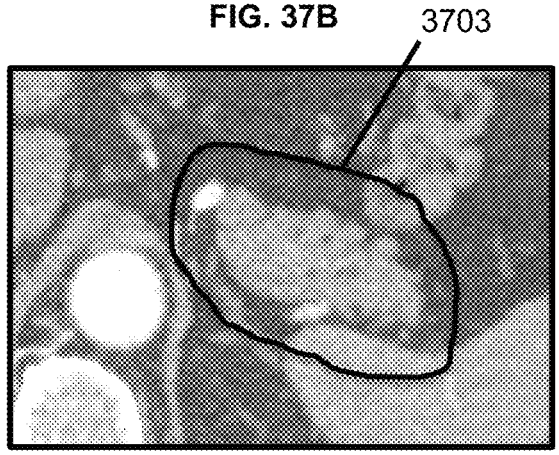
FIG. 37B shows the corresponding line demarking the outer boundary of the modified segmented structure in a CT scan.

FIG. 37B shows the corresponding line demarking the outer boundary of the modified segmented structure in a CT scan. 3703 illustrates a solid, black line representing the outer boundary of the modified segmented structure in a CT scan.

Figure 37C:
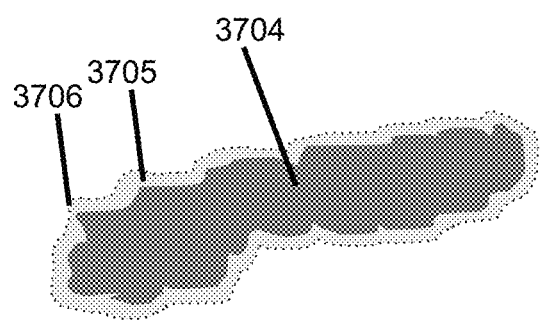
FIG. 37C illustrates a second appearance of the line demarking the outer boundary of the modified segmented structure.

FIG. 37C illustrates a second appearance of the line demarking the outer boundary of the modified segmented structure. 3704 illustrates the pancreas. 3705 illustrates the layers of voxels added surrounding the pancreas to generate the modified segmented volume. 3706 illustrates a dotted, black line demarking the outer layer of voxels in the modified segmented volume.

Figure 37D:
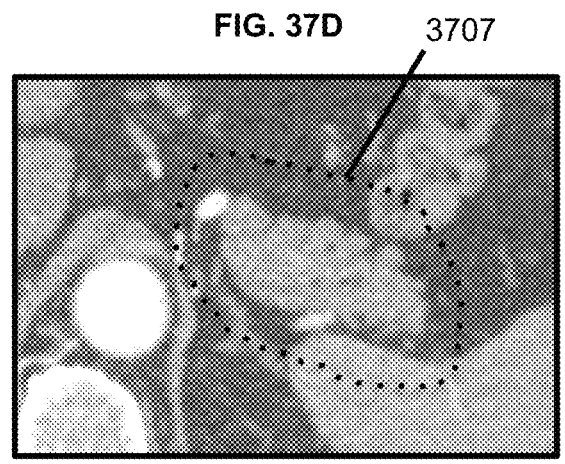
FIG. 37D shows the corresponding dotted line demarking the outer boundary of the modified segmented structure in a CT scan.

FIG. 37D shows the corresponding dotted line demarking the outer boundary of the modified segmented structure in a CT scan. 3707 illustrates a dotted, black line representing the outer boundary of the modified segmented structure in a CT scan. Multiple lines could be shown to denote why certain voxels are included in the modified segmented volume or are not included in the modified segmented volume. A variety of appearances of the lines could be used, which includes, but is not limited to, the following: dotted; solid; dashed; thin weight; medium weight; thick weight; varying colors; flashing; or other appearances.

Figure 38:
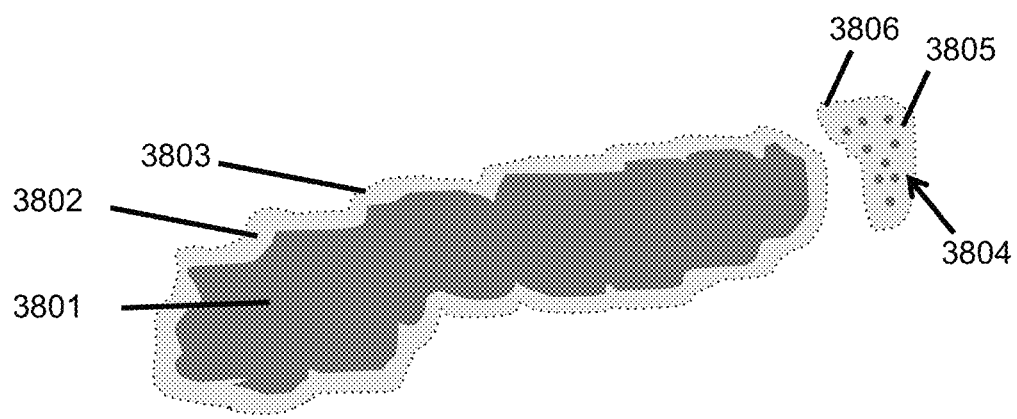
FIG. 38 illustrates the inclusion of voxels in a non-contiguous manner.

FIG. 38 illustrates the inclusion of voxels in a non-contiguous manner. 3800 illustrates a text box. Voxel units could be added to generate a non-contiguous halo (e.g., human or AI selection of adjacent item that is relevant to the main anatomic structure of interest). 3801 illustrates the segmented structure. 3802 illustrates the additional layers of voxels added to generate the modified segmented structure. 3803 illustrates a dotted line to demark the outer boundary of the segmented anatomic structure. 3804 illustrates an additional findings which are relevant to the segmented anatomic structure (e.g., fat stranding near the pancreatic tail). 3805 illustrates layers of voxels added to the modified segmented structure. 3806 illustrates dotted lines to demark the outer boundary of the segmented anatomic structure. Note that voxels are included in a non-contiguous manner in this embodiment.

Figure 39A:
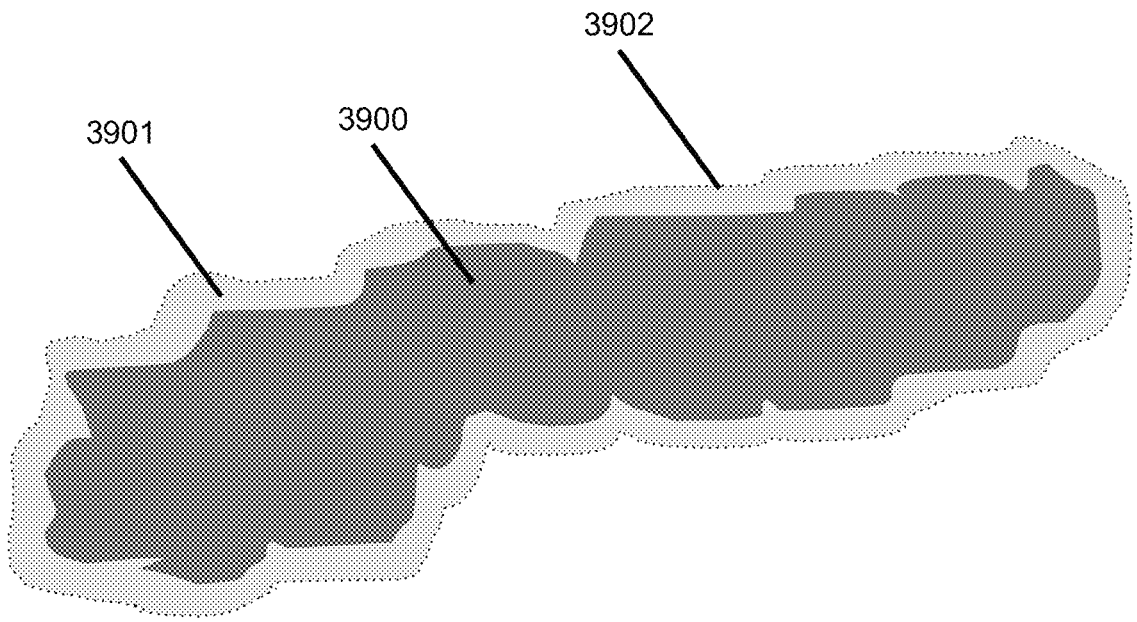
FIG. 39A illustrates a first appearance of the segmented anatomic structure and the modified segmented anatomic structure.

FIG. 39A illustrates a first appearance of the segmented anatomic structure and the modified segmented anatomic structure. In this embodiment, the segmented structure is modified independently from the voxels in the modified segmented structure. 3900 illustrates the segmented structure. 3901 illustrates the layers of voxels added to generate the modified segmented structure. 3902 illustrates a line to demark the outer boundary of the modified segmented anatomic structure.

Figure 39B:
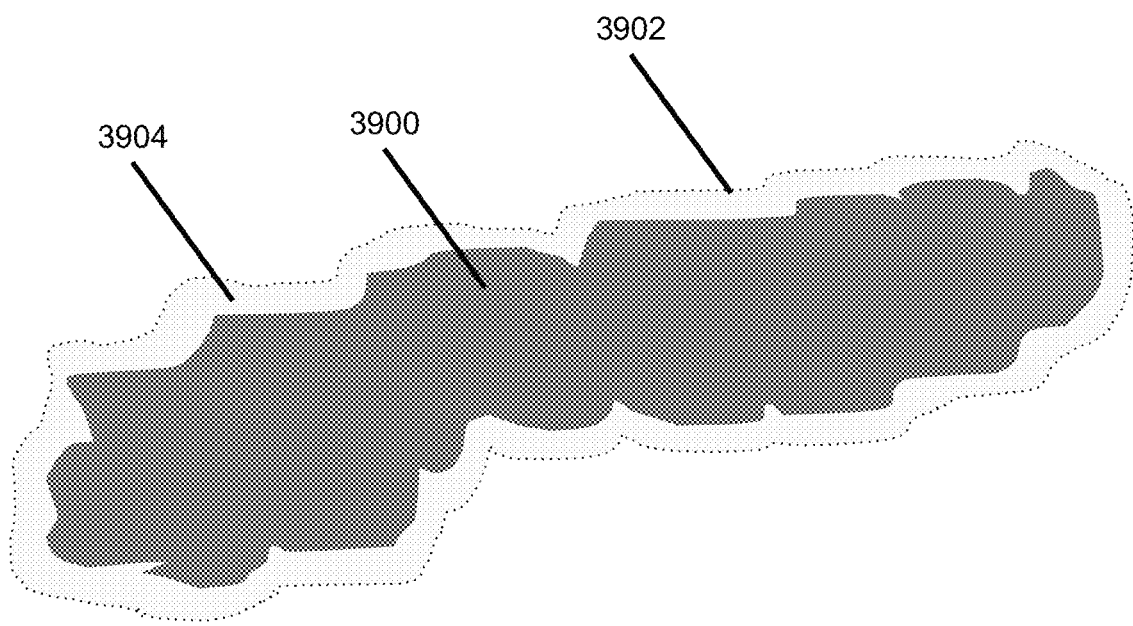
FIG. 39B illustrates a first appearance of the segmented anatomic structure and the modified segmented anatomic structure.

FIG. 39B illustrates a first appearance of the segmented anatomic structure and the modified segmented anatomic structure. In this embodiment, the segmented structure is modified independently from the voxels in the modified segmented structure. 3900 illustrates the segmented structure, which appears the same as in FIG. 39A. 3901 illustrates the layers of voxels added to generate the modified segmented structure, which appears different from FIG. 39A since it is shown as a lighter shade of gray. 3902 illustrates a line to demark the outer boundary of the modified segmented anatomic structure, which appears the same as in FIG. 39A.

FIG. 40 illustrates examples of factors which can determine the number of voxels included in the modified segmented structure. 4000 is a text box which illustrates patient demographics (e.g., age, gender, etc.). For example, infants have a smaller number of voxels due to small size. 4001 is a text box which illustrates metadata (e.g., BMI, labs, etc.). For example, BMIs>30 can have a larger number of voxels due to large size of retroperitoneal fat. For example, if the amylase and lipase are elevated, can have a larger number of voxels around the pancreas due to higher suspicion for pancreatitis and would not want to miss a fluid collection. 4002 is a text box which illustrates the type of pathology of clinical concern (e.g., infection, tumor, etc.). For example, if a stone is identified in the parotid duct, can have a larger number of voxels to improve detection of obstructive parotitis. 4003 is a text box which illustrates the type of pathology in the segmented structure. For example, if the gallbladder contains gallstones, can have a larger number of voxels to improve detection of cholecystitis.

Figure 41A:
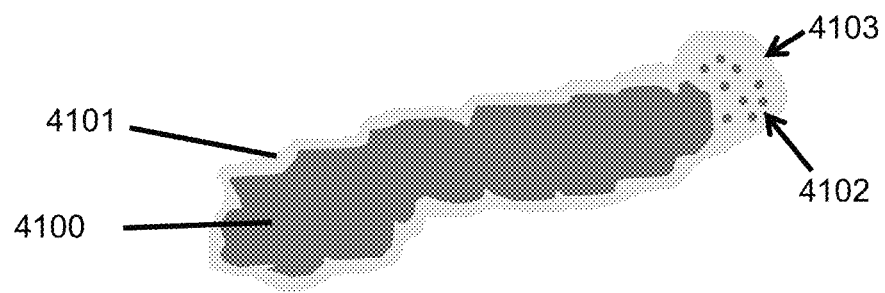
FIG. 41A illustrates the a modified segmented structure at a first time point.

FIG. 41A illustrates the a modified segmented structure at a first time point. 4100 illustrates a segmented structure (e.g., pancreas). 4101 illustrates the layer of voxels added to create the modified segmented structure. 4102 illustrates a few imaging findings near the tail of the pancreas (e.g., fat stranding indicative of pancreatitis). 4103 illustrates the asymmetric enlargement of the modified segmented volume near the tail of the pancreas.

Figure 41B:
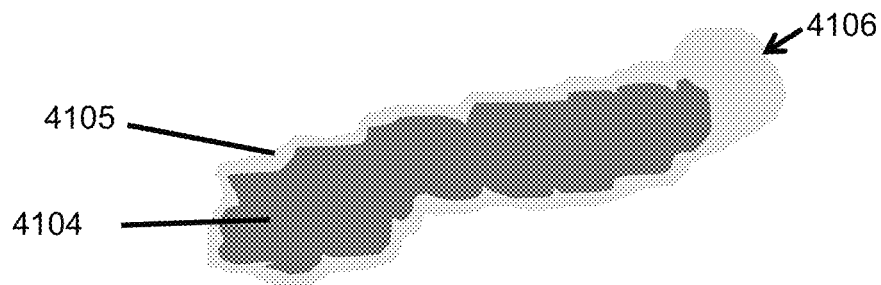
FIG. 41B illustrates the a modified segmented structure at a second time point.

FIG. 41B illustrates the a modified segmented structure at a second time point. 4104 illustrates a segmented structure (e.g., pancreas). 4105 illustrates the layer of voxels added to create the modified segmented structure. 4103 illustrates the asymmetric enlargement of the modified segmented volume near the tail of the pancreas. Note that the modified segmented structure is specifically designed to be asymmetrically enlarged at the tail of the pancreas to follow up the imaging findings seen on the first time point in FIG. 41A. No abnormalities are seen in the region of the tail of the pancreas indicating that the previously noted findings have resolved.

Figure 41C:
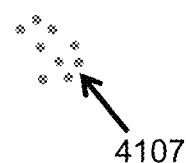
FIG. 41C illustrates the comparison of a modified segmented structure at a first time point with the modified segmented structure at a second time point to determine interval change.

FIG. 41C illustrates the comparison of a modified segmented structure at a first time point with the modified segmented structure at a second time point to determine interval change. 4107 illustrates the change in the appearance of the pancreas (e.g., the previously noted stranding has resolved).

Figure 42:
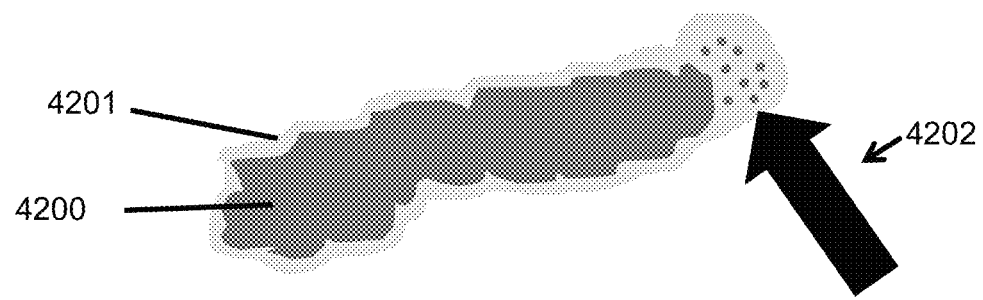
FIG. 42 illustrates inputting annotations into the modified segmented structure.

FIG. 42 illustrates inputting annotations into the modified segmented structure. 4200 illustrates the segmented structure (e.g., pancreas). 4201 illustrates the layers of voxels added surrounding the segmented structure 4200 to generate the modified segmented structure. 4202 illustrates an annotation (e.g., arrow) used to annotate a finding in the modified segmented structure.

Figure 43A:
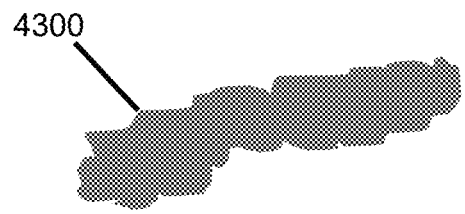
FIG. 43A illustrates a segmented structure (e.g., pancreas).

FIG. 43A illustrates a segmented structure (e.g., pancreas). 4300 illustrates the segmented structure (e.g., pancreas).

Figure 43B:
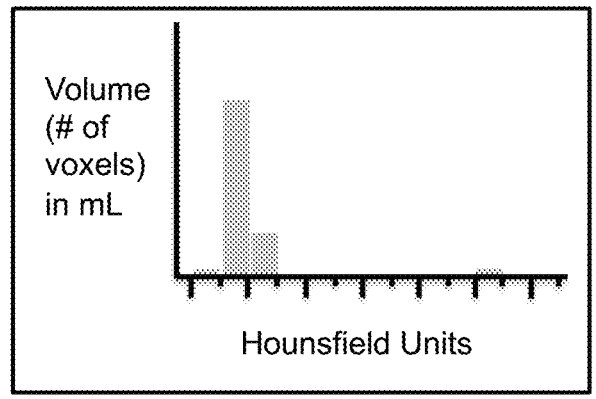
FIG. 43B illustrates an example analysis performed on the segmented structure.

FIG. 43B illustrates an example analysis performed on the segmented structure. In this example, a radiomics analysis is performed on the segmented structure (e.g., pancreas) and a histogram is shown.

Figure 43C:
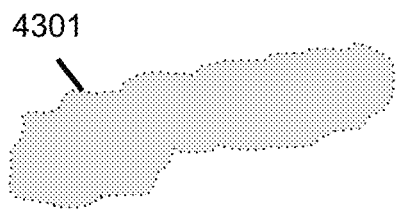
FIG. 43C illustrates a modified segmented structure (e.g., pancreas with some surrounding voxels added).

FIG. 43C illustrates a modified segmented structure (e.g., pancreas with some surrounding voxels added). 4301 illustrates the modified segmented structure (e.g., pancreas plus the additional layers of voxels added).

Figure 43D:
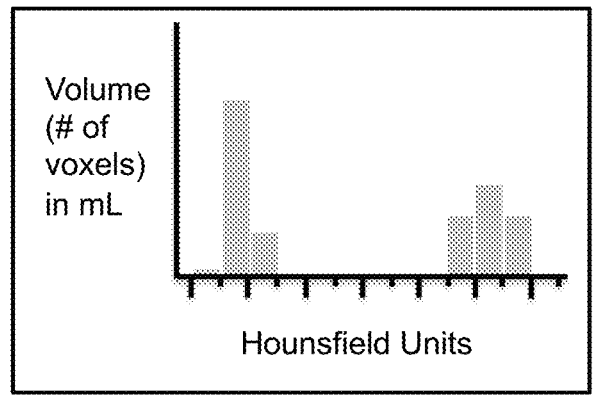
FIG. 43D illustrates an example analysis performed on the segmented structure.

FIG. 43D illustrates an example analysis performed on the segmented structure. In this example, a radiomics analysis is performed on the segmented structure (e.g., pancreas) and a histogram is shown. Note that a bimodal distribution is noted because in general the data units (e.g., Hounsfield Units) of the layers of voxels added (e.g., retroperitoneal fat) are different than the segmented structure.

Figure 43E:
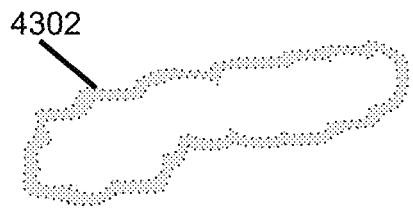
FIG. 43E illustrates a volume comprising only the surrounding voxels added, which would represent the difference between FIG. 43A and FIG. 13C.

FIG. 43E illustrates a volume comprising only the surrounding voxels added, which would represent the difference between FIG. 43A and FIG. 43C. 4302 illustrates the voxels added.

Figure 43F:
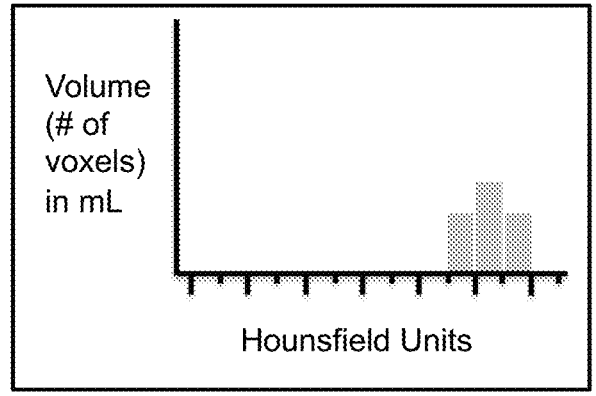
FIG. 43F illustrates an example analysis performed on the voxels added. In this example, a radiomics analysis is performed on the voxels added.

FIG. 43F illustrates an example analysis performed on the voxels added. In this example, a radiomics analysis is performed on the voxels added. Note that the initial peaks from FIG. 43B are no longer present and the analysis is only on the layers of voxels added (e.g., retroperitoneal fat).

Figure 44:
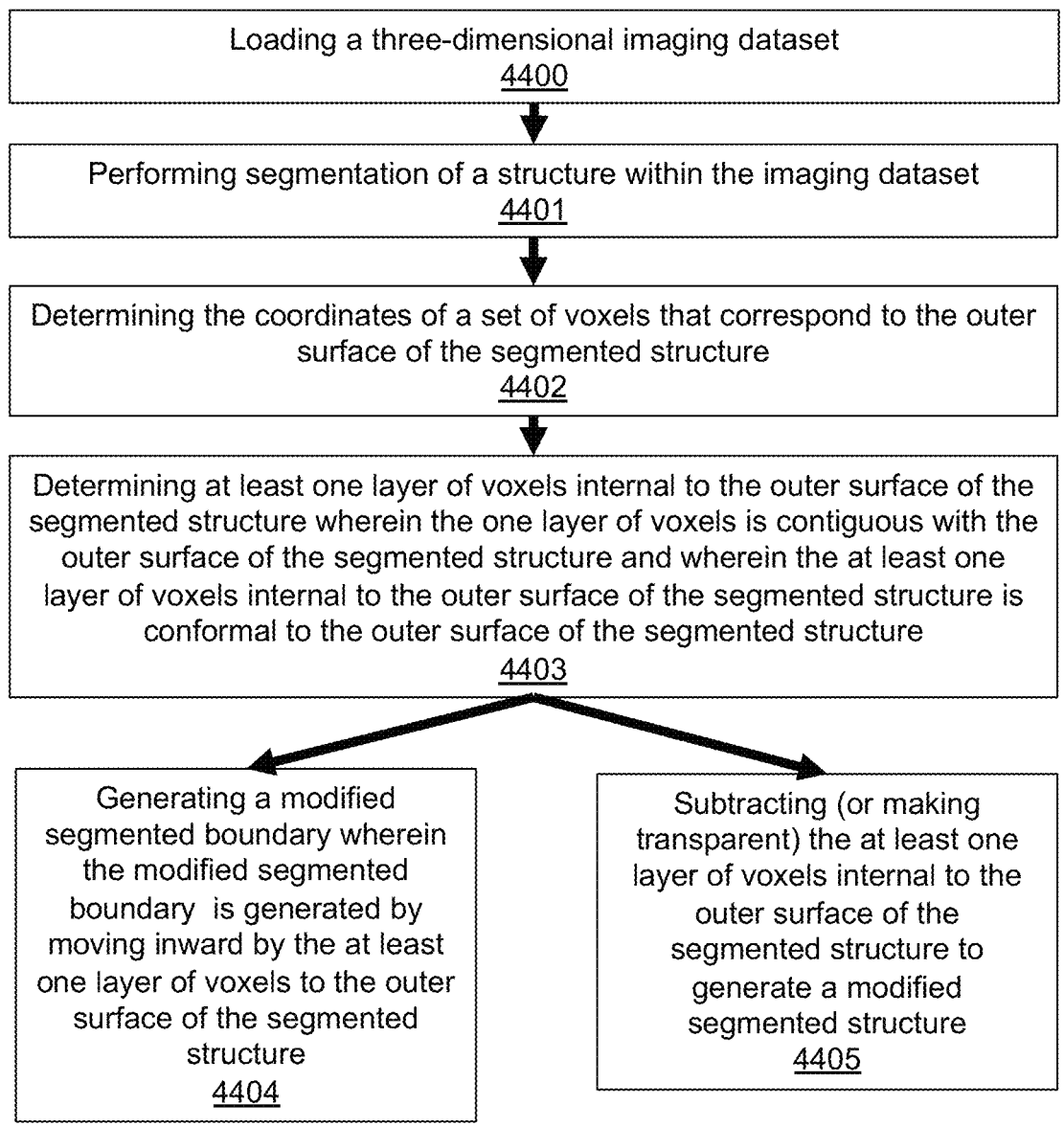
FIG. 44 illustrates a method of generating an inwardly generated modified segmented structure.

FIG. 44 illustrates a method of generating an inwardly generated modified segmented structure. 4400 illustrates loading a three-dimensional imaging dataset. 4401 illustrates performing segmentation of a structure within the imaging dataset. 4402 illustrates determining the coordinates of a set of voxels that correspond to the outer surface of the segmented structure. 4403 illustrates determining at least one layer of voxels internal to the outer surface of the segmented structure wherein the one layer of voxels is contiguous with the outer surface of the segmented structure and wherein the at least one layer of voxels internal to the outer surface of the segmented structure is conformal to the outer surface of the segmented structure. 4404 illustrates generating a modified segmented boundary wherein the modified segmented boundary is generated by moving inward by the at least one layer of voxels to the outer surface of the segmented structure. 4504 illustrates subtracting (or making transparent) the at least one layer of voxels internal to the outer surface of the segmented structure to generate a modified segmented structure.

Figure 45:
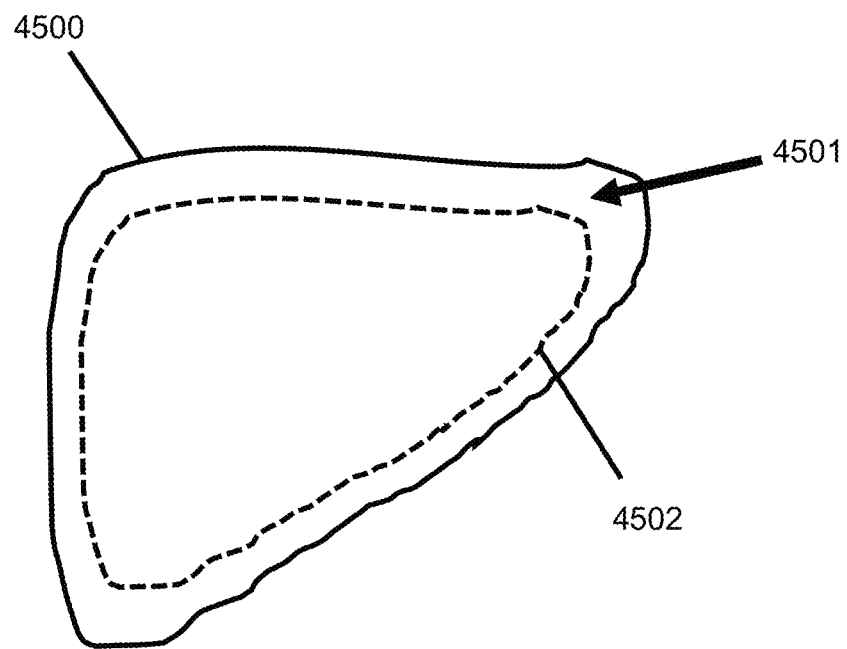
FIG. 45 illustrates an inwardly generated modified segmented structure/boundary.

FIG. 45 illustrates an inwardly generated modified segmented structure/boundary. 4500 illustrates a segmented structure. 4501 illustrates a layer of voxels internal to the segmented structure. 4502 illustrates a modified segmented structure/boundary. This can be used for additional processing. For example, consider trying to isolate the contents inside the skull. When filtering by data unit (e.g., Hounsfield Units), there is some overlap between the contrast in the blood vessels and the skull so when the filtering occurs both skull and blood vessels are subtracted. So, clip planes have to be used. A current standard process is to use clip planes. A radiologist can place a clip plane at the vertex of the skull, the right side of the skull, the left side of the skull, the front of the skull and the back of the skull. Not only does this take a significant amount of time, it also can clip off some structures of interest, such as the vertex clip plane clipping off the top of the anterior cerebral arteries. Rather than doing this laborious and inadequate effort, a user can use a modified segmented structure/boundary to segment the skull. Then move at least one layer of voxels inward from the skull. This newly formed boundary/structure will preserve even the peripherally most located blood vessels. The newly formed structure can be filtered by data unit and the vessels can be preserved and well visualized.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed is:
1. A method comprising:
   loading an imaging dataset into an image processing computer system;
   performing an initial segmentation of a structure within the imaging dataset;
   determining an outer surface of the structure;
   determining at least one layer of pixels or voxels internal to the outer surface of the structure
      wherein the at least one layer of pixels or voxels is not conformal with the outer surface of the structure, and
      wherein a non-conformal shape of said at least one layer of pixels or voxels is determined based on at least one of the group of:
         said at least one layer of pixels' data units relative to said structure's pixels data units; and
         said at least one layer of voxels' data units relative to said structure's voxels data units; and subtracting the at least one layer of pixels or voxels internal to the outer surface of the structure to generate a modified segmented structure.

2. The method of claim 1 further comprising wherein a substantially equal layer of pixels or voxels is subtracted from the outer surface of the structure.

3. The method of claim 1 further comprising wherein layers of pixels or voxels are subtracted in a non-uniform manner wherein the non-uniformity is determined by at least one of the group consisting of: pixels or voxels location(s); and, the specific structure that is segmented.

4. The method of claim 1 further comprising wherein after the pixels or voxels internal to the segmented structure are subtracted, displaying said modified segmented structure to a user.

5. The method of claim 1 further comprising displaying a line on said segmented structure to a user to denote the modified segmented structure's surface.

6. The method of claim 5 further comprising wherein the line is shown in at least one of the group comprising: a dotted fashion; a solid fashion; thin weight; medium weight; thick weight; and, color.

7. The method of claim 1 further comprising wherein the modified segmented structure is used to designate a volume for which additional image processing is performed.

8. The method of claim 7 further comprising wherein the additional image processing includes at least one of the group consisting of: radiomics; and, artificial intelligence.

9. The method of claim 8 further comprising wherein the additional image processing is used to determine a dose of a pharmaceutical.

10. The method of claim 9 further comprising wherein the additional image processing comprises visual representation adjustment logic.

11. The method of claim 7 further comprising wherein the additional image processing is performed on the structure.

12. The method of claim 11 further comprising wherein the additional image processing is used to determine a dose of a pharmaceutical.

13. The method of claim 1 further comprising wherein additional non-contiguous pixels or voxels are subtracted from said modified segmented structure to form a further modified segmented structure.

14. The method of claim 1 further comprising wherein a visual appearance of the pixels or voxels in the modified segmented structure are modified independently from the pixels or voxels in the structure.

15. The method of claim 1 further comprising wherein the number of pixels or voxels included in the modified segmented structure is dependent upon at least one of the group consisting of: a patient demographics; a metadata; a type of pathology of clinical concern; a type of pathology in the structure; and, a size of the pathology in the structure.

16. The method of claim 1 further comprising wherein the modified segmented structure at a first time point and the modified segmented structure performed on the structure at a second time point are analyzed to determine interval change.

17. The method of claim 1 further comprises wherein a number of pixels or voxels included in the modified segmented structure can be varied by at least one of the group consisting of: a user input; and, an artificial intelligence input.

18. The method of claim 1 further comprising wherein an annotations is inputted to mark the modified segmented structure.

19. An apparatus comprising:
an IO device; and
an image processor in communication with the IO device, the image processors comprising a program stored on a computer-readable non-transitory media, the program comprising instructions that perform:
loading an imaging dataset;
segmenting of a structure within the imaging dataset to define a first boundary wherein the first boundary marks an outer surface of the structure;
determining at least one layer of pixels or voxels internal to the first boundary
wherein the one layer of pixels or voxels is not conformal with the first boundary, and
wherein a non-conformal shape of said at least one layer of pixels or voxels is determined based on at least one of the group of:
said at least one layer of pixels' data units relative to said structure's pixels data units; and
said at least one layer of voxels' data units relative to said structure's voxels data units; and
generating a second boundary wherein the second boundary is generated by moving inward the at least one layer of pixels or voxels from the first boundary.

20. A non-transitory computer readable medium having computer readable code thereon for image processing, the medium comprising:
instructions for loading an imaging dataset;
instructions for performing an initial segmentation of a structure within the imaging dataset;
instructions for determining an outer surface of the structure;
instructions for determining at least one layer of pixels or voxels internal to the outer surface of the structure
wherein the at least one layer of pixels or voxels is not conformal with the outer surface of the structure, and
wherein a non-conformal shape of said at least one layer of pixels or voxels is determined based on at least one of the group of:
said at least one layer of pixels' data units relative to said structure's pixels data units; and
said at least one layer of voxels' data units relative to said structure's voxels data units; and
instructions for subtracting the at least one layer of pixels or voxels internal to the outer surface of the structure to generate a modified segmented structure.

* * * * *